(12) United States Patent
Kaul et al.

(10) Patent No.: US 10,081,601 B2
(45) Date of Patent: Sep. 25, 2018

(54) GLUCOCEREBROSIDASE MODULATORS AND USES THEREOF

(71) Applicant: Alectos Therapeutics Inc., Burnaby (CA)

(72) Inventors: Ramesh Kaul, Burnaby (CA); Ernest J. McEachern, Burnaby (CA); Jianyu Sun, Burnaby (CA); David J. Vocadlo, Burnaby (CA); Yuanxi Zhou, Burnaby (CA); Yongbao Zhu, Burnaby (CA)

(73) Assignee: Alectos Therapeutics Inc., Burnaby (CA)

( * ) Notice: Subject to any disclaimer, the term of this patent is extended or adjusted under 35 U.S.C. 154(b) by 0 days.

(21) Appl. No.: 15/711,301

(22) Filed: Sep. 21, 2017

(65) Prior Publication Data

US 2018/0009761 A1    Jan. 11, 2018

Related U.S. Application Data

(62) Division of application No. 15/107,269, filed as application No. PCT/CA2014/051252 on Dec. 22, 2014, now Pat. No. 9,796,680.

(60) Provisional application No. 62/005,196, filed on May 30, 2014, provisional application No. 61/920,160, filed on Dec. 23, 2013.

(51) Int. Cl.
*C07D 221/20* (2006.01)

(52) U.S. Cl.
CPC .................. *C07D 221/20* (2013.01)

(58) Field of Classification Search
None
See application file for complete search history.

(56) References Cited

FOREIGN PATENT DOCUMENTS

| | | |
|---|---|---|
| WO | WO-2005/046612 A2 | 5/2005 |
| WO | WO-2007/150064 A2 | 12/2007 |
| WO | WO-2010/118282 A1 | 10/2010 |
| WO | WO-2011/049736 A1 | 4/2011 |
| WO | WO-2011/049737 A1 | 4/2011 |
| WO | WO-2013/075227 A1 | 5/2013 |
| WO | WO-2013/148103 A1 | 10/2013 |

OTHER PUBLICATIONS

Pearson et al. in Bioorganic & Medicinal Chemistry 17 (2009) 8020-8026 (Year: 2009).*
Al-Mansoori et al., "The role of alpha-synuclein in neurodegenerative diseases: from molecular pathways in disease to therapeutic approaches," Curr Alzheimer Res. 10(6):559-68 (2013).
Alberio et al., "Cellular models to investigate biochemical pathways in Parkinson's disease," FEBS J. 279(7):1146-55 (2012).
Boyd et al., "Pharmacological chaperones as therapeutics for lysosomal storage diseases," J Med Chem. 56(7):2705-25 (2013).
Bundgaard, Design and Application of Prodrugs. *A Textbook of Drug Design and Development.* Harwood Academic Publishers, 113-91 (1991).
Bundgaard, *Design of prodrugs.* Elsevier, 7-9, 21-24 (1985).
Chesselet et al., "A Pharmacological Chaperone for Lysosomal Glucocerebrosidase, Afegostat-tartrate (AT2101), Shows Benefit in a Mouse Model of PD," Abstracts from the ASENT 14th Annual Meeting. 677-8 (2012).
Clark et al., "Improved Pharmacological Chaperones for the Treatment of Neuronopathic Gaucher and Parkinson's Disease," poster for Amicus Therapeutics, Cranbury, NJ (1 page) (2011).
Dawson et al., "Genetic animal models of Parkinson's disease," Neuron. 66(5):646-61 (2010).
Fan, "A contradictory treatment for lysosomal storage disorders: inhibitors enhance mutant enzyme activity," Trends Pharmacol Sci. 24(7):355-60 (2003).
Farfel-Becker et al., "Animal models for Gaucher disease research," Dis Model Mech. 4(6):746-52 (2011).
Grabowski, "Phenotype, diagnosis, and treatment of Gaucher's disease," Lancet. 372(9645):1263-71 (2008).
Higuchi et al., *Pro-drugs as Novel Drug Delivery Systems.* American Chemical Society, 1-115 (1975).
International Search Report and Written Opinion for International Application No. PCT/CA2014/051252, dated Mar. 9, 2015 (11 pages).
Khanna et al., "The pharmacological chaperone isofagomine increases the activity of the Gaucher disease L444P mutant form of beta-glucosidase," FEBS J. 277(7):1618-38 (2010).
Kong et al., "The association between lysosomal protein glucocerebrosidase and Parkinson's disease," 17(2):143-51 (2013).
Panicker et al., "Induced pluripotent stem cell model recapitulates pathologic hallmarks of Gaucher disease," Proc Natl Acad Sci USA. 109(44):18054-9 (2012).
Parenti, "Treating lysosomal storage diseases with pharmacological chaperones: from concept to clinics," EMBO Mol Med. 1(5):268-79 (2009).
Pearson et al., "The spirocyclopropyl moiety as a methyl surrogate in the structure of I-fucosidase and I-rhamnosidase inhibitors," Bioorg Med Chem. 17(23):8020-6 (2009).
Roche, *Bioreversible Carriers in Drug Design.* Pergamon Press, 1-292 (1987).
Sardi et al., "Augmenting CNS glucocerebrosidase activity as a therapeutic strategy for parkinsonism and other Gaucher-related synucleinopathies," Proc Natl Acad Sci USA. 110(9):3537-42 (2013).
Sardi et al., "CNS expression of glucocerebrosidase corrects alpha-synuclein pathology and memory in a mouse model of Gaucher-related synucleinopathy," Proc Natl Acad Sci USA. 108(29):12101-6 (2011).
Sardi et al., "Mutant GBA1 expression and synucleinopathy risk: first insights from cellular and mouse models," Neurodegener Dis. 10(1-4):195-202 (2012).
Smith, *Introduction to the Principles of Prodrug Design.* Wright (1988).
Wermuth, Designing prodrugs and bioprecursors I: Carrier prodrugs. *The Practice of Medicinal Chemistry.* Academic Press, 671-96 (1996).
Extended European Search Report for European Application No. 14875019.3, dated Jun. 20, 2017 (7 pages).

* cited by examiner

*Primary Examiner* — Dennis Heyer
(74) *Attorney, Agent, or Firm* — Clark & Elbing LLP

(57) ABSTRACT

The invention provides compounds for modulating glycosidases, prodrugs of the compounds, and pharmaceutical compositions including the compounds or prodrugs of the compounds.

11 Claims, No Drawings
Specification includes a Sequence Listing.

GLUCOCEREBROSIDASE MODULATORS AND USES THEREOF

FIELD OF THE INVENTION

This application relates in part to compounds which modulate glycosidases and uses thereof.

BACKGROUND OF THE INVENTION

A defining pathological feature of Parkinson's disease (PD) is the abnormal accumulation of alpha-synuclein protein deposits within the brain into what are known as Lewy bodies. The accumulation of alpha-synuclein within the brain leads to the progressive death of dopaminergic neurons and downstream cognitive and behavioral impairments. In addition to PD, aggregation of alpha-synuclein is also associated with a broad group of neurodegenerative diseases known collectively as synucleopathies; examples include dementia with Lewy bodies, multiple system atrophy, Pick's disease, and corticobasal degeneration. Similarly, alpha-synuclein protein deposits and Lewy bodies are often associated with the development of Alzheimer's disease.[1] Augmentation of β-glucocerebrosidase (GCase, EC. 3.2.1.45) activity in a mouse model of PD has been implicated in reduced alpha-synuclein accumulation and delayed onset of pathology.[2,5] In addition, small-molecule GCase modulators have been shown to reduce alpha-synuclein levels and behavioural deficits in a rodent model of PD.[6,7]

Gaucher's disease (GD) is a lysosomal storage disorder caused by homozygous loss of function mutations in GBA1, the gene encoding GCase.[8] Normally, GCase present within lysosomes catalyzes hydrolytic cleavage of glucose from the glycolipid glucocerebroside (also known as glucosylceramide) within this compartment of cells. In Gaucher's disease, lysosomal GCase levels are greatly reduced or functionally absent, leading to the pathological accumulation of glucosylceramide within lysosomes. Symptoms of Gaucher's disease may include some or all of the following: enlarged spleen and liver; liver malfunction; skeletal disorders and bone lesions that may be painful; severe neurologic complications; swelling of lymph nodes and (occasionally) adjacent joints; distended abdomen; a brownish tint to the skin; anemia; low blood platelets and yellow fatty deposits on the sclera. In addition, persons affected with Gaucher's disease may be more susceptible to various infections. Current treatment of Gaucher's involves administering recombinant human GCase as an enzyme replacement therapy (ERT), which helps to control the visceral and haematological complications of Gaucher's disease. However, because the recombinant enzyme is not brain-penetrant, ERT does not improve the neurological manifestations of the disease.

International patent applications PCT/US2004/037704, filed 12 Nov. 2004, published under No. WO 2005/046612 on 26 May 2005; PCT/US2007/072016, filed 25 Jun. 2007, published under No. WO 2007/150064 on 27 Dec. 2007; PCT/US2010/030470, filed 9 Apr. 2010, published under No. WO 2010/118282 on 14 Oct. 2010; PCT/US2010/051447, filed 5 Oct. 2010, published under No. WO 2011/049736 on 28 Apr. 2011; PCT/US2010/051458, filed 5 Oct. 2010, published under No. WO 2011/049737 on 28 Apr. 2011; PCT/CA2012/001084, filed 23 Nov. 2012, published under No. WO 2013/075227 on 30 May 2013; PCT/US2013/029612, filed 7 Mar. 2013, published under No. WO 2013/148103 on 3 Oct. 2013, are directed to small-molecule modulators of GCase.

SUMMARY OF THE INVENTION

The invention provides, in part, compounds for modulating glycosidases, prodrugs of the compounds, uses of the compounds and the prodrugs, pharmaceutical compositions including the compounds or prodrugs of the compounds, and methods of treating diseases and disorders related to deficiency or overexpression of GCase, and/or accumulation or deficiency of glucosylceramide. In some embodiments, the invention provides compositions and methods to prevent and/or treat a neurodegenerative disease, including Parkinson's disease and Alzheimer's disease, or a lysosomal storage disorder, including Gaucher's disease, by administering to a patient in need thereof an effective amount of one or more of the compounds or prodrugs of the compounds described herein.

In one aspect, the invention provides a compound of Formula (I) or a pharmaceutically acceptable salt thereof:

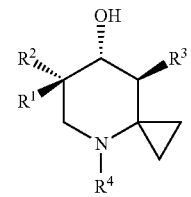

where $R^1$ may be OH and $R^2$ may be H or methyl; or $R^1$ may be F and $R^2$ may be H or F; or $R^1$ may be H and $R^2$ may be F; $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH$(cyclopropyl); and $R^4$ may be: H or $C_{1-10}$ alkyl, the $C_{1-10}$ alkyl optionally substituted from one up to the maximum number of substituents with F and/or OH.

In alternative embodiments, the invention provides a compound of Formula (Ia) or a pharmaceutically acceptable salt thereof:

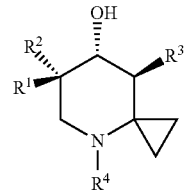

where $R^1$ may be OH and $R^2$ may be H or methyl; or $R^1$ may be F and $R^2$ may be H or F; or $R^1$ may be H and $R^2$ may be F; $R^3$ may be $C(R^5)(R^6)(R^7)$, where $R^5$ may be: H, OH, F, Cl, and $C_{1-10}$ alkyl, the $C_{1-10}$ alkyl optionally substituted from one up to the maximum number of substituents with one or more of fluoro and/or OH; $R^6$ and $R^7$ may independently be: H, F, $C_{1-10}$ alkyl, $C_{3-8}$ cycloalkylmethyl, aryl, or heteroaryl, each excluding H and F optionally substituted from one up to the maximum number of substituents with one or more of fluoro, OH or methyl; or $R^6$ and IV may be connected together with the carbon atom to which they are attached to form a ring, the ring optionally independently substituted from one up to the maximum number of substituents with one or more of fluoro, OH, or methyl; and $R^4$ may be: H, $C_{1-10}$ alkyl, the $C_{1-10}$ alkyl optionally substituted from one up to the maximum number of substituents with fluoro and/or OH; where when $R^5$ is OH, then $R^6$ and $R^7$ are other than F.

In alternative embodiments, the invention provides a compound of Formula (Ib) or a pharmaceutically acceptable salt thereof:

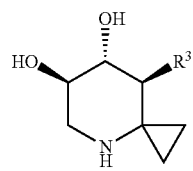

(Ib)

where $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$.

In alternative embodiments, the invention provides a compound of Formula (Ic) or a pharmaceutically acceptable salt thereof:

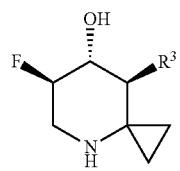

(Ic)

where $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$.

In alternative embodiments, the invention provides a compound of Formula (Id) or a pharmaceutically acceptable salt thereof:

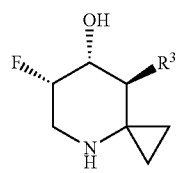

(Id)

where $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$.

In alternative embodiments, the invention provides a compound of Formula (Ie) or a pharmaceutically acceptable salt thereof:

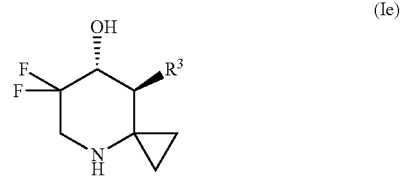

(Ie)

where $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$.

In alternative embodiments, the invention provides a compound of Formula (If) or a pharmaceutically acceptable salt thereof:

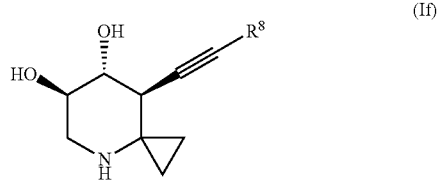

(If)

where $R^8$ may be H or $C_{1-10}$ alkyl, the $C_{1-10}$ alkyl optionally substituted from one up to the maximum number of substituents with one or more of F, Cl, $CH_3$, and/or OH.

In alternative embodiments, the compound may be a prodrug; the compound may modulate a β-glucocerebrosidase (GCase); the compound may bind to a GCase (e.g., a mammalian GCase); the compound may bind to a wild-type GCase; the compound may bind to a mutant GCase; the compound may increase protein levels of a GCase; the compound may increase activity levels of a GCase.

In alternative embodiments, a compound according to Formula (I), Formula (Ia), Formula (Ib), Formula (Ic), Formula (Id), Formula (Ie), or Formula (If) may have enhanced permeability.

In alternative embodiments, a compound according to Formula (Ib), Formula (Ic), Formula (Id), Formula (Ie), or Formula (If) may have enhanced permeability.

In alternative embodiments, a compound according to Formula (If) may have enhanced permeability.

In alternative aspects, the invention provides a pharmaceutical composition including a compound according to the invention, or a pharmaceutically acceptable salt thereof, in combination with a pharmaceutically acceptable carrier.

In alternative aspects, the invention provides methods of modulating a GCase in a subject in need thereof, or of increasing the level of GCase in a subject in need thereof, or of increasing the activity of GCase in a subject in need thereof, or of treating a neurodegenerative disease, or a lysosomal storage disease, in a subject in need thereof, by administering to the subject an effective amount of a compound of Formula (I), including any one or more of Formula (Ia)-(If), or a pharmaceutically acceptable salt thereof:

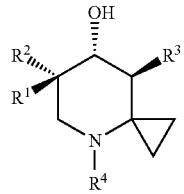

(I)

where $R^1$ may be OH and $R^2$ may be H or methyl; or $R^1$ may be F and $R^2$ may be H or F; or $R^1$ may be H and $R^2$ may be F; $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$; and $R^4$ may be: H, $C_{1-10}$ alkyl, the $C_{1-10}$ alkyl optionally substituted from one up to the maximum number of substituents with F and/or OH. The neurodegenerative disease may be Parkinson's disease, Dementia with Lewy bodies, Multiple system atrophy, Pick's disease (PiD), Corticobasal degeneration (CBD), Alzheimer's disease, Amyotrophic lateral sclerosis (ALS), Amyotrophic lateral sclerosis with cognitive impairment (ALSci), Argyrophilic grain dementia, Bluit disease, Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Myotonic dystrophy, Multi-infarct dementia, Niemann-Pick disease (type C), Pallido-ponto-nigral degeneration, Parkinsonism-dementia complex of Guam, Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Schizophrenia, Mild Cognitive Impairment (MCI), Neuropathy (including peripheral neuropathy, autonomic neuropathy, neuritis, and diabetic neuropathy), or Glaucoma. The lysosomal storage disease may be Gaucher's disease, including Type I, Type II, and Type III Gaucher's disease.

In alternative embodiments, the administering may increase the level of GCase in the subject. The subject may be a human.

In alternative aspects, the invention provides use of a compound of an effective amount of a compound of Formula (I), including any one or more of Formula (Ia)-(If), or a pharmaceutically acceptable salt thereof:

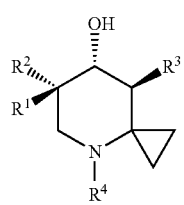

(I)

where $R^1$ may be OH and $R^2$ may be H or methyl; or $R^1$ may be F and $R^2$ may be H or F; or $R^1$ may be H and $R^2$ may be F; $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, and $C(O)NH(cyclopropyl)$; and $R^4$ may be: H, $C_{1-10}$ alkyl, the $C_{1-10}$ alkyl optionally substituted from one up to the maximum number of substituents with F and/or OH, in the preparation of a medicament. The medicament may be for modulating a GCase, for increasing the level of GCase, for increasing the activity of GCase, for treating a condition modulated by a GCase, for treating a neurodegenerative disease or a lysosomal storage disease.

In alternative aspects, the invention provides methods of synthesis to prepare a compound as described herein, or a pharmaceutically acceptable salt thereof.

This summary of the invention does not necessarily describe all features of the invention.

DETAILED DESCRIPTION

The invention provides, in part, compounds for modulating a β-glucocerebrosidase (GCase) and uses thereof.

By a "β-glucocerebrosidase" or "GCase" is meant an enzyme with glucosylceramidase activity (EC 3.2.1.45) that catalyzes the hydrolytic cleavage of the beta-glucosidic linkage of the glycolipid glucocerebroside (also known as glucosylceramide). Alternative names for a GCase include: acid beta-glucosidase, beta-GC, glucosylceramidase, Glc-Cerase, D-glucosyl-N-acylsphingosine glucohydrolase, GBA, GBA1, GBA2, and GBA3. In some embodiments, the GCase may be a mammalian GCase, such as a rat, mouse or human GCase. The GCase may be a wild-type GCase or a mutant GCase. In some embodiments, the GCase may be a wild-type mammalian GCase, such as a rat, mouse or human wild-type GCase. In some embodiments, the GCase may be a mutant mammalian GCase, such as a rat, mouse or human mutant GCase. In some embodiments, the GCase may be a human lysosomal GCase. In some embodiments, the GCase may be a human non-lysosomal GCase. In some embodiments, the GCase may be a human cytosolic GCase. In some embodiments, the GCase may have a sequence as set forth in any one of the following Accession numbers: P04062, Q9HCG7, Q9H227, P17439, P97265, Q69ZF3, Q5M868, Q7OKH2, Q2KHZ8, Q5R8E3, or Q9BDTO. In alternative embodiments, the GCase may be encoded by a sequence as set forth in any one of the following Accession numbers: NG_009783.1, NP_065995.1, NP_066024.1, NP_001121904.1, NP_001264154.1, NP_766280.2, NP_001121111.1, NP_001013109.2, NP_001005730.1, NM_001046421.2, NM_001134016.1, or NM_001008997.1. In alternative embodiments, the human GCase may have the sequence set forth below:

```
                                                            (SEQ ID NO: 1)
         10         20         30         40         50         60
    MEFSSPSREE CPKPLSRVSI MAGSLTGLLL LQAVSWASGA RPCIPKSFGY SSVVCVCNAT 70         80         90        100        110        120
    YCDSFDPPTF PALGTFSRYE STRSGRRMEL SMGPIQANHT GTGLLLTLQP EQKFQKVKGF 130        140        150        160        170        180
    GGAMTDAAAL NILALSPPAQ NLLLKSYFSE EGIGYNIIRV PMASCDFSIR TYTYADTPDD 190        200        210        220        230        240
    FQLHNFSLPE EDTKLKIPLI HRALQLAQRP VSLLASPWTS PTWLKTNGAV NGKGSLKGQP 250        260        270        280        290        300
    GDIYHQTWAR YFVKFLDAYA EHKLQFWAVT AENEPSAGLL SGYPFQCLGF TPEHQRDFIA 310        320        330        340        350        360
    RDLGPTLANS THHNVRLLML DDQRLLLPHW AKVVLTDPEA AKYVHGIAVH WYLDFLAPAK 370        380        390        400        410        420
    ATLGETHRLF PNTMLFASEA CVGSKFWEQS VRLGSWDRGM QYSHSIITNL LYHVVGWTDW 430        440        450        460        470        480
    NLALNPEGGP NWVRNFVDSP IIVDITKDTF YKQPMFYHLG HFSKFIPEGS QRVGLVASQK 490        500        510        520        530
    NDLDAVALMH PDGSAVVVVL NRSSKDVPLT IKDPAVGFLE TISPGYSIHT YLWRRQ
```

In alternative embodiments, the human GCase may have the nucleic acid sequence of a nucleic acid molecule encoding the sequence set forth in SEQ ID NO: 1.

Examples of mutant human GCase may include mutant enzymes bearing the N370S allele (mutant GCase sequence: QSVRLGSWDRGMQYSHSIITSLLYHVVGWTDWNLA LNPEGG; SEQ ID NO: 2), the L444P allele (mutant GCase sequence: SKFIPEGSQRVGLVASQKNDPDAVALMHPD GSAVVVVLNRS; SEQ ID NO: 3), the F213I allele (mutant GCase sequence: GKGSLKGQPGDIYHQTWARYIVKFL DAYAEHKLQFWAVTAE; SEQ ID NO: 4), the G202R allele (mutant GCase sequence: PTWLKTNGAVNGKG-SLKGQPRDIYHQTWARYFVKFLDAYAE; SEQ ID NO: 5), or other mutant alleles.[9]

In some embodiments, one or more of the compounds according to the invention may modulate a GCase. By "modulate" or "modulating," as used herein, is meant changing, by either increase or decrease. Accordingly, a "modulatory compound", as used herein, includes any compound capable of either changing GCase expression (e.g., at the level of transcription, translation, or post-translation) or protein activity or biological function.

In some embodiments, one or more of the compounds according to the invention may inhibit the activity of a GCase, for example, the ability to inhibit the cleavage of glucose from glucosylceramide or the ability to inhibit the cleavage of glucose from a suitable substrate molecule such as, for example, 4-methylumbelliferone-β-D glucopyranoside. By "inhibit," "inhibition" or "inhibiting" means a decrease by any value between about 10% and about 90%, or of any value between about 30% and about 60%, or over about 100%, or a decrease by about 1-fold, 2-fold, 5-fold, 10-fold or more, in comparison to a reference sample or compound, or in comparison to a wild type GCase. It is to be understood that the inhibiting does not require full inhibition. In some embodiments, the inhibition may be transient. For example, one or more of the compounds according to the invention may inhibit a GCase within a specific cellular compartment, such as the endoplasmic reticulum or Golgi apparatus, but may dissociate and no longer inhibit a GCase within another cellular compartment, for example a lysosomal compartment.

In some embodiments, one or more of the compounds according to the invention that inhibit the activity of a GCase may also stabilize the same enzyme. By "stabilization" is meant preventing denaturation, proteolysis, or degradation of the enzyme. In some embodiments, one or more of the compounds according to the invention may stabilize a GCase within a specific cellular compartment, such as the endoplasmic reticulum or Golgi apparatus. In some embodiments, one or more of the compounds according to the invention that exhibit stabilization of a GCase may enhance trafficking of the enzyme from the ER or Golgi through the secretory pathway to its proper cellular destination, for example, a lysosomal compartment. In some embodiments, one or more of the compounds according to the invention that enhance trafficking of a GCase to its proper cellular destination may dissociate from the enzyme once the enzyme reaches that destination, for example, a lysosomal compartment. In some embodiments, one or more compounds that exhibit stabilization of a GCase and enhance trafficking of a GCase may increase the protein level of a GCase, for example, in a lysosomal compartment. In some embodiments, one or more compounds that increase the protein level of a GCase may also increase the activity level of a GCase, for example, in a lysosomal compartment.

In some embodiments, one or more of the compounds according to the invention may specifically bind a GCase. In alternative embodiments, one or more of the compounds according to the invention may specifically bind the active site of a GCase. In some embodiments, one or more of the compounds according to the invention may specifically bind to allosteric sites, natural ligand binding sites, or other sites on a GCase. In some embodiments, one or more of the compounds according to the invention that specifically bind the active site of a GCase may also inhibit the activity of a GCase. In alternative embodiments, one or more of the compounds according to the invention may specifically bind a site other than the active site of a GCase. In alternative embodiments, one or more of the compounds according to the invention may specifically bind one isoform of a GCase, for example the human lysosomal GBA1 isoform. In alternative embodiments, one or more of the compounds according to the invention may specifically bind the human lysosomal GBA1 isoform of a GCase over the human non-lysosomal GBA2 isoform and/or the human cytosolic GBA3 isoform. By "specifically binds" is meant a compound that binds a GCase but does not substantially bind other molecules in a sample, such as a lactase, a sucrase, an isomaltase, a glucosylceramide synthase, an alpha-glucosidase II, a glycogen phosphorylase, an acid alpha-glucosidase, a beta-hexosaminidase, an O-GlcNAcase, or another GCase isoform. By "not substantially bind" is meant a binding specificity in the range of about 5-fold to about 100,000-fold, or about 10-fold to about 100,000-fold, or in the range of about 100-fold to about 100,000-fold, or in the range of about 1000-fold to about 100,000-fold, or at least about 5-fold, 10-fold, 20-fold, 50-fold, 100-fold, 200-fold, 500-fold, 1000-fold, 1500-fold, 2000-fold, 2500-fold, 3000-fold, 3500-fold, 4000-fold, 4500-fold, 5000-fold, 6000-fold, 7000-fold, 10,000-fold, 25,000-fold, 50,000-fold, 75,000-fold, or any value within or about the described range, where "binding specificity" means the ratio of the respective binding constants, that is, $Ki_{(other\ molecule)}/Ki_{GCase}$.

In some embodiments, one or more compounds according to the invention may act as a pharmacological chaperone for a GCase. A pharmacological chaperone, as used herein, is a small molecule that may be useful to increase enzyme levels, as in pharmacological chaperone therapy or "PCT".[10,11] In PCT, a small molecule binds to an enzyme, such as a GCase, in the endoplasmic reticulum (ER) or Golgi apparatus (Golgi) and enhances the ability of the enzyme to reach, and/or maintain, its proper fold. Compounds that are pharmacological chaperones may be active-site inhibitors, but may also bind to other sites on the enzyme such as allosteric sites, natural ligand binding sites, or other sites. Without being bound to any particular hypothesis, binding of the chaperone to the enzyme may enhance its trafficking through the secretory pathway to its proper cellular destination, to allow the enzyme to carry out its normal functions. Accordingly, in some embodiments, administration of a compound as described herein, that is a pharmacological chaperone, may increase the lysosomal concentration and/or activity of a GCase. In some embodiments, a compound as described herein, may be used as a pharmacological chaperone to increase deficient or defective levels of a GCase. In alternative embodiments, a compound as described herein, may be used as a pharmacological chaperone to increase wild-type levels of a GCase. In some embodiments, an inhibitor that binds to a GCase may also act as a pharmacological chaperone for a GCase. In some embodiments, an inhibitor that acts as a pharmacological chaperone for a GCase may exhibit transient inhibition of a GCase. In some embodiments, an inhibitor that binds to a GCase and acts as a pharmacological chaperone for a GCase may dissociate from a GCase once the enzyme reaches its proper cellular destination (for example, the lysosomal compartment), so that the enzyme is no longer inhibited and is able to carry out its normal functions. In some embodiments, a compound as described herein, may be used as a pharmacological chaperone to increase the levels of a mutant GCase; in such situations, the mutant GCase in its properly folded state should have sufficient catalytic activity. In some embodiments, the GCase may be a chaperone-responsive mutant mammalian GCase, such as a rat, mouse or human mutant GCase. By a "chaperone-responsive mutant" is meant an enzyme (such as a GCase) bearing a mutation, the effects of which can be ameliorated by a compound that can act as a pharmacological chaperone for that mutant enzyme and thereby increase the concentration and/or activity level of that mutant enzyme. Chaperone-responsive GCase mutations include, without limitation, mutant GCase enzymes bearing mutations as set forth in, for example, SEQ ID NOs: 2, 3, 4, or 5.

In some embodiments, one or more compounds according to the invention may exhibit superior ability to act as a pharmacological chaperone for a GCase. In some embodiments, one or more compounds according to the invention may produce an increased enhancement of a GCase concentration and/or activity level compared to a suitable reference compound that is a pharmacological chaperone for a GCase. By "increased enhancement" means a greater enhancement of a GCase concentration and/or activity level by any value between about 10% and about 90%, or of any value between about 30% and about 60%, or over about 100%, or an increase by about 1-fold, 2-fold, 5-fold, 10-fold or more, in comparison to the enhancement produced by a suitable reference compound that is a pharmacological chaperone for a GCase. In some embodiments, the effective concentration of one or more compounds according to the invention required to enhance a GCase concentration and/or activity level may be lower than the effective concentration for a suitable reference compound that is a pharmacological chaperone for a GCase. By "lower" is meant a compound concentration decreased by any value between about 10% and about 90%, or of any value between about 30% and about 60%, or over about 100%, or a decrease by about 1-fold, 2-fold, 5-fold, 10-fold, 50-fold, 100-fold, or more, in comparison to the effective concentration of a reference compound that is a pharmacological chaperone for a GCase.

In some embodiments, a pharmacological chaperone of a GCase may inhibit the cleavage of glucose from glucosylceramide. In some embodiments, a pharmacological chaperone of a GCase may increase protein levels of a GCase. In some embodiments, a pharmacological chaperone of a GCase may increase enzymatic activity levels of a GCase. In some embodiments, a pharmacological chaperone of a GCase may inhibit aggregation of an alpha-synuclein protein and/or inhibit formation of Lewy bodies. By "inhibit," "inhibition" or "inhibiting" means a decrease by any value between about 10% and about 90%, or of any value between about 30% and about 60%, or over about 100%, or a decrease by about 1-fold, 2-fold, 5-fold, 10-fold or more, in comparison to a reference sample or compound, or in comparison to a wild type GCase. It is to be understood that the inhibiting does not require full inhibition. In some embodiments, the inhibition may be transient. In some embodiments, an inhibitor or modulator, or pharmacological chaperone of a GCase may elevate or enhance GCase protein levels and/or enzymatic activity levels in cells, tissues, or organs (e.g., in brain, liver, spleen, or muscle tissue) and in animals.

In some embodiments, one or more of the compounds of the present invention may be useful as agents that produce a decrease in alpha-synuclein aggregation and Lewy body formation.

In some embodiments, one or more of the compounds of the present invention may elevate GCase protein levels in vivo specifically via interaction with a GCase enzyme, and may be effective in treating conditions which require or respond to enhancement of GCase activity.

By "elevating" or "enhancing" or "increasing" is meant an increase by any value between about 5% and about 90%, or of any value between about 30% and about 60%, or over 100 about %, or an increase by about 1-fold, 2-fold, 5-fold, 10-fold, 15-fold, 25-fold, 50-fold, 100-fold or more, in comparison to a reference sample or compound, or in comparison to a wild type GCase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability ($P_{eff}$) or apparent permeability ($P_{app}$) are reviewed for example by Volpe in The AAPS Journal, 2010, 12(4), 670-678. In some embodiments, one or more of the compounds according to the invention may show enhanced permeability when tested in one or more of these assays for determining $P_{eff}$ or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between about 10% and about 100%, or of any integer value between about 10% and about 100%, for example, about 10%, 20%, 30%, 40%, 50%, 60%, 70%, 80%, 90%, 100%, or over 100%, or an increase by about 1-fold, 2-fold, or 3-fold, or more, as compared to a suitable reference compound such as, for example, (3R,4R,5R)-5-(hydroxymethyl)piperidine-3,4-diol (isofagomine). In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2\times10^{-6}$ cm/s in the assay described below for determination of $P_{app}$ in LLC-PK1 cells. In alternative embodiments, "enhanced permeability" means a $P_{app}$ value in the range $2\times10^{-6}$ cm/s to $40\times10^{-6}$ cm/s in the assay described below for determination of $P_{app}$ in LLC-PK1 cells.

By a "reference compound" or "control" is meant a carbohydrate mimetic iminosugar described in the literature that is a GCase modulator and/or a pharmacological chaperone of a GCase.[9] Examples of reference compounds or controls that are GCase modulators include, without limitation, (3R,4R,5R)-5-(hydroxymethyl)piperidine-3,4-diol (isofagomine), and (1S,6S,7R,8R,8aR)-octahydroindolizine-1,6,7,8-tetraol (castanospermine). Examples of reference compounds or controls that are pharmacological chaperones of a GCase include, without limitation, (3R,4R,5R)-5-(hydroxymethyl)piperidine-3,4-diol (isofagomine), and (1S,6S,7R,8R,8aR)-octahydroindolizine-1,6,7,8-tetraol (castanospermine).

In some embodiments, the invention provides compounds described generally by Formula (I), including any one or more of Formula (Ia)-(If), and the salts, prodrugs, and enantiomeric forms thereof:

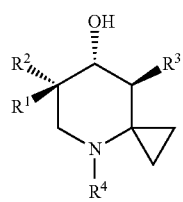

(I)

as set forth in Formula (I): $R^1$ may be OH and $R^2$ may be H or methyl; or $R^1$ may be F and $R^2$ may be H or F; or $R^1$ may be H and $R^2$ may be F; $R^3$ may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$; and $R^4$ may be: H, $C_{1-10}$ alkyl, the $C_{1-10}$ alkyl optionally substituted from one up to the maximum number of substituents with F and/or OH.

In some embodiments, $R^1$ as set forth in Formula (I) may be F or OH. In some embodiments, $R^1$ may be OH. In some embodiments, $R^1$ may be F.

In some embodiments, $R^2$ as set forth in Formula (I) may be H, F, or methyl. In some embodiments, $R^2$ may be H or F. In some embodiments, $R^2$ may be methyl. In some embodiments, $R^2$ may be F. In some embodiments, $R^2$ may be H.

In some embodiments, $R^3$ as set forth in Formula (I) may be: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ may be CN, $CO_2H$, $C(O)NHCH_3$, or $C(O)NH(cyclopropyl)$. In some embodiments, $R^3$ may be: hydroxymethyl, fluoromethyl, difluoromethyl, chloromethyl, methoxymethyl, methoxy, CN, $CO_2H$, $C(O)NHCH_3$, $C(O)NH(cyclopropyl)$, ethynyl, (S)-1-hydroxyethyl, (R)-1-hydroxyethyl, (S)-1-fluoroethyl, (R)-1-fluoroethyl, 2-hydroxypropan-2-yl, 2-fluoropropan-2-yl, 1,1-difluoroethyl, 1-fluoropropyl, (R)-2,2,2-trifluoro-1-hydroxyethyl, (S)-2,2,2-trifluoro-1-hydroxyethyl, methyl, ethyl, propyl, isopropyl, trifluoromethyl, 2-fluoroethyl, 2,2-difluoroethyl, 2,2,2-trifluoroethyl, cyclopropyl, 2,2-difluorocyclopropyl, benzyl, 4-fluorobenzyl, 2-cyclohexyl-1-hydroxyethyl, hydroxy(phenyl)methyl, (4-fluorophenyl)(hydroxy)methyl, (3,5-difluorophenyl)(hydroxy)methyl, hydroxy(p-tolyl)methyl, 2-cyclohexyl-1-fluoroethyl, (3,5-difluorophenyl)fluoromethyl, pyridin-3-ylmethyl, prop-1-yn-1-yl, but-1-yn-1-yl, pent-1-yn-1-yl, 3-hydroxyprop-1-yn-1-yl, 3-fluoroprop-1-yn-1-yl, 3,3-difluoroprop-1-yn-1-yl, 3,3,3-trifluoroprop-1-yn-1-yl, 4-fluorobut-1-yn-1-yl, 4,4-difluorobut-1-yn-1-yl, vinyl, prop-1-en-2-yl, (E)-prop-1-en-1-yl, (Z)-prop-1-en-1-yl, (E)-but-1-en-1-yl, 1-fluorovinyl, (E)-2-fluorovinyl, (Z)-2-fluorovinyl, 2,2-difluorovinyl, 1,2,2-trifluorovinyl, and (E)-3,3,3-trifluoroprop-1-en-1-yl. In some embodiments, $R^3$ may be: methyl, hydroxymethyl, fluoromethyl, difluoromethyl, chloromethyl, methoxymethyl, methoxy, CN, $CO_2H$, $C(O)NHCH_3$, $C(O)NH(cyclopropyl)$, ethyl, propyl, 2-fluoroethyl, 2,2-difluoroethyl, vinyl, (Z)-2-fluorovinyl, (E)-2-fluorovinyl, 2,2-difluorovinyl, ethynyl, prop-1-yn-1-yl, but-1-yn-1-yl, pent-1-yn-1-yl, 3-hydro xyprop-1-yn-1-yl, 3-fluoroprop-1-yn-1-yl, 3,3-difluoroprop-1-yn-1-yl, 4-fluorobut-1-yn-1-yl, and 4,4-difluorobut-1-yn-1-yl. In some embodiments, $R^3$ may be methyl. In some embodiments, $R^3$ may be ethyl. In some embodiments, $R^3$ may be difluoromethyl. In some embodiments, $R^3$ may be ethynyl. In some embodiments, $R^3$ may be prop-1-yn-1-yl.

In some embodiments, $R^4$ as set forth in Formula (I) may be f: H, $C_{1-10}$ alkyl, the $C_{1-10}$ alkyl optionally substituted from one up to the maximum number of substituents with fluoro and/or OH. In some embodiments, $R^4$ may be 2-fluoroethyl, butyl, 5,5,5-trifluoropentyl, 6-hydroxyhexyl, or 5-methylhexyl. In some embodiments, $R^4$ may be methyl. In some embodiments, $R^4$ may be H.

In some embodiments, $R^1$ may be OH; $R^2$ may be H; $R^3$ may be methyl, hydroxymethyl, fluoromethyl, difluoromethyl, chloromethyl, methoxymethyl, methoxy, CN, $CO_2H$, $C(O)NHCH_3$, C(O)NH(cyclopropyl), ethyl, propyl, 2-fluoroethyl, 2,2-difluoroethyl, vinyl, (Z)-2-fluorovinyl, (E)-2-fluorovinyl, 2,2-difluorovinyl, ethynyl, prop-1-yn-1-yl, but-1-yn-1-yl, pent-1-yn-1-yl, 3-hydroxyprop-1-yn-1-yl, 3-fluoroprop-1-yn-1-yl, 3,3-difluoroprop-1-yn-1-yl, 4-fluorobut-1-yn-1-yl, or 4,4-difluorobut-1-yn-1-yl; and $R^4$ may be H.

In some embodiments, $R^1$ may be OH; $R^2$ may be H; $R^3$ may be methyl, ethyl, fluoromethyl, difluoromethyl, ethynyl, or prop-1-yn-1-yl; and $R^4$ may be H.

In some embodiments, $R^1$ may be OH; $R^2$ may be H; $R^3$ may be methyl; and $R^4$ may be H.

In some embodiments, $R^1$ may be OH; $R^2$ may be H; $R^3$ may be ethyl; and $R^4$ may be H.

In some embodiments, $R^1$ may be OH; $R^2$ may be H; $R^3$ may be difluoromethyl; and $R^4$ may be H.

In some embodiments, $R^1$ may be OH; $R^2$ may be H; $R^3$ may be ethynyl; and $R^4$ may be H.

In some embodiments, $R^1$ may be OH; $R^2$ may be H; $R^3$ may be prop-1-yn-1-yl; and $R^4$ may be H.

In specific embodiments of the invention, compounds according to Formula (I) include the compounds described in Table 1.

TABLE 1

| Example | Name | Structure |
|---------|------|-----------|
| 1 | (6R,7R,8S)-8-methyl-4-azaspiro[2.5]octane-6,7-diol | 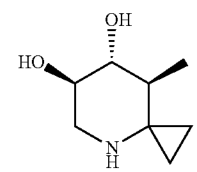 |
| 2 | (6R,7R,8R)-8-(hydroxymethyl)-4-azaspiro[2.5]octane-6,7-diol | 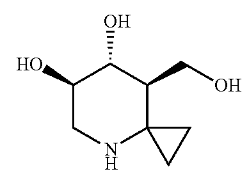 |
| 3 | (6R,7R,8S)-8-(fluoromethyl)-4-azaspiro[2.5]octane-6,7-diol | 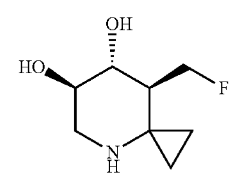 |
| 4 | (6R,7R,8S)-8-(difluoromethyl)-4-azaspiro[2.5]octane-6,7-diol | 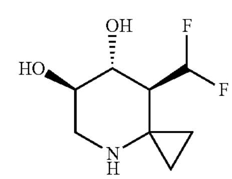 |
| 5 | (6R,7R,8S)-8-(chloromethyl)-4-azaspiro[2.5]octane-6,7-diol | 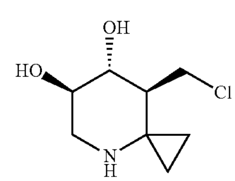 [SMILES: O[C@H]1[C@H](O)CNC2(CC2)[C@@H]1CCl] |
| 6 | (6R,7R,8R)-8-(methoxymethyl)-4-azaspiro[2.5]octane-6,7-diol | 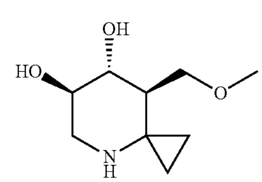 |
| 7 | (6R,7S,8S)-8-methoxy-4-azaspiro[2.5]octane-6,7-diol | 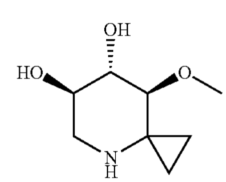 |

TABLE 1-continued

| Example | Name | Structure |
|---------|------|-----------|
| 8 | (6R,7R,8R)-6,7-dihydroxy-4-azaspiro[2.5]octane-8-carbonitrile | 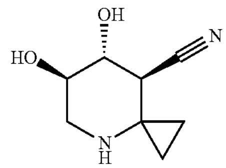 [SMILES: N#C[C@@H]1[C@@H](O)[C@H](O)CNC12CC2] |
| 9 | (6R,7R,8S)-6,7-dihydroxy-4-azaspiro[2.5]octane-8-carboxylic acid | 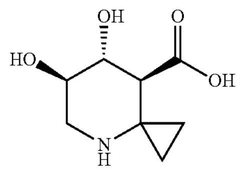 [SMILES: O=C(O)[C@@H]1[C@@H](O)[C@H](O)CNC12CC2] |
| 10 | (6R,7R,8S)-6,7-dihydroxy-N-methyl-4-azaspiro[2.5]octane-8-carboxamide | 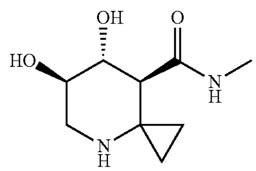 |
| 11 | (6R,7R,8S)-N-cyclopropyl-6,7-dihydroxy-4-azaspiro[2.5]octane-8-carboxamide | 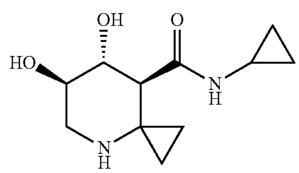 [SMILES: O=C(NC1CC1)[C@@H]1[C@@H](O)[C@H](O)CNC12CC2] |
| 12 | (6R,7R,8S)-8-ethyl-4-azaspiro[2.5]octane-6,7-diol | 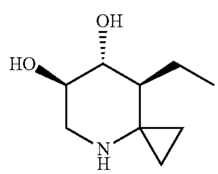 |
| 13 | (6R,7R,8S)-8-propyl-4-azaspiro[2.5]octane-6,7-diol | 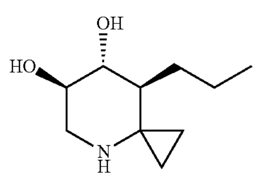 |
| 14 | (6R,7R,8S)-8-(2-fluoroethyl)-4-azaspiro[2.5]octane-6,7-diol | 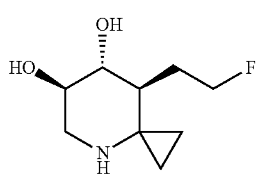 [SMILES: O[C@H]1[C@H](O)CNC2(CC2)[C@@H]1CCF] |
| 15 | (6R,7R,8S)-8-(2,2-difluoroethyl)-4-azaspiro[2.5]octane-6,7-diol | 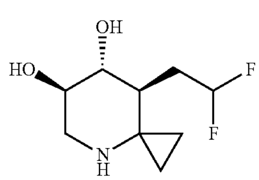 [SMILES: O[C@H]1[C@H](O)CNC2(CC2)[C@@H]1CC(F)F] |
| 16 | (6R,7R,8S)-8-vinyl-4-azaspiro[2.5]octane-6,7-diol | 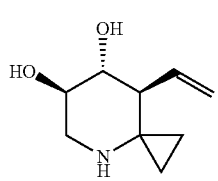 |

TABLE 1-continued

| Example | Name | Structure |
|---|---|---|
| 17 | (6R,7R,8S)-8-((Z)-2-fluorovinyl)-4-azaspiro[2.5]octane-6,7-diol | 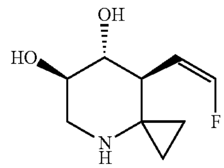 [SMILES: O[C@H]1[C@H](O)CNC2(CC2)[C@@H]1/C=C\F] |
| 18 | (6R,7R,8S)-8-((E)-2-fluorovinyl)-4-azaspiro[2.5]octane-6,7-diol | 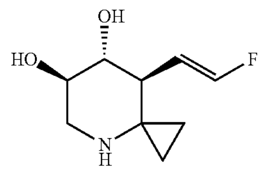 |
| 19 | (6R,7R,8S)-8-(2,2-difluorovinyl)-4-azaspiro[2.5]octane-6,7-diol | 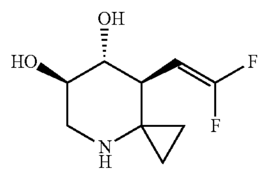 [SMILES: O[C@H]1[C@H](O)CNC2(CC2)[C@@H]1C=C(F)F] |
| 20 | (6R,7R,8S)-8-ethynyl-4-azaspiro[2.5]octane-6,7-diol | 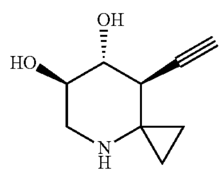 |
| 21 | (6R,7R,8S)-8-(prop-1-yn-1-yl)-4-azaspiro[2.5]octane-6,7-diol | 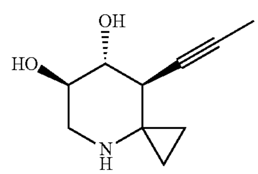 |
| 22 | (6R,7R,8S)-8-(but-1-yn-1-yl)-4-azaspiro[2.5]octane-6,7-diol | 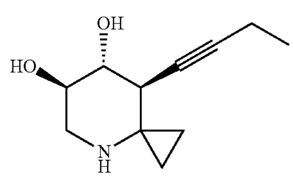 |
| 23 | (6R,7R,8S)-8-(pent-1-yn-1-yl)-4-azaspiro[2.5]octane-6,7-diol | 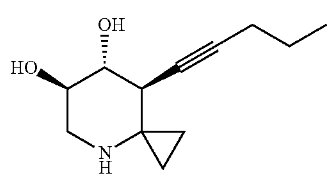 |
| 24 | (6R,7R,8S)-8-(3-hydroxyprop-1-yn-1-yl)-4-azaspiro[2.5]octane-6,7-diol | 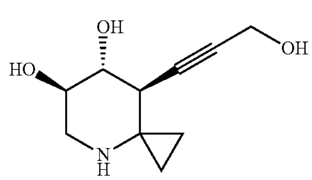 [SMILES: OCC#C[C@@H]1[C@@H](O)[C@H](O)CNC12CC2] |
| 25 | (6R,7R,8S)-8-(3-fluoroprop-1-yn-1-yl)-4-azaspiro[2.5]octane-6,7-diol | 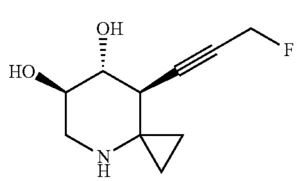 [SMILES: O[C@H]1[C@H](O)CNC2(CC2)[C@@H]1C#CCF] |

TABLE 1-continued

| Example | Name | Structure |
|---|---|---|
| 26 | (6R,7R,8S)-8-(3,3-difluoroprop-1-yn-1-yl)-4-azaspiro[2.5]octane-6,7-diol | 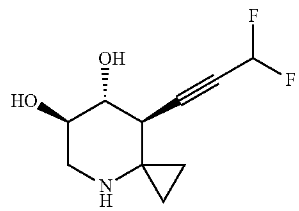 [SMILES: O[C@H]1[C@H](O)CNC2(CC2)[C@@H]1C#CC(F)F] |
| 27 | (6R,7R,8S)-8-(4-fluorobut-1-yn-1-yl)-4-azaspiro[2.5]octane-6,7-diol | 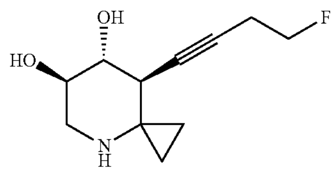 [SMILES: O[C@H]1[C@H](O)CNC2(CC2)[C@@H]1C#CCCF] |
| 28 | (6R,7R,8S)-8-(4,4-difluorobut-1-yn-1-yl)-4-azaspiro[2.5]octane-6,7-diol | 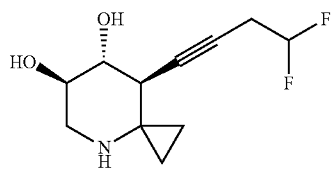 [SMILES: O[C@H]1[C@H](O)CNC2(CC2)[C@@H]1C#CCC(F)F] |
| 29 | (6R,7R,8R)-8-(hydroxymethyl)-4-methyl-4-azaspiro[2.5]octane-6,7-diol | 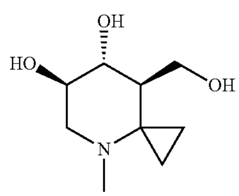 |
| 30 | (6R,7R,8R)-8-((S)-1-hydroxyethyl)-4-azaspiro[2.5]octane-6,7-diol | 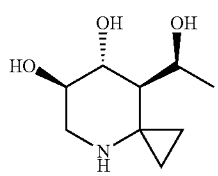 |
| 31 | (6R,7R,8R)-8-((R)-1-hydroxyethyl)-4-azaspiro[2.5]octane-6,7-diol | 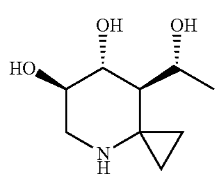 |
| 32 | (6R,7R,8S)-8-((S)-1-fluoroethyl)-4-azaspiro[2.5]octane-6,7-diol | 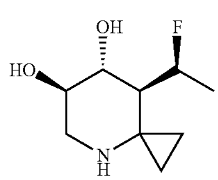 |
| 33 | (6R,7R,8S)-8-((R)-1-fluoroethyl)-4-azaspiro[2.5]octane-6,7-diol | 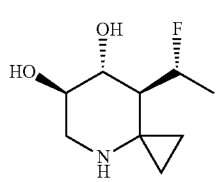 |

TABLE 1-continued

| Example | Name | Structure |
|---|---|---|
| 34 | (6R,7R,8S)-8-(2-hydroxypropan-2-yl)-4-azaspiro[2.5]octane-6,7-diol | 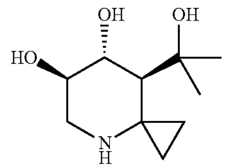 |
| 35 | (6R,7R,8S)-8-(2-fluoropropan-2-yl)-4-azaspiro[2.5]octane-6,7-diol | 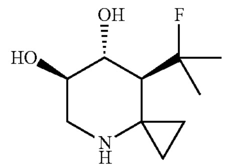 |
| 36 | (6R,7R,8S)-8-(1,1-difluoroethyl)-4-azaspiro[2.5]octane-6,7-diol | 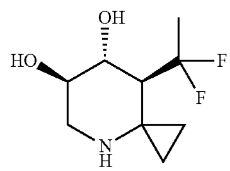 |
| 37 | (6R,7R,8S)-8-((R)-1-fluoropropyl)-4-azaspiro[2.5]octane-6,7-diol | 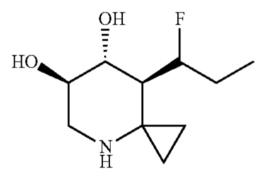 |
| 38 | (6R,7R,8S)-8-((R)-2,2,2-trifluoro-1-hydroxyethyl)-4-azaspiro[2.5]octane-6,7-diol | 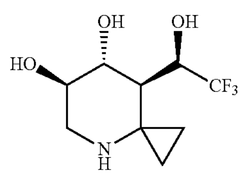 [SMILES: O[C@@H]1[C@@H]([C@@H](O)C(F)(F)F)C2(CC2)NC[C@H]1O] |
| 39 | (6R,7R,8S)-8-((S)-2,2,2-trifluoro-1-hydroxyethyl)-4-azaspiro[2.5]octane-6,7-diol | 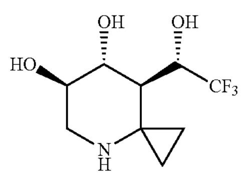 [SMILES: O[C@@H]1[C@@H]([C@H](O)C(F)(F)F)C2(CC2)NC[C@H]1O] |
| 40 | (6R,7R,8S)-8-isopropyl-4-azaspiro[2.5]octane-6,7-diol | 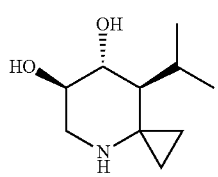 |
| 41 | (6R,7R,8S)-8-(trifluoromethyl)-4-azaspiro[2.5]octane-6,7-diol | 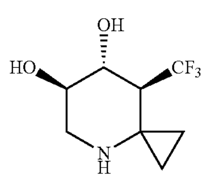 [SMILES: O[C@H]1[C@H](O)CNC2(CC2)[C@@H]1C(F)(F)F] |
| 42 | (6R,7R,8S)-8-(2,2,2-trifluoroethyl)-4-azaspiro[2.5]octane-6,7-diol | 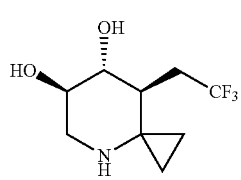 [SMILES: O[C@H]1[C@H](O)CNC2(CC2)[C@@H]1CC(F)(F)F] |

TABLE 1-continued

| Example | Name | Structure |
|---|---|---|
| 43 | (6R,7R,8S)-8-cyclopropyl-4-azaspiro[2.5]octane-6,7-diol | 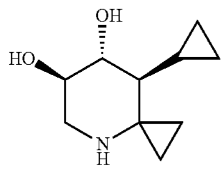 [SMILES: O[C@H]1[C@H](O)CNC2(CC2)[C@@H]1C1CC1] |
| 44 | (6R,7R,8S)-8-((S)-2,2-difluorocyclopropyl)-4-azaspiro[2.5]octane-6,7-diol | 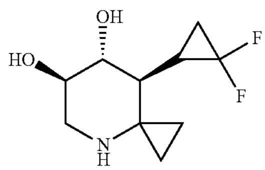 [SMILES: O[C@H]1[C@H](O)CNC2(CC2)[C@@H]1C1CC1(F)F] |
| 45 | (6R,7R,8S)-8-benzyl-4-azaspiro[2.5]octane-6,7-diol | 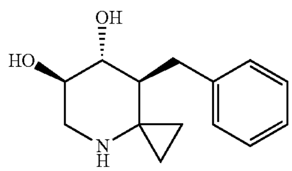 [SMILES: O[C@H]1[C@H](O)CNC2(CC2)[C@@H]1Cc1ccccc1] |
| 46 | (6R,7R,8S)-8-(4-fluorobenzyl)-4-azaspiro[2.5]octane-6,7-diol | 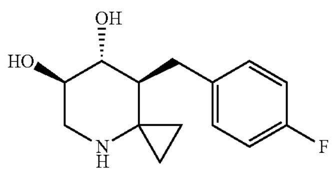 [SMILES: O[C@H]1[C@H](O)CNC2(CC2)[C@@H]1Cc1ccc(F)cc1] |
| 47 | (6R,7R,8R)-8-((R)-2-cyclohex-1-hydroxyethyl)-4-azaspiro[2.5]octane-6,7-diol | 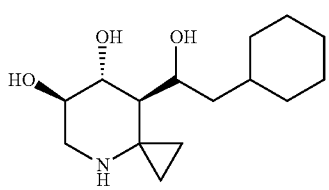 [SMILES: OC(CC1CCCCC1)[C@@H]1[C@@H](O)[C@H](O)CNC12CC2] |
| 48 | (6R,7R,8R)-8-((S)-hydroxy(phenyl)methyl)-4-azaspiro[2.5]octane-6,7-diol | 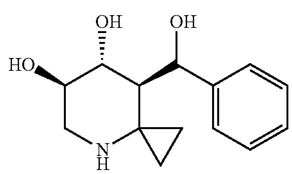 [SMILES: OC(c1ccccc1)[C@@H]1[C@@H](O)[C@H](O)CNC12CC2] |
| 49 | (6R,7R,8R)-8-((S)-(4-fluorophenyl)(hydroxy)methyl)-4-azaspiro[2.5]octane-6,7-diol | 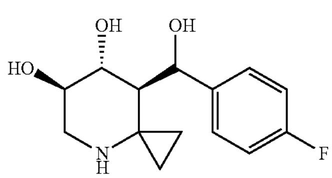 [SMILES: OC(c1ccc(F)cc1)[C@@H]1[C@@H](O)[C@H](O)CNC12CC2] |
| 50 | (6R,7R,8R)-8-((S)-(3,5-difluorophenyl)(hydroxy)methyl)-4-azaspiro[2.5]octane-6,7-diol | 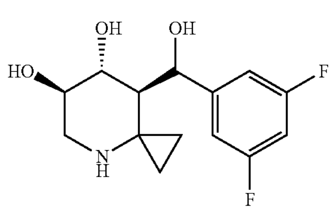 [SMILES: OC(c1cc(F)cc(F)c1)[C@@H]1[C@@H](O)[C@H](O)CNC12CC2] |

TABLE 1-continued

| Example | Name | Structure |
|---|---|---|
| 51 | (6R,7R,8R)-8-((S)-hydroxy(p-tolyl)methyl)-4-azaspiro[2.5]octane-6,7-diol | 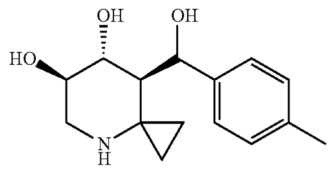 [SMILES: Cc1ccc(C(O)[C@@H]2[C@@H](O)[C@H](O)CNC23CC3)cc1] |
| 52 | (6R,7R,8S)-8-((R)-2-cyclohexyl-1-fluoroethyl)-4-azaspiro[2.5]octane-6,7-diol | 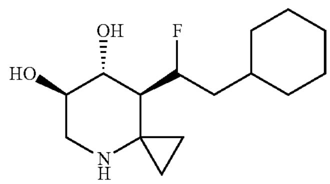 [SMILES: O[C@H]1[C@H](O)CNC2(CC2)[C@@H]1C(F)CC1CCCCC1] |
| 53 | (6R,7R,8S)-8-((S)-(3,5-difluorophenyl)fluoromethyl)-4-azaspiro[2.5]octane-6,7-diol | 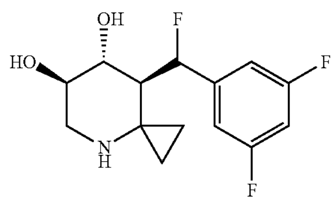 [SMILES: O[C@H]1[C@H](O)CNC2(CC2)[C@@H]1C(F)c1cc(F)cc(F)c1] |
| 54 | (6R,7R,8R)-6-fluoro-8-(hydroxymethyl)-4-azaspiro[2.5]octan-7-ol | 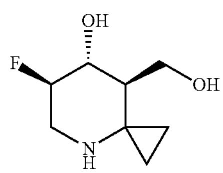 |
| 55 | (6S,7R,8R)-6-fluoro-8-(hydroxymethyl)-4-azaspiro[2.5]octan-7-ol | 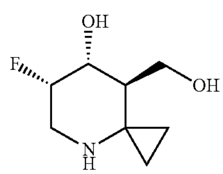 |
| 56 | (6R,7R,8R)-8-(hydroxymethyl)-6-methyl-4-azaspiro[2.5]octane-6,7-diol | 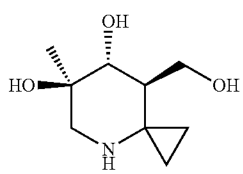 |
| 57 | (7R,8R)-6,6-difluoro-8-(hydroxymethyl)-4-azaspiro[2.5]octan-7-ol | 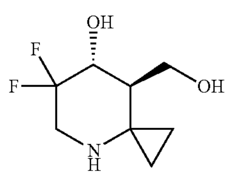 [SMILES: OC[C@@H]1[C@@H](O)C(F)(F)CNC12CC2] |
| 58 | (6R,7R,8S)-6-fluoro-8-(fluoromethyl)-4-azaspiro[2.5]octan-7-ol | 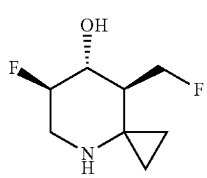 [SMILES: O[C@H]1[C@H](F)CNC2(CC2)[C@@H]1CF] |

TABLE 1-continued

| Example | Name | Structure |
|---|---|---|
| 59 | (6R,7R,8S)-8-(difluoromethyl)-6-fluoro-4-azaspiro[2.5]octan-7-ol | 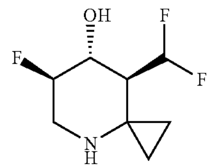 [SMILES: O[C@H]1[C@H](F)CNC2(CC2)[C@@H]1C(F)F] |
| 60 | (6S,7R,8S)-6-fluoro-8-(fluoromethyl)-4-azaspiro[2.5]octan-7-ol | 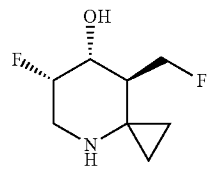 [SMILES: O[C@@H]1[C@@H](CF)C2(CC2)NC[C@@H]1F] |
| 61 | (6S,7R,8S)-8-(difluoromethyl)-6-fluoro-4-azaspiro[2.5]octan-7-ol | 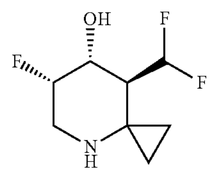 [SMILES: O[C@@H]1[C@@H](C(F)F)C2(CC2)NC[C@@H]1F] |
| 62 | (6R,7R,8S)-8-(pyridin-3-ylmethyl)-4-azaspiro[2.5]octane-6,7-diol | 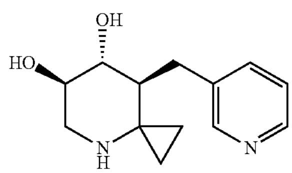 [SMILES: O[C@H]1[C@H](O)CNC2(CC2)[C@@H]1Cc1cccnc1] |
| 63 | (6R,7R,8S)-8-(difluoromethyl)-4-methyl-4-azaspiro[2.5]octane-6,7-diol | 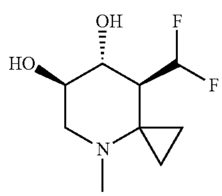 |
| 64 | (6R,7R,8S)-8-(difluoromethyl)-4-(2-fluoroethyl)-4-azaspiro[2.5]octane-6,7-diol | 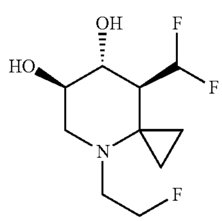 [SMILES: O[C@H]1[C@H](O)CN(CCF)C2(CC2)[C@@H]1C(F)F] |
| 65 | (6R,7R,8S)-4-butyl-8-(fluoromethyl)-4-azaspiro[2.5]octane-6,7-diol | 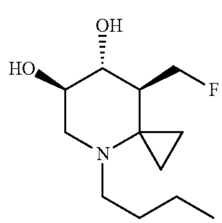 [SMILES: CCCCN1C[C@@H](O)[C@H](O)[C@@H](CF)C12CC2] |
| 66 | (6R,7R,8S)-8-(difluoromethyl)-4-(5,5,5-trifluoropentyl)-4-azaspiro[2.5]octane-6,7-diol | 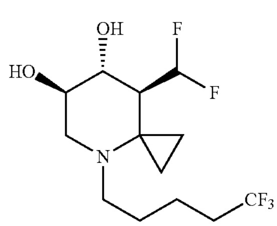 [SMILES: O[C@H]1[C@H](O)CN(CCCCC(F)(F)F)C2(CC2)[C@@H]1C(F)F] |

TABLE 1-continued

| Example | Name | Structure |
|---|---|---|
| 67 | (6R,7R,8S)-8-(difluoromethyl)-4-(6-hydroxyhexyl)-4-azaspiro[2.5]octane-6,7-diol | 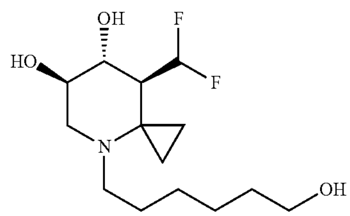 [SMILES: OCCCCCCN1C[C@@H](O)[C@H](O)[C@@H](C(F)F)C12CC2] |
| 68 | (6R,7R,8S)-8-(difluoromethyl)-4-(5-methylhexyl)-4-azaspiro[2.5]octane-6,7-diol | 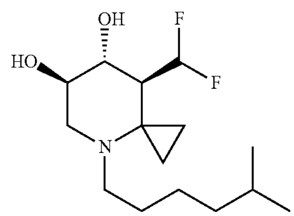 [SMILES: CC(C)CCCCN1C[C@@H](O)[C@H](O)[C@@H](C(F)F)C12CC2] |
| 69 | (6R,7R,8S)-8-(3,3,3-trifluoroprop-1-yn-1-yl)-azaspiro-[2.5]octane-6,7-diol | 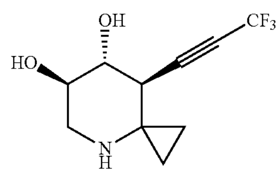 [SMILES: O[C@H]1[C@H](O)CNC2(CC2)[C@@H]1C#CC(F)(F)F] |
| 70 | (6R,7R,8S)-8-(prop-1-en-2-yl)-4-azaspiro[2.5]octane-6,7-diol | 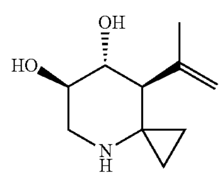 |
| 71 | (6R,7R,8S)-8-((E)-prop-1-en-1-yl)-4-azaspiro[2.5]octane-6,7-diol | 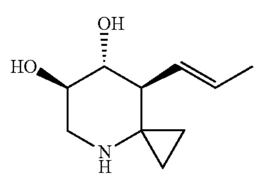 |
| 72 | (6R,7R,8S)-8-((Z)-prop-1-en-1-yl)-4-azaspiro[2.5]octane-6,7-diol | 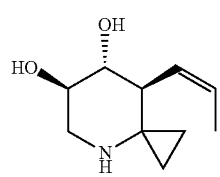 |
| 73 | (6R,7R,8S)-8-((E)-but-1-en-1-yl)-4-azaspiro[2.5]octane-6,7-diol | 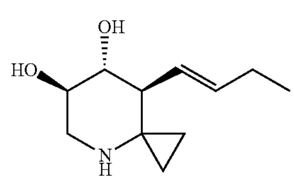 |
| 74 | (6R,7R,8S)-8-(1-fluorovinyl)-4-azaspiro[2.5]octane-6,7-diol | 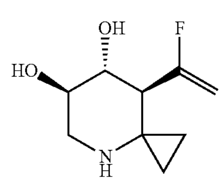 |

TABLE 1-continued

| Example | Name | Structure |
|---|---|---|
| 75 | (6R,7R,8S)-8-(1,2,2-trifluorovinyl)-4-azaspiro[2.5]octane-6,7-diol | 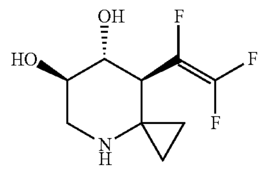 [SMILES: O[C@H]1[C@H](O)CNC2(CC2)[C@@H]1C(F)=C(F)F] |
| 76 | (6R,7R,8S)-8-((E)-3,3,3-trifluoroprop-1-en-1-yl)-4-azaspiro[2.5]octane-6,7-diol | 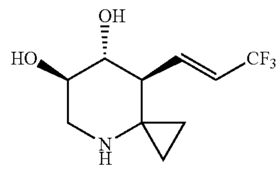 [SMILES: O[C@H]1[C@H](O)CNC2(CC2)[C@@H]1/C=C/C(F)(F)F] |

As will be appreciated by a person skilled in the art, Formula (I) above may also be represented alternatively as follows:

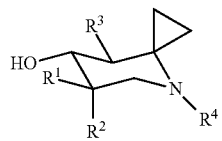

as used herein the singular forms "a", "and", and "the" include plural referents unless the context clearly dictates otherwise. For example, "a compound" refers to one or more of such compounds, while "the enzyme" includes a particular enzyme as well as other family member equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond. In alternative embodiments, the alkenyl group may contain from two to eight carbon atoms, such as 2, 3, 4, 5, 6, 7, or 8 carbon atoms. In alternative embodiments, the alkenyl group may contain from three to six carbon atoms, such as 3, 4, 5, or 6 carbon atoms. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms, such as 2, 3, 4, 5, 6, 7, 8, 9, or 10 carbon atoms, and which is attached to the rest of the molecule by a single bond. In alternative embodiments, the alkynyl group may contain from two to eight carbon atoms, such as 2, 3, 4, 5, 6, 7, or 8 carbon atoms. In alternative embodiments, the alkynyl group may contain from three to six carbon atoms, such as 3, 4, 5, or 6 carbon atoms. Unless stated otherwise specifically in the specification, the alkynyl group may be optionally substituted by one or more substituents as described herein.

"Aryl" refers to a mono- or bicyclic aromatic ring containing only carbon atoms, including for example, 6-14 members, such as 6, 7, 8, 9, 10, 11, 12, 13, or 14 members. Examples of aryl groups include phenyl, biphenyl, naphthyl, indanyl, indenyl, tetrahydronaphthyl, 2,3-dihydrobenzofuranyl, dihydrobenzopyranyl, 1,4-benzodioxanyl, and the like. Unless stated otherwise specifically herein, the term "aryl"

is meant to include aryl groups optionally substituted by one or more substituents as described herein.

"Heteroaryl" refers to a single or fused aromatic ring group containing one or more heteroatoms in the ring, for example N, O, S, including for example, 5-14 members, such as 5, 6, 7, 8, 9, 10, 11, 12, 13, or 14 members. Examples of heteroaryl groups include furan, thiophene, pyrrole, oxazole, thiazole, imidazole, pyrazole, isoxazole, isothiazole, 1,2,3-oxadiazole, 1,2,3-triazole, 1,2,4-triazole, 1,3,4-thiadiazole, tetrazole, pyridine, pyridazine, pyrimidine, pyrazine, 1,3,5-triazine, imidazole, benzimidazole, benzoxazole, benzothiazole, indolizine, indole, isoindole, benzofuran, benzothiophene, 1H-indazole, purine, 4H-quinolizine, quinoline, isoquinoline, cinnoline, phthalazine, quinazoline, quinoxaline, 1,8-naphthyridine, pteridine, and the like. Unless stated otherwise specifically herein, the term "heteroaryl" is meant to include heteroaryl groups optionally substituted by one or more substituents as described herein.

"Arylalkyl" refers to a group of the formula —$R_aR^b$ where $R_a$ is a $C_{1-10}$ alkyl group as described herein and Rb is one or more aryl moieties as described herein. The arylalkyl group(s) may be optionally substituted as described herein.

"Heteroarylalkyl" refers to a group of the formula —$R_aR_e$ where $R_a$ is a $C_{1-10}$ alkyl group as described herein and $R_c$ is one or more heteroaryl moieties as described herein. The heteroarylalkyl group(s) may be optionally substituted as described herein.

"Alkoxyalkyl" refers to a group of the formula —$R_aOR_a$, where each $R_a$ is independently a $C_{1-10}$ alkyl or a $C_{1-6}$ alkyl or a $C_{1-5}$ alkyl group as described herein. The alkoxyalkyl group(s) may be optionally substituted as described herein.

"Alkoxy" refers to a group of the formula —$OR_a$, where each $R_a$ is independently a $C_{1-10}$ alkyl or a $C_{1-6}$ alkyl or a $C_{1-5}$ alkyl group as described herein. The alkoxy group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. In alternative embodiments, the cycloalkyl group may contain from three to six carbon atoms, such as 3, 4, 5, or 6 carbon atoms. Unless otherwise stated specifically herein, the term "cycloalkyl" is meant to include cycloalkyl groups which are optionally substituted as described herein.

"Cycloalkylalkyl" refers to a group of the formula —$R_aR_d$, where $R_a$ is a $C_{1-10}$ alkyl or a $C_{1-6}$ alkyl group as described herein and Rd is a $C_{3-8}$ cycloalkyl group as described herein. The cycloalkylalkyl group(s) may be optionally substituted as described herein.

"Cycloalkylmethyl" refers to a group of the formula —$CH_2R_d$, where Rd is a $C_{3-8}$ cycloalkyl group as described herein. The cycloalkylmethyl group(s) may be optionally substituted as described herein.

"Halo" refers to bromo, chloro, fluoro, iodo, etc. In some embodiments, suitable halogens include fluorine or chlorine.

"Optional" or "optionally" means that the subsequently described event of circumstances may or may not occur, and that the description includes instances where the event or circumstance occurs one or more times and instances in which it does not. For example, "optionally substituted alkyl" means that the alkyl group may or may not be substituted and that the description includes both substituted alkyl groups and alkyl groups having no substitution, and that the alkyl groups may be substituted one or more times. Examples of optionally substituted alkyl groups include, without limitation, methyl, ethyl, propyl, butyl, pentyl, hexyl, isopropyl, isobutyl, sec-butyl, tert-butyl, etc. Examples of suitable optional substituents include, without limitation, H, F, Cl, $CH_3$, OH, $OCH_3$, $CF_3$, $CHF_2$, $CH_2F$, CN, halo, and $C_{1-10}$ alkoxy.

Therapeutic Indications

The invention provides, in part, methods of treating conditions that are modulated, directly or indirectly, by a GCase enzyme or by GCase protein levels or GCase activity levels, for example, a condition that is benefited by modulating a GCase enzyme or by an elevation of GCase protein levels or by an elevation of GCase enzyme activity levels. Such conditions may include, without limitation, neurodegenerative diseases, such as Parkinson's disease (PD), synucleopathies, and lysosomal storage diseases, such as Gaucher's disease. Thus, one or more of the compounds of the invention may be used to treat a subject at risk for developing, or already diagnosed with, various neurodegenerative or other diseases. In alternative embodiments, one or more of the compounds of the invention may be used to treat a subject carrying a chaperone-responsive GCase mutation. The term "treating" as used herein includes treatment, prevention, and amelioration.

In alternative embodiments, one or more of the compounds of the invention may also be useful in the treatment of diseases or disorders related to deficiency or over-expression of GCase or accumulation or depletion of glucosylceramide, or any disease or disorder responsive to glycosidase modulator therapy, glycosidase inhibition therapy or glycosidase pharmacological chaperone therapy. Such diseases and disorders may include, but are not limited to, neurodegenerative diseases, such as Parkinson's disease (PD), synucleopathies, and lysosomal storage diseases, such as Gaucher's disease. Such diseases and disorders may also include diseases or disorders related to the accumulation or deficiency in the enzyme glucosylceramide synthase. Also included is a method of protecting or treating target cells expressing GCase, the dysregulation of which may result in disease or pathology.

In alternative embodiments, the invention provides methods of enhancing or elevating levels of GCase protein and/or GCase enzyme activity levels in animal subjects, such as, veterinary and human subjects. This elevation of GCase protein and/or activity levels may be useful for the prevention or treatment of Parkinson's disease; prevention or treatment of other neurodegenerative diseases (e.g. Alzheimer's disease, Pick's disease); providing neuroprotective effects; preventing damage to dopaminergic neurons; and treating diseases associated with genetic deficiency of GCase, such as Gaucher's disease.

In alternative embodiments, the invention provides methods of inhibiting and/or modulating a GCase enzyme in animal subjects, such as veterinary and human subjects.

In alternative embodiments, the invention provides methods of chaperoning a GCase enzyme in animal subjects, such as, veterinary and human subjects.

In alternative embodiments, the invention provides methods of inhibiting aggregation of alpha-synuclein protein, or inhibiting formation of Lewy bodies, in animal subjects, such as, veterinary and human subjects. Disease states of interest may include Parkinson's disease (PD) and related neurodegenerative synucleopathies, in which abnormal aggregation of the alpha-synuclein protein is involved in disease pathogenesis. In some embodiments, a compound according to the invention may be used to block aggregation of alpha-synuclein protein by maintaining elevated protein levels of GCase and/or elevated GCase enzyme activity levels, thereby providing therapeutic benefit.

Neurodegenerative diseases that may be treated with a compound of the invention include, without limitation: Parkinson's disease, Dementia with Lewy bodies, Multiple system atrophy, Pick's disease (PiD), Corticobasal degeneration (CBD), Alzheimer's disease, Amyotrophic lateral sclerosis (ALS), Amyotrophic lateral sclerosis with cognitive impairment (ALSci), Argyrophilic grain dementia, Bluit disease, Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Myotonic dystrophy, Multi-infarct dementia, Niemann-Pick disease (type C), Pallido-ponto-nigral degeneration, Parkinsonism-dementia complex of Guam, Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Schizophrenia, Mild Cognitive Impairment (MCI), Neuropathy (including peripheral neuropathy, autonomic neuropathy, neuritis, and diabetic neuropathy), or Glaucoma.

Lysosomal storage diseases that may be treated with a compound of the invention may include, without limitation: Gaucher's disease, including Type I (non-neuronopathic), Type II (acute infantile neuronopathic), and Type III (chronic neuronopathic) Gaucher's disease.

In some embodiments, a compound according to the invention may be useful in the treatment of a disorder in which the regulation of GCase protein levels and/or enzyme activity levels are implicated, or any condition as described herein.

Other conditions that may be treated using one or more of the compounds according the invention are those triggered, affected, or in any other way correlated with levels of GCase protein or GCase enzyme activity. It is expected that one or more of the compounds of this invention may be useful for the treatment of such conditions and in particular, but not limited to, Parkinson's disease and Gaucher's disease.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I), including any one or more of Formula (Ia)-(If), are provided.

The compounds of Formula (I), including any one or more of Formula (Ia)-(If), and their pharmaceutically acceptable salts, enantiomers, solvates, and derivatives may be useful because they may have pharmacological activity in animals, including humans. In some embodiments, one or more of the compounds according to the invention may be stable in plasma, when administered to a subject, such as a human.

In general, a compound according to the invention may be administered to a subject in need thereof, or by contacting a cell or a sample, for example, a pharmaceutical composition comprising a therapeutically effective amount of the compound according to Formula (I), including any one or more of Formula (Ia)-(If).

In some embodiments, a compound according to the invention, or for use according to the invention, may be provided in combination with any other active agents or pharmaceutical compositions where such combined therapy may be useful to modulate GCase protein and/or activity levels, for example, to treat neurodegenerative, or lysosomal storage diseases, or any condition described herein. In some embodiments, a compound according to the invention, or for use according to the invention, may be provided in combination with one or more agents useful in the prevention or treatment of Parkinson's disease. Examples of such agents may include, without limitation, Levodopa (L-DOPA);
A peripheral DOPA decarboxylase inhibitor (DDCI), such as Carbidopa (Lodosyn®);
Combined carbidopa/levodopa (Kinson®, Sinemet®, Parcopa®, Atamet®);
Combined carbidopa/levodopa/entacapone (Stalevo®);
Amantadine (Symmetrel®);
Dopamine antagonists, such as bromocriptine (Cycloset®, Parlodel®), pergolide (Permax®), pramipexole (Mirapexin®, Sifrol®, Mirapex®), ropinirole (Ronirol®, Adartrel®, Requip®), piribedil (Trivastal Retard®, Trastal®, Trivastan®, Clarium®, Pronoran®), cabergoline (Cabaser®, Dostinex®), apomorphine (Ixense®, Spontane®, Uprima®, Apokyn®), Lisuride® (Dopergin®, Proclacam®, Revanil®), rotigotine (Neupro®), Ciladopa® (AY-27,110), Dihydrexidine® (DAR-0100), Dinapsoline®, Doxanthrine®, epicriptine (beta-dihydroergocryptine), N-n-propylnorapomorphine (NPA), quinagolide (Norprolac®), Roxindole® (EMD-49,980), Sumanirole® (PNU-95,666), pardoprunox, aplindore, etc.;
Monoamine oxidase-B (MAO-B) inhibitors, such as selegiline (Anipryl®, L-Deprenyl®, Eldepryl®, Emsam®, Zelapar®) rasagiline (Azilect®, AGN 1135), safinamide, etc.;
Anticholinergics, such as benzatropine (benztropine, Cogentin®), diphenhydramine (Benadryl®, Dimedrol®, Daedalon®, Nytol®), orphenadrine (Norflex®, Mephenamin®, Disipal®, Banflex®, Flexon®, Biorphen®, Brocasipal®, Dolan®, Norgesic®, OrfenAce®), trihexyphenidyl (Artane®, Apo-Trihex®, Parkin®, Pacitane®, benzhexol, trihex), etc.;
Catechol-O-methyl transferase (COMT) inhibitors, such as entacapone (COMTan®), tolcapone (Tasmar®), nitecapone, nebicapone, etc.;
Adenosine $A_{2A}$ receptor antagonists, such as istradefylline (KW-6002), preladenant, fipamezole (JP-1730), SCH-420814, BIIA-014, Lu AA4707, etc.;
Metabotropic glutamate receptor 5 (mgluR5) modulators, such as dipraglurant, etc.;
AMPA receptor antagonists, such as perampanel (Fycompa®), etc.;
Anticonvulsants, such as zonisamide (Tremode®), etc.;
Nicotinic acetylcholine receptor (nAChR) agonists, such as nicotine, ABT-418, WAY-317,538 (SEN-12333), EVP-6124, MEM 3454, Nefiracetam, etc.
Acetylcholine esterase inhibitors (AChEIs) such as Aricept® (Donepezil), Exelon® (Rivastigmine), Razadyne® (Razadyne ER®, Reminyl®, Nivalin®, galantamine), Cognex® (Tacrine), Huperzine A, Phenserine, Debio-9902 SR (ZT-1 SR), Zanapezil (TAK0147), ganstigmine, NP7557, etc.;
Atypical antipsychotics, such as clozapine, etc.; and
Modafinil (Alertec®, Modavigil®, Provigil®).

It is to be understood that combination of compounds according to the invention, or for use according to the invention, with Parkinson's agents is not limited to the examples described herein, but may include combination with any agent useful for the treatment of Parkinson's disease. Combination of compounds according to the invention, or for use according to the invention, and other Parkinson's agents may be administered separately or in conjunction. The administration of one agent may be prior to, concurrent to, or subsequent to the administration of other agent(s).

In some embodiments, a compound according to the invention, or for use according to the invention, may be provided in combination with one or more agents useful in the prevention or treatment of Gaucher's disease. Examples of such agents may include, without limitation, Recombinant human GCase enzyme replacement therapy, such as imiglucerase (Cerezyme®), velaglucerase alfa (VPRIV®), taliglucerase alfa (Elelyso®), etc.;

Glucosylceramide synthase inhibitors, such as N-butyl-deoxynojirimycin (Zavesca®, miglustat), EXEL-0346, Genz-123346, Eliglustat® (Genz-112638), etc.;

Bisphosphonates, such as zoledronate (Zometa®, Zomera®, Aclasta®, Reclast®), alendronate sodium (Fosamax®), etidronate (Didronel®), clodronate (Bonefos®, Loron®), tiludronate (Skelid®), pamidronate (APD®, Aredia®), neridronate (Nerixia®), olpadronate, ibandronate (Boniva®), risedronate (Actonel®), etc.;

Antiepileptics, such as Tegretol® (Carbatrol®, carbamazepine), Zarontin® (ethosuximide), Felbatol® (felbamate), Gabitril® (tiagabine), Keppra® (levetiracetam), Lamictal® (lamotrigine), Lyrica® (pregabalin), Neurontin® (gabapentin), Dilantin® (phenytoin), Topamax® (topiramate), Trileptal® (oxcarbazepine), Depakene® (Depakote®, valproate, valproic acid), Zonegran® (zonisamide), Valium® (diazepam), Ativan® (lorazepam) Klonopin® (clonazepam), Fycompa® (perampanel), Oxtellar XR® (oxcarbazepine), etc.; and Gene therapy.

It is to be understood that combination of compounds according to the invention, or for use according to the invention, with Gaucher's agents is not limited to the examples described herein, but may include combination with any agent useful for the treatment of Gaucher's disease. Combination of compounds according to the invention, or for use according to the invention, and other Gaucher's agents may be administered separately or in conjunction. The administration of one agent may be prior to, concurrent to, or subsequent to the administration of other agent(s).

In alternative embodiments, a compound may be supplied as a "prodrug" or protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but may be converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987.

Suitable prodrug forms of one or more of the compounds of the invention may include embodiments in which one or more OH groups as set forth in Formula (I), including any one or more of Formula (Ia)-(If), may be protected as OC(O)R, where R may be optionally substituted alkyl, alkenyl, alkynyl, aryl, or heteroaryl. In these cases the ester groups may be hydrolyzed in vivo (e.g. in bodily fluids), liberating the OH groups and releasing the active compounds. Preferred prodrug embodiments of the invention may include compounds of Formula (I), including any one or more of Formula (Ia)-(If), where one or more OH groups may be protected with acetate, for example as $OC(O)CH_3$.

Compounds according to the invention, or for use according to the invention, may be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, sub acetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require modulation of GCase activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition and/or modulating of a GCase, elevation of GCase protein and/or enzyme activity levels, inhibition of alpha-synuclein aggregation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition and/or modulating of a GCase, elevation of GCase protein and/or enzyme activity levels, inhibition of alpha-synuclein aggregation, or any condition described herein. Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 μM or 0.01 nM-10 μM.

In alternative embodiments, in the treatment or prevention of conditions which may require modulation of GCase activity, an appropriate dosage level may generally be about 0.01 to 500 mg per kg subject body weight per day, and may be administered in singe or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formula (I), including any one or more of Formula (Ia)-(If), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I), including any one or more of Formula (Ia)-(If). For example, different isotopic forms of hydrogen (H) include protium ($^1$H), deuterium ($^2$H) and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I), including any one or more of Formula (Ia)-(If), may be prepared without undue experimentation by conventional techniques well known to those skilled in the art or by processes analogous to those described in the Schemes and Examples herein using appropriate isotopically-enriched reagents and/or intermediates.

Other Uses

In alternative embodiments, one or more of the compounds of the invention may be used in studying the physiological role of GCase at the cellular and organismal level. In some embodiments, one or more of the compounds may be useful in the development of animal models for studying diseases or disorders that may be related to deficiencies in GCase, over-expression of GCase, accumulation of glucosylceramide, depletion of glucosylceramide, and for studying treatment of diseases and disorders that may be related to deficiency or over-expression of GCase, or accumulation or depletion of glucosylceramide. Such diseases and disorders may include neurodegenerative diseases, including Parkinson's disease, and lysosomal storage diseases, including Gaucher's disease.

The effectiveness of a compound in treating pathology associated with the accumulation of toxic alpha-synuclein species (for example, Parkinson's disease and other synucleopathies) may be confirmed by testing the ability of a compound to block the formation of toxic alpha-synuclein species in established cellular' and/or transgenic animal models of disease.[13]

The effectiveness of a compound in treating pathology associated with a genetic deficiency of GCase (for example, Gaucher's disease) may be confirmed by testing the ability of a compound to increase levels of GCase protein and/or GCase enzyme activity in fibroblasts derived from Gaucher patients,[14] or in established cellular[15] and/or transgenic animal models of disease.[14,16] Gaucher fibroblast cell lines homozygous for loss of function GBA1 mutations may be obtained from, for example, the Coriell Institute for Medical Research.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations
AIBN=azobisisobutyronitrile
9-BBN=9-borabicyclo[3.3.1]nonane
Boc$_2$O=di-tert-butyl dicarbonate
CAN=ceric ammonium nitrate
DAST=diethylaminosulfur trifluoride
DBU=1,8-diazabicyclo[5.4.0]undec-7-ene
DCM=dichloromethane
DIAD=diisopropyl azodicarboxylate
DIBAL-H=diisobutylaluminium hydride
DIPEA=diisopropylethylamine
DMF=N,N-dimethylformamide
DMP=Dess-Martin periodinane
Et$_2$O=diethyl ether
HATU=(1-[bis(dimethylamino)methylene]-1H-1,2,3-triazolo[4,5-b]pyridinium 3-oxid hexafluorophosphate)
HOBt=hydroxybenzotriazole
MsCl=methanesulfonyl chloride
TFA=2,2,2-trifluoroacetic acid
TFAA=trifluoroacetic acid anhydride
Tf$_2$O=trifluoromethanesulfonic anhydride
THF=tetrahydrofuran
thio-CDI=1,1'-thiocarbonyldiimidazole
TMSCF$_3$=trifluoromethyltrimethylsilane
TsOH=p-toluenesulfonic acid General Procedures and Intermediates The compounds of the invention are synthesized according to standard schemes and procedures, as indicated in, for example, Schemes 1 to 18, as appropriate. Intermediate A (Scheme 1) may be prepared as described in, for example, Example 2.

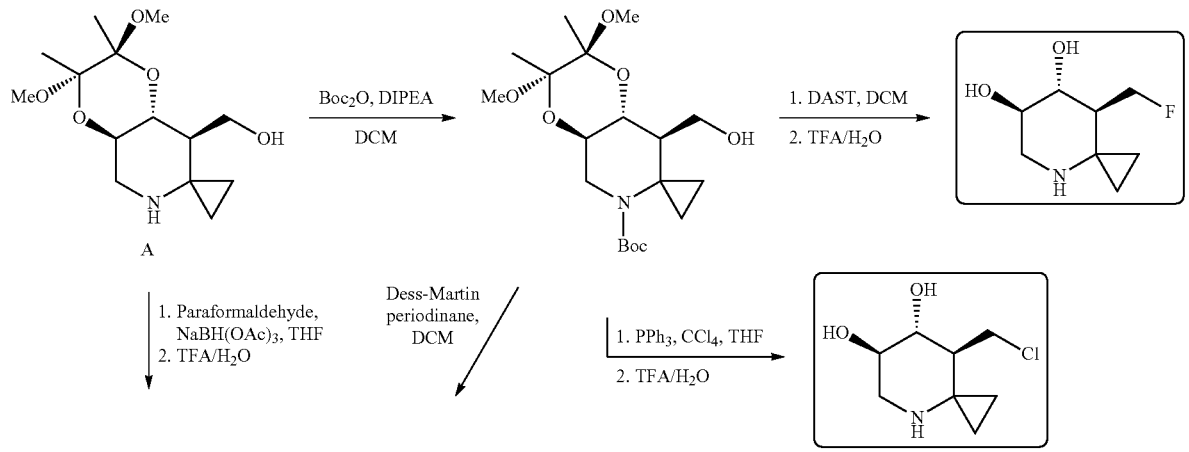

Scheme 1

-continued
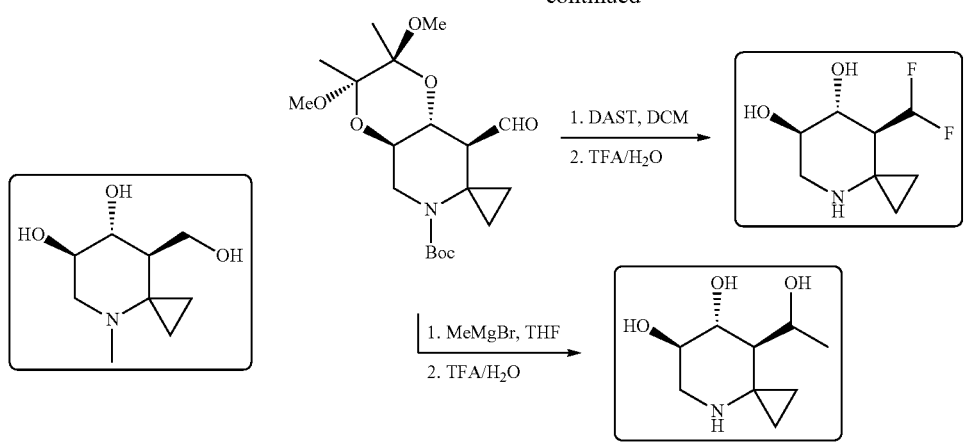
Scheme 2
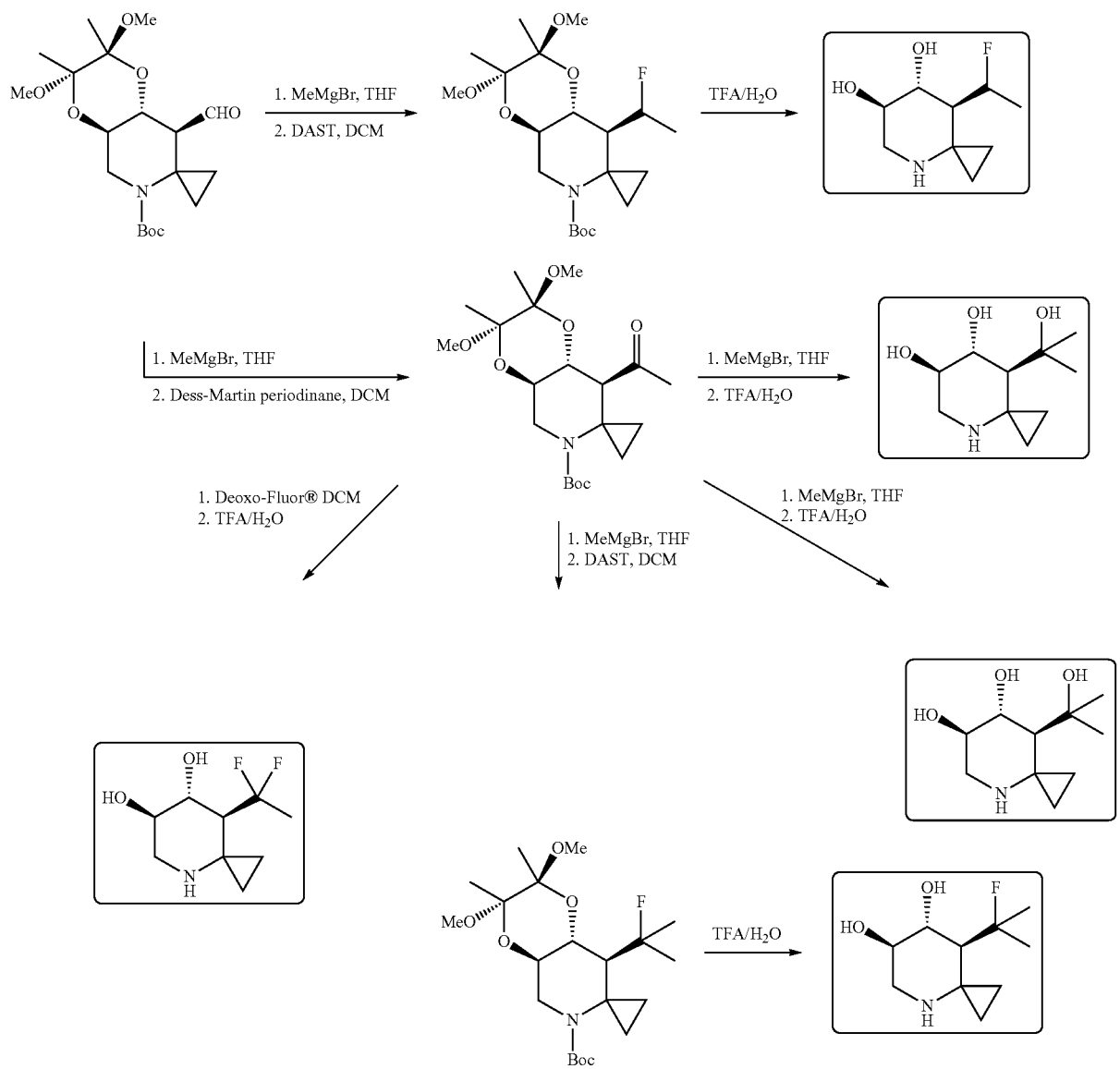

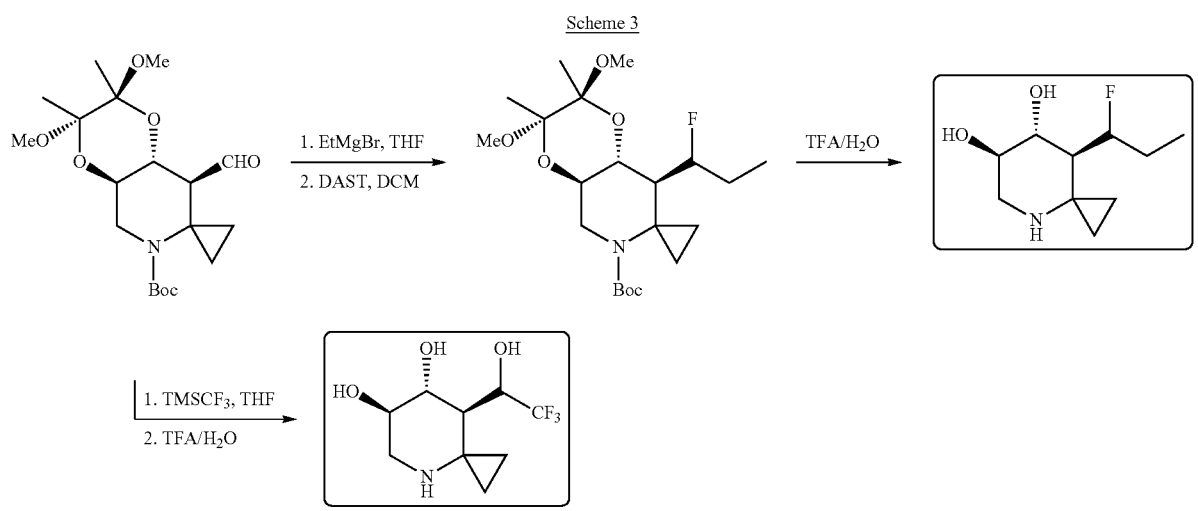 [SMILES: CO[C@@]1(C)O[C@@H]2[C@@H](C=O)C3(CC3)N(C(=O)OC(C)(C)C)C[C@H]2O[C@]1(C)OC ; CCC(F)[C@@H]1[C@H]2O[C@](C)(OC)[C@@](C)(OC)O[C@@H]2CN(C(=O)OC(C)(C)C)C12CC2 ; CCC(F)[C@@H]1[C@@H](O)[C@H](O)CNC12CC2 ; OC([C@@H]1[C@@H](O)[C@H](O)CNC12CC2)C(F)(F)F]
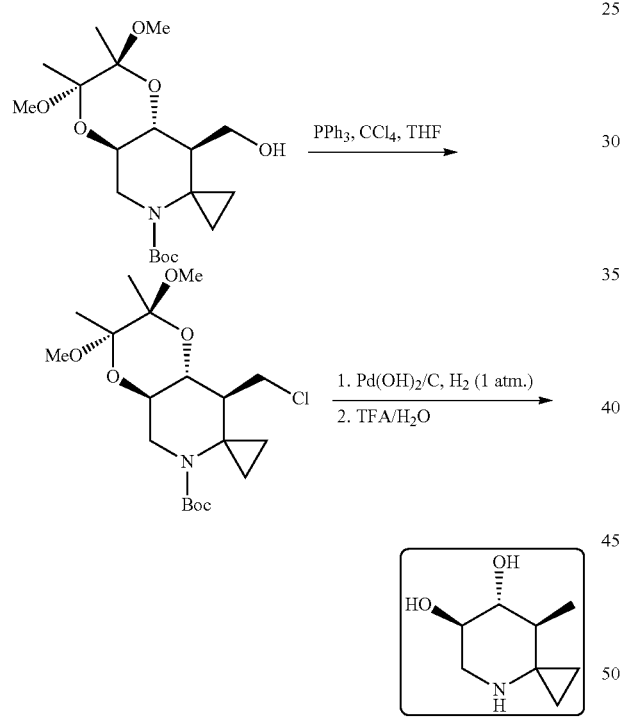
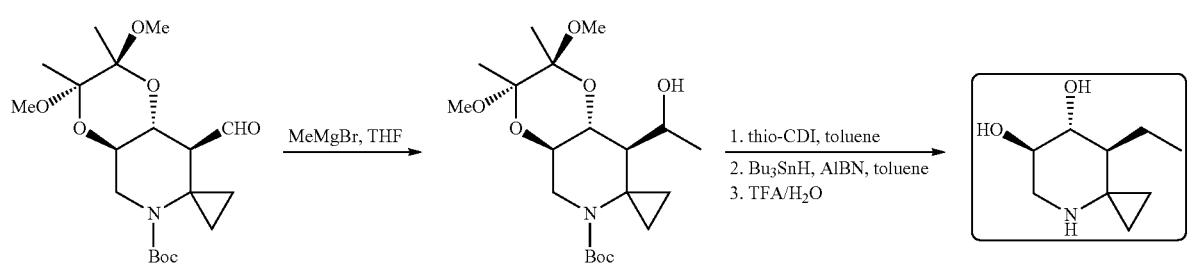

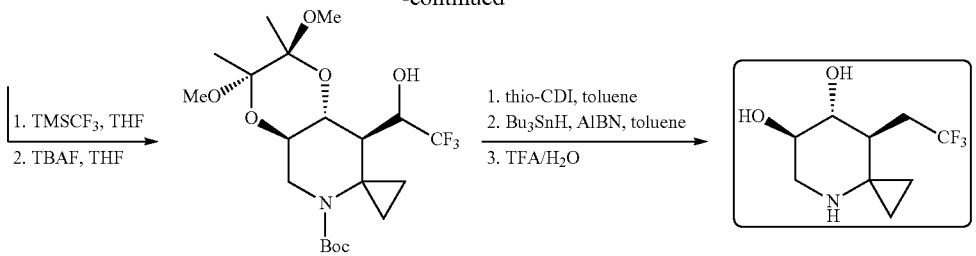
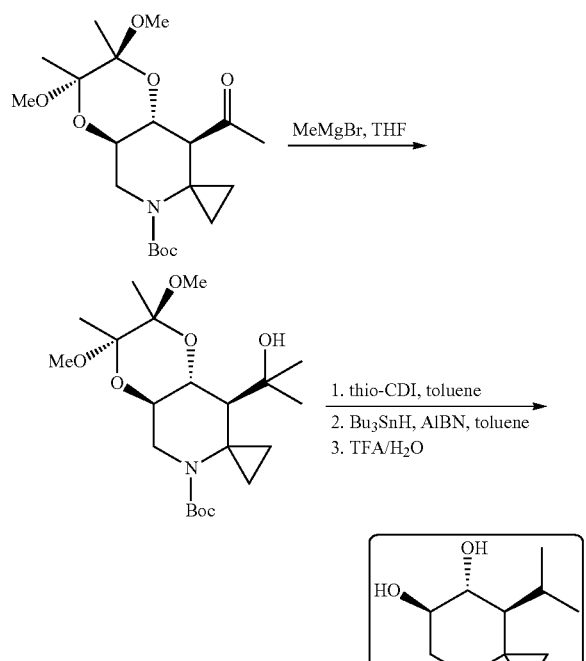
Scheme 6
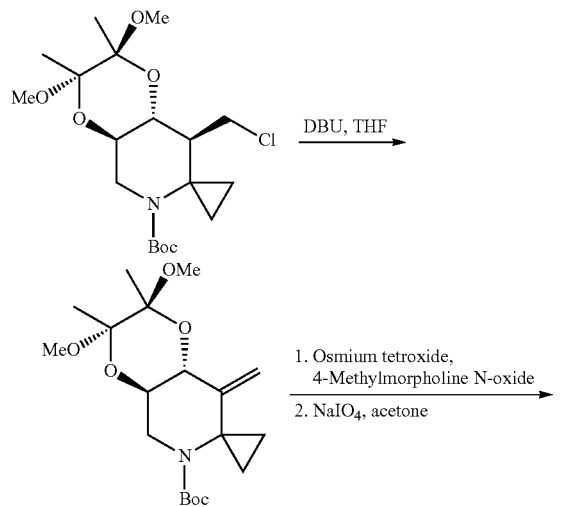
Scheme 7
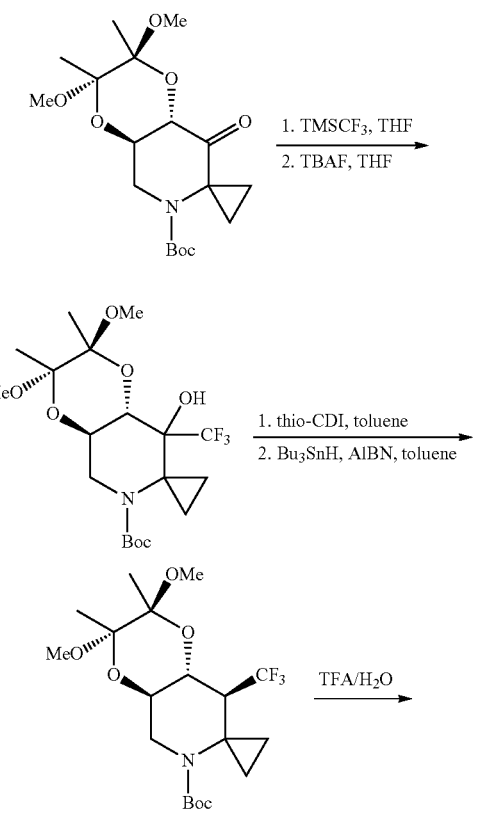
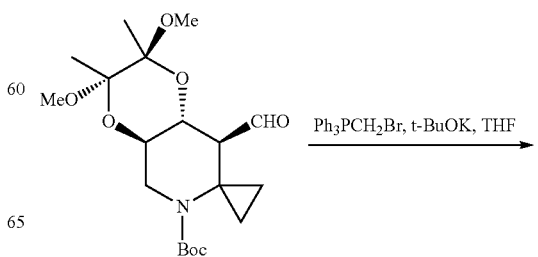
Scheme 8

Scheme 9
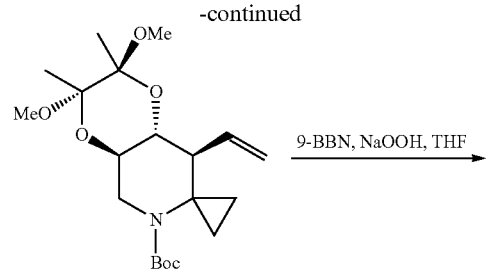
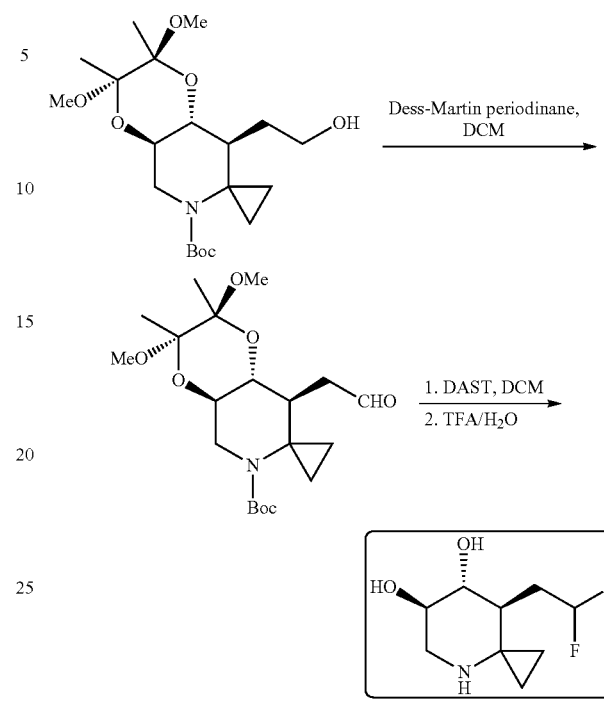
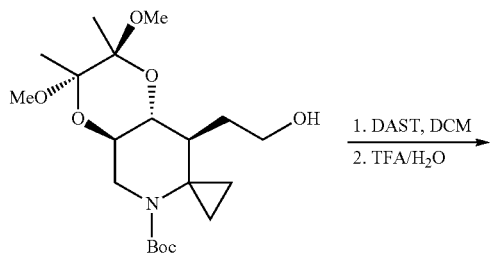
Scheme 10
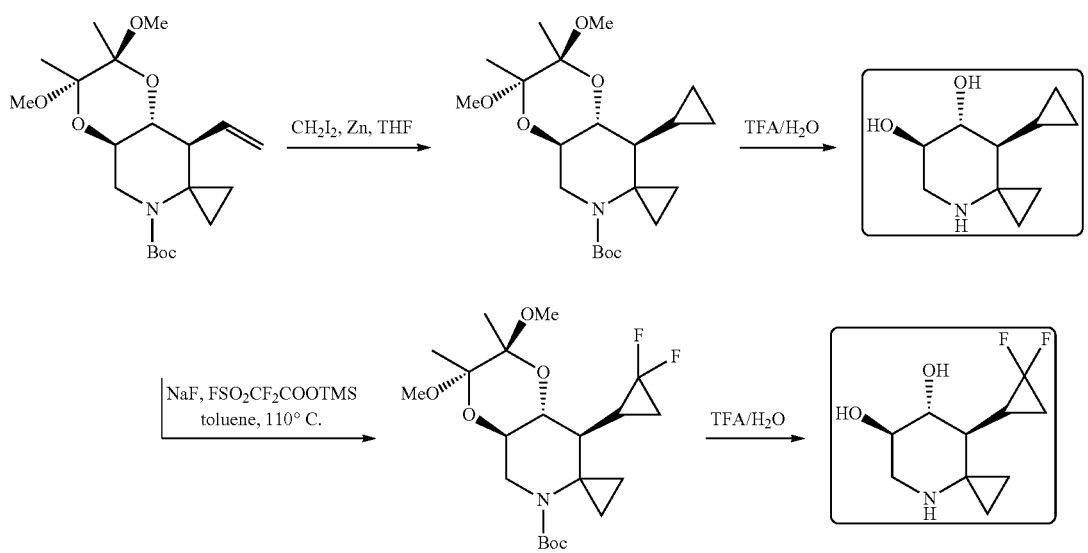
Scheme 11
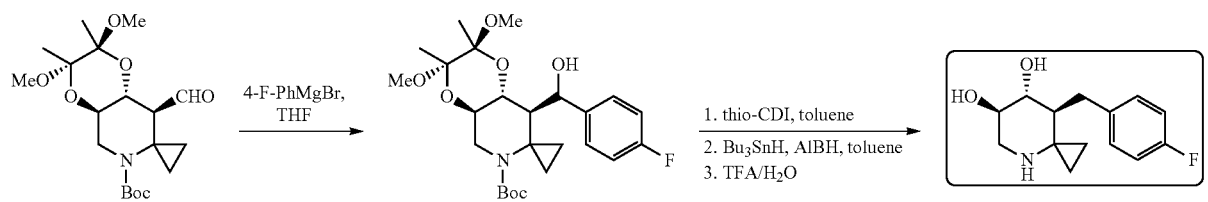

-continued
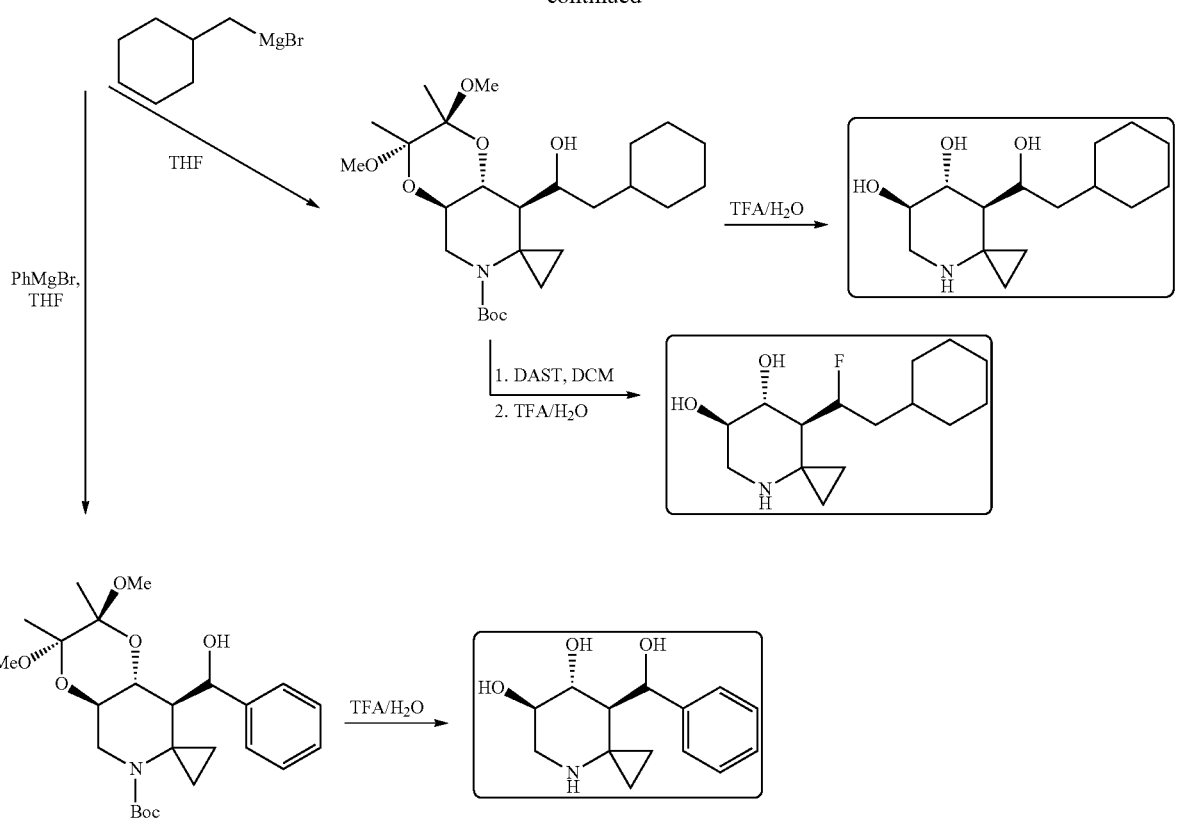
Scheme 12
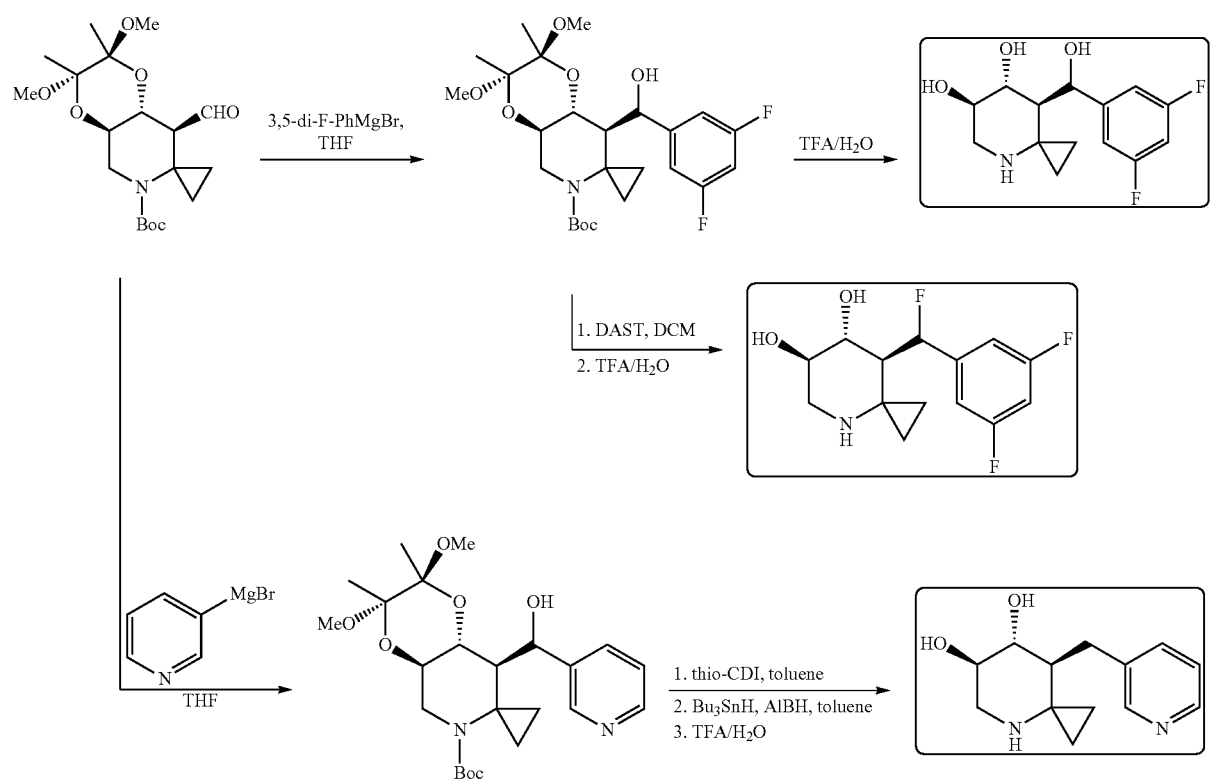

Scheme 13
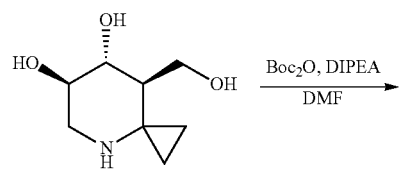
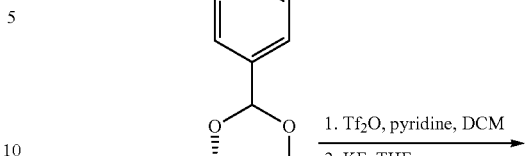
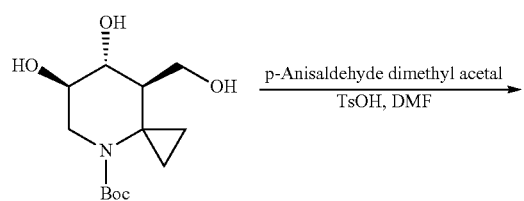
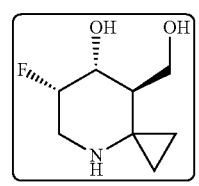
Scheme 14
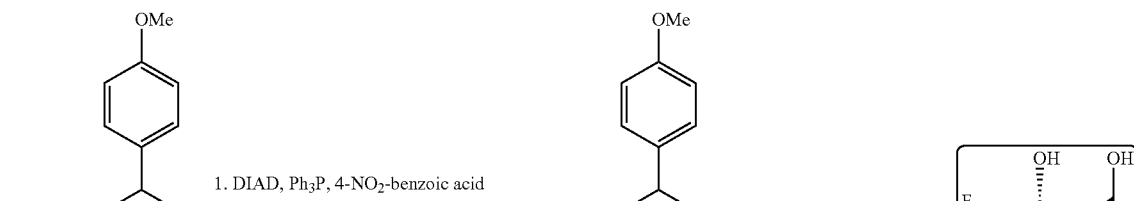
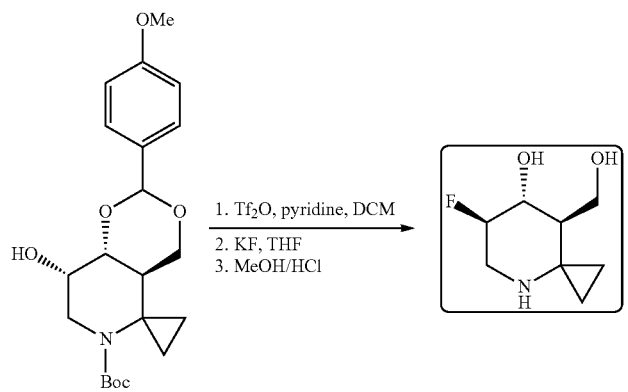
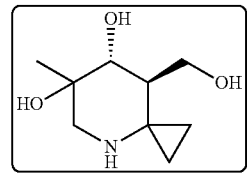
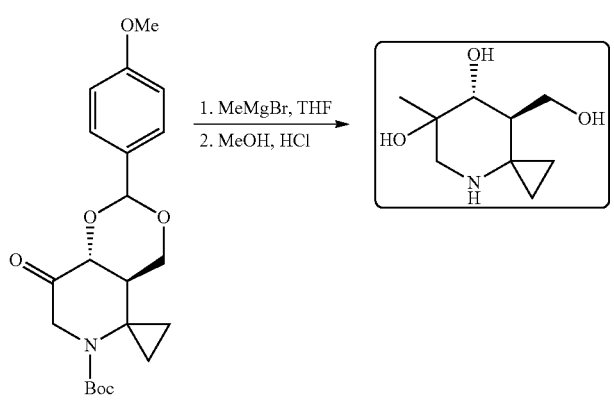

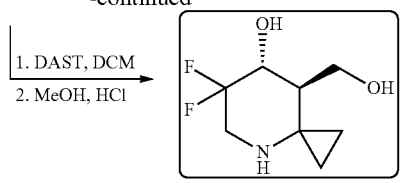
Scheme 15
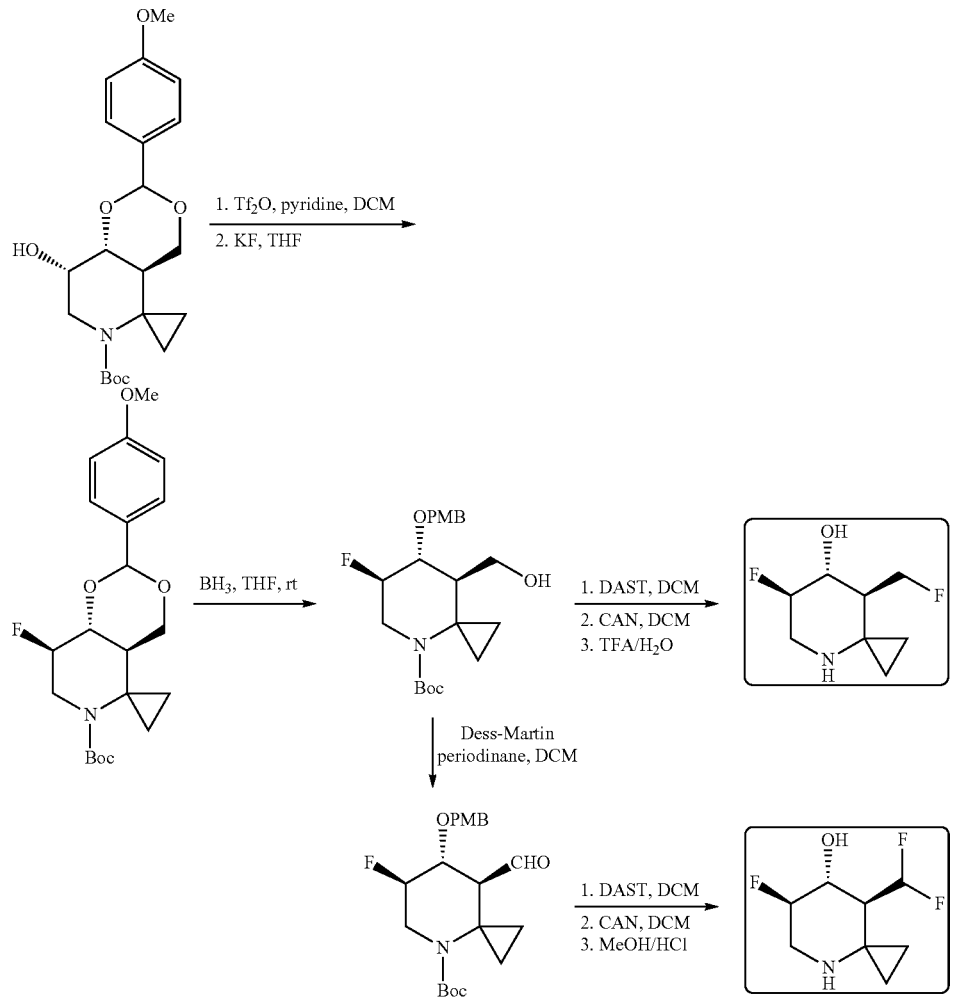
Scheme 16
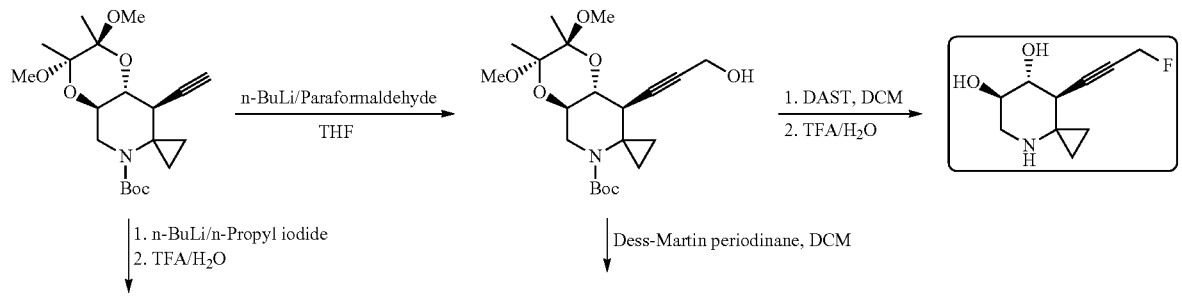

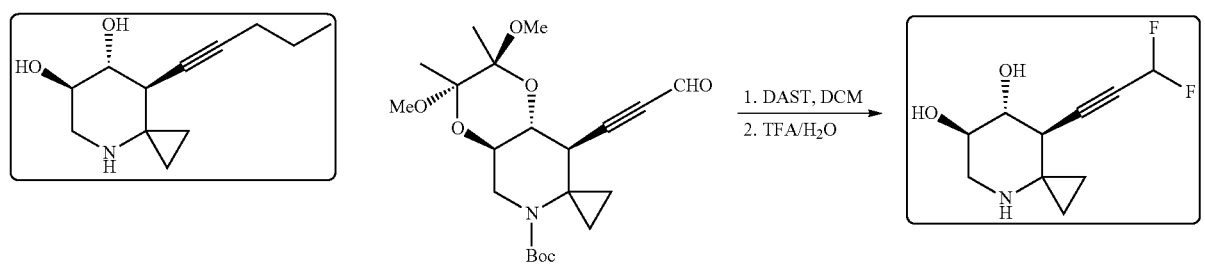
Scheme 17
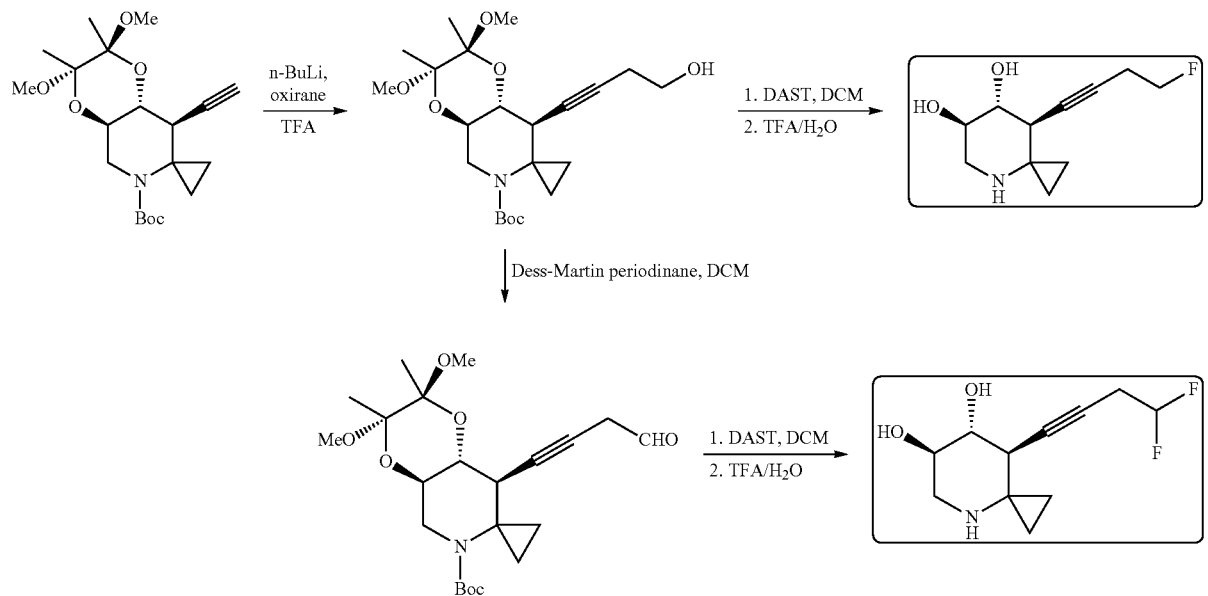
Scheme 18
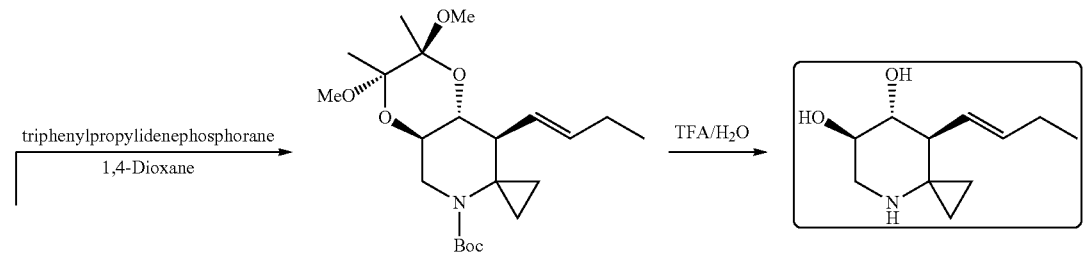
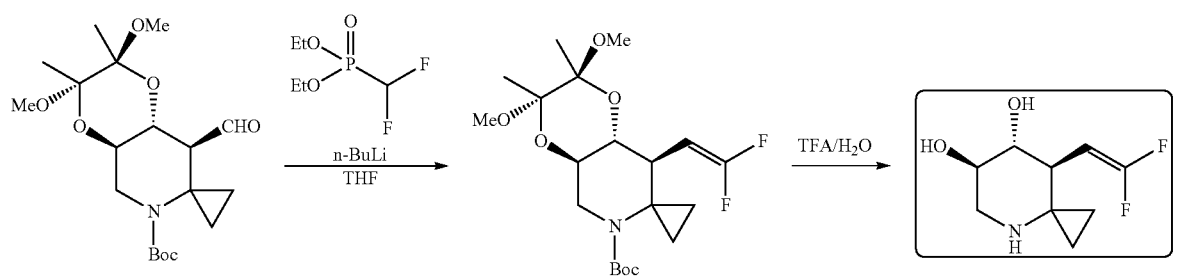

-continued

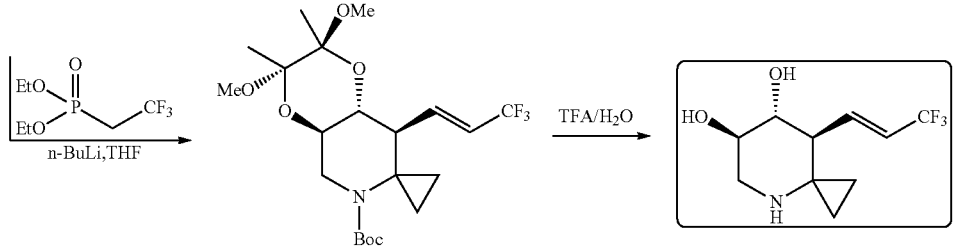

(3R,4R,5R)-5-(hydroxymethyl)-6,6-dimethylpiperidine-3,4-diol

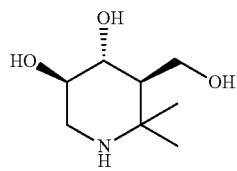

Cerium(III) chloride heptahydrate (3.34 g, 8.8 mmol) powder was stirred under vacuum at 145° C. for 5 h, then at 110° C. for 18 h. The solid was allowed to cool to room temperature. THF (10 mL) was added and the solid was stirred at room temperature for 2 h. The suspension was cooled to −78° C. MeLi (5 mL, 1.6 M in Et$_2$O, 8.0 mmol) was added dropwise. The reaction mixture was stirred −78° C. for 30 min. A solution of (2S,3S,4aS,5S,8R,8aR)-5-(benzyloxy)-2,3-dimethoxy-2,3-dimethylhexahydro-2H-pyrano[3,4-b][1,4]dioxine-8-carbonitrile (740 mg, 2.0 mmol) in THF (5 mL) was introduced dropwise. The reaction was allowed to proceed at −78° C. for 2 h, then 0° C. for another 2 h. Conc. NH$_4$OH (5 mL) was added and the reaction mixture was allowed to warm to room temperature. DCM (50 mL) was added and the mixture was stirred at room temperature for 1 h, then filtered through a celite pad. The celite pad was washed with DCM. The combined filtrates were concentrated under reduced pressure. The obtained residue was purified by chromatography to give 2-((2S,3S,4aS,5S,8R,8aR)-5-(benzyloxy)-2,3-dimethoxy-2, 3-dimethylhexahydro-2H-pyrano[3,4-b][1,4]dioxin-8-yl) propan-2-amine (780 mg, 95%) as a light yellow oil. $^1$H NMR (400 MHz, CDCl$_3$) δ 7.46-7.42 (m, 2H), 7.39-7.34 (m, 2H), 7.32-7.27 (m, 1H), 4.90 (d, J=9.6 Hz, 1H), 4.78-4.62 (m, 2H), 4.57-4.50 (m, 1H), 4.42-4.35 (m, 1H), 3.96-9.90 (m, 1H), 3.78 (dd, J=0.8, 12.8 Hz, 1H), 3.285 (s, 3H), 3.236 (s, 3H), 1.90-1.85 (m, 1H), 1.40 (s, 3H), 1.35 (s, 3H), 1.31 (s, 3H), 1.23 (s, 3H); MS, (ES, m/z) [M+Na]$^+$396.23.

To a solution of the above material (780 mg, 1.97 mmol) in MeOH (40 mL) was added Pd(OH)$_2$/C (20 wt. %, 70 mg, 0.1 mmol) and the mixture was treated with hydrogen (1 atm) for 18 h. Catalyst was filtered off through celite and the solvent was evaporated under reduced pressure to give((2S, 3S,4aR,8R,8aR)-2,3-dimethoxy-2,3,7,7-tetramethyloctahydro-[1,4]dioxino[2,3-c]pyridin-8-yl)methanol as a light yellow oil (570 mg, 100%). MS, (ES, m/z) [M+Na]$^+$290.19.

TFA (2 mL) and H$_2$O (0.2 mL) mixture was cooled to 0° C., added to the above material (40 mg, 0.14 mmol) at 0° C. The mixture was stirred at 0° C. for 10 min, then room temperature for 4 h. TFA was removed under vacuum. The residue was purified by silica gel flash chromatography (using 70:20:2 DCM/MeOH/NH$_4$OH as eluent) to give (3R,4R,5R)-5-(hydroxymethyl)-6,6-dimethylpiperidine-3, 4-diol (24 mg, 98%). $^1$H NMR (400 MHz, CD$_3$OD) δ 3.92-3.82 (m, 2H), 3.69-3.60 (m, 2H), 3.31-3.25 (m, 1H), 3.02-2.92 (m, 1H), 1.68-1.60 (m, 1H), 1.53 (s, 3H), 1.41 (s, 3H); MS, (ES, m/z) [M+H]$^+$ 176.13.

EXAMPLES

Example 1

(6R,7R,8S)-8-methyl-4-azaspiro[2.5]octane-6,7-diol

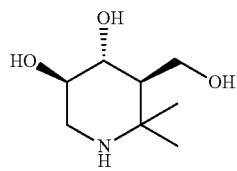

To a solution of (2S,3S,4aR,8R,8aR)-tert-butyl 8-(hydroxymethyl)-2,3-dimethoxy-2,3-dimethyltetrahydro-2H-spiro[[1,4]dioxino[2,3-c]pyridine-7,1'-cyclopropane]-6 (3H)-carboxylate (110 mg, 0.28 mmol) in THF (4 mL) at 0° C. was added NaH (57%-63% in mineral oil, 50 mg, 1.25 mmol) followed by CS$_2$ (0.07 mL, 1.2 mmol). The mixture was stirred for 1 h at room temperature then MeI (0.15 mL, 8.6 mmol) was added dropwise. The resulting mixture was stirred for an additional 1 h, then concentrated and diluted with EtOAc. The organic phase was washed with satd. aqueous NaHCO$_3$ and brine then dried over MgSO$_4$. Evaporation of solvent gave the crude material which was purified by silica gel flash chromatography, eluting with 30% EtOAc in hexanes to afford (2S,3S,4aR,8R,8aR)-tert-butyl 2,3-dimethoxy-2,3-dimethyl-8-(((methylthio)carbonothioyl)eoxy) methyl)tetrahydro-2H-spiro[[1,4]dioxino[2,3-c]pyridine-7, 1'-cyclopropane]-6(3H)-carboxylate (135 mg, 100%) as a white foam.

To a refluxing solution of the above material (136 mg, 0.28 mmol) in benzene (2 mL) was added dropwise a solution of n-Bu$_3$SnH (0.11 mL, 0.42 mmol) and ABCN (7 mg, 0.028 mmol) in benzene (1 mL) over 15 min. The reaction was stirred for 1 h under reflux, cooled to room temperature, concentrated and diluted with EtOAc. The organic phase was washed with satd. aqueous NaHCO$_3$ and brine then dried over MgSO$_4$. Evaporation of solvent gave the crude material which was re-dissolved in THF (2 mL), and treated with solid KF (100 mg) with stirring for 1 h, to remove the tin byproducts. Evaporation of solvent gave the crude material which was purified by silica gel flash chromatography, eluting with 7% EtOAc in hexanes to afford (2S,3S,4aR,8R,8S,8aR)-tert-butyl 2,3-dimethoxy-2,3,8-trimethyltetrahydro-2H-spiro[[1,4]dioxino[2,3-c]pyridine-7,1'-cyclopropane]-6(3H)-carboxylate (57 mg, 55%) as a white foam.

The above material (57 mg, 0.15 mmol) was dissolved in TFA/H$_2$O (9:1, 2 mL) and the reaction mixture was stirred for 2 h at room temperature then evaporated to dryness. The crude material was purified by silica gel flash chromatography, eluting with 5:10:85 NH$_4$OH:MeOH:DCM to afford (6R,7R,8S)-8-methyl-4-azaspiro[2.5]octane-6,7-diol (21 mg, 91%) as a white foam. $^1$H NMR (400 MHz, d-MeOH) δ 3.50-3.42 (m, 1H), 3.07 (dd, J=8, 9.6 Hz, 1H), 3.00 (dd, J=5.2, 12.4 Hz, 1H), 2.5 (dd, J=10.8, 12.4 Hz, 1H), 1.94-1.86 (m, 1H), 0.72 (d, J=6.8 Hz, 3H), 0.7-0.66 (m, 1H), 0.63-0.58 (m, 1H), 0.52-0.47 (m, 1H), 0.38-0.33 (m, 1H); MS m/z 158.30 (M+1, 100%).

Example 2

(6R,7R,8R)-8-(hydroxymethyl)-4-azaspiro[2.5]octane-6,7-diol

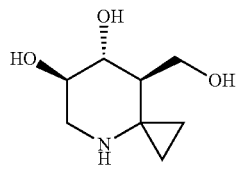

A stock triisopropoxymethyltitanium solution (0.5 M) was prepared as follows: To a stirred, pre-cooled (ice bath) flask charged with titanium (IV) isopropoxide (2.68 mL, 9.0 mmol) was added dropwise titanium tetrachloride (0.32 mL, 3.0 mmol). The mixture was allowed to warm to room temperature and stirred for 5 min. THF (13.5 mL) was added and stirring was continued at room temperature for 30 min. The reaction mixture was cooled to 0° C. and MeLi (1.6 M in diethyl ether, 7.5 mL, 12 mmol) was added. During the addition LiCl precipitated and the color of the suspension changed from orange to bright yellow. After 1 h, a portion of the resulting triisopropoxymethyltitanium solution (0.5 M, 12.6 mL, 6.3 mmol) was transferred to a flask containing (2S,3S,4aS,5S,8R,8aR)-5-(benzyloxy)-2,3-dimethoxy-2,3-dimethylhexahydro-2H-pyrano[3,4-b][1,4]dioxine-8-carbonitrile (PCT Int. Appl. No. WO 2008144773) (1.5 g, 4.2 mmol) in THF (20 mL) at room temperature, followed by the addition of ethyl magnesium bromide (3.0 M in Et$_2$O, 2.0 mL, 6.0 mmol). The resulting brown mixture was stirred 1 h at room temperature, then boron trifluoride etherate (1.0 mL, 8.1 mmol) was added and resulting mixture was stirred for an additional h at room temperature, then quenched by adding 2 N HCl (6.3 mL, 12.6 mmol), H$_2$O (30 mL) and then neutralized by addition of NaOH (3M, 5 mL, 15.0 mmol). The aqueous layer was extracted by EtOAc (3×100 mL) and the resulting organic solution was washed with water, brine, and dried over Na$_2$SO$_4$. The solvent was evaporated to give the crude material, which was purified by silica gel flash chromatography, eluting with 3% MeOH and 3% ammonium hydroxide in DCM to give (1-((2S,3S,4aS,5S,8R,8aR)-5-(benzyloxy)-2,3-dimethoxy-2,3-dimethylhexahydro-2H-pyrano[3,4-b][1,4]dioxin-8-yl)cyclopropanamine as a white solid (1.4 g, 75%). $^1$H NMR (500 MHz, CDCl$_3$) δ 7.41 (d, J=6 Hz, 2H), 7.34 (dd, J=7.0 Hz, 7.0 Hz, 2H), 7.28 (d, J=7.0 Hz, 1H), 4.88 (d, J=3.5 Hz, 1H), 4.70 (d, J=12.5 Hz, 1H), 4.66 (d, J=12.5 Hz, 1H), 4.45 (d, J=11 Hz, 5.5 Hz, 1H), 4.42 (d, J=11 Hz, 3.5 Hz, 1H), 3.92 (d, J=12.3 Hz, 3.5 Hz 1H), 3.60 (d, J=12 Hz, 1H), 3.25 (s, 3H), 3.23 (s, 3H), 2.19-1.80 (broad, NH$_2$), 1.67-1.60 (m, 1H), 1.34 (s, 3H), 1.29 (s, 3H), 0.69-0.52 (m, 4H); MS m/z 394.22 (M+1, 100%).

The above material (400 mg, 1.5 mmol) was dissolved in MeOH (30 mL), then 5 drops of acetic acid were added followed by addition of Pd(OH)$_2$ (20% palladium hydroxide on carbon wet, 100 mg). Hydrogen gas in a balloon was bubbled though the reaction for 20 min and the mixture was then stirred under hydrogen (1 atm.) at room temperature for 8 h. During the reaction period, hydrogen gas was bubbled though the reaction mixture three times so that the solution was continually saturated with hydrogen. Filtration of the crude reaction though Celite® 545 and evaporation of solvent gave the crude material which was purified by silica gel flash chromatography, eluting with 5% MeOH in EtOAc to afford ((2S,3S,4aR,8R,8aR)-2,3-dimethoxy-2,3-dimethylhexahydro-2H-spiro[[1,4]dioxino[2,3-c]pyridine-7,1'-cyclopropan]-8-yl)methanol as a white solid (284 mg, 65%). $^1$H NMR (500 MHz, CDCl$_3$) δ 3.82 (dd, J=10 Hz, 10 Hz, 1H), 3.71-3.66 (m, 1H), 3.45 (dd, J=11 Hz, 8 Hz, 1H), 3.30 (s, 3H), 3.29 (s, 3H), 3.25 (dd, J=11 Hz, 3.5 Hz, 1H), 2.95 (dd, J=13 Hz, 5 Hz, 1H), 2.72 (dd, J=13 Hz, 11 Hz, 1H), 2.25-2.20 (m, 1H), 2.25-2.20 (broad, NH), 1.33 (s, 3H), 1.30 (s, 3H), 0.80-0.75 (m, 1H), 0.57-0.52 (m, 1H), 0.46-0.37 (m, 2H); MS m/z 288.177 (M+1, 100%).

The above material (30 mg, 0.1 mmol) was dissolved in TFA/H$_2$O (9:1, 1 mL) and the reaction mixture was stirred for 2 h at room temperature then evaporated to dryness. Et$_2$O (2.0 mL) was added to the crude material, and a white solid formed which was then was collected and dried under high vacuum to give (6R,7R,8R)-8-(hydroxymethyl)-4-azaspiro[2.5]octane-6,7-diol as the TFA salt (11 mg). $^1$H NMR (400 MHz, d$_4$-MeOH) δ 3.92 (dd, J=11.6 Hz, 5.6 Hz, 1H), 3.88-3.86 (broad, 2H), 3.79 (dd, J=11.2 Hz, 6.0 Hz, 1H), 3.54-3.48 (m, 1H), 3.06-3.03 (broad, 1H), 1.73-1.67 (broad 1H), 1.16-1.05 (m, 2H), 1.04-0.97 (m, 1H), 0.93-0.55 (m, 1H); MS m/z 174.11 (M+1, 100%).

Example 3

(6R,7R,8S)-8-(fluoromethyl)-4-azaspiro[2.5]octane-6,7-diol

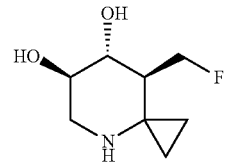

2,2,2-Trifluoro-1-((2S,3S,4aR,8R,8aR)-8-(hydroxymethyl)-2,3-dimethoxy-2,3-dimethyltetrahydro-2H-spiro[[1,4]dioxino[2,3-c]pyridine-7,1'-cyclopropan]-6(3H)-yl)ethanone (0.103 g, 0.27 mmol) was taken up in DCM (12 mL) and cooled to −78° C. DAST (0.18 mL, 1.4 mmol) was added dropwise while stirring at −78° C. After the addition, the cooling bath was removed and reaction mixture stirred at room temperature overnight. The reaction was diluted with satd. aqueous NaHCO$_3$ solution (10 mL). The DCM layer was separated, dried over anhydrous Na$_2$SO$_4$ and concentrated. The crude residue was purified by automatic flash column chromatography (EtOAc/hexanes, 1:4) to provide 2,2,2-trifluoro-1-((2S,3S,4aR,8R,8aR)-8-(hydroxymethyl)-2,3-dimethoxy-2,3-dimethyltetrahydro-2H-spiro[[1,4]dioxino[2,3-c]pyridine-7,1'-cyclopropan]-6(3H)-yl) ethanone (0.076 g, 72.9%) as mixture of rotamers. ES/MS: 408.13 [M+Na].

The above material (0.101 g, 0.26 mmol) was taken up in 7:3 MeOH:H$_2$O (10 mL) followed by the addition of K$_2$CO$_3$ (0.360 g, 2.6 mmol) and stirred at room temperature overnight. The reaction mixture was concentrated and diluted with EtOAc (50 mL) which was subsequently washed with brine, dried over anhydrous Na$_2$SO$_4$, and concentrated. The crude product was purified on silica gel by automatic flash column chromatography (EtOAc, 100%) to provide (2S,3S, 4aR,8S,8aR)-8-(fluoromethyl)-2,3-dimethoxy-2,3-dimethylhexahydro-2H-spiro[[1,4]dioxino[2,3-c]pyridine-7,1'-cyclopropane] (0.055 g, 73%) as a white solid. $^1$H NMR (500 MHz, CDCl$_3$) δ 4.53-4.39 (ddd, J=47.4, 10.0, 5.1 Hz, 1H), 4.33-4.19 (ddd, J=47.9, 9.95, 1.05 Hz, 1H), 3.84-3.79 (dd, J=10.7, 9.6 Hz, 1H), 3.73-3.66 (m, 1H), 3.28 (s, 3H), 3.24 (s, 3H), 2.99-2.93 (dd, J=12.8, 4.9 Hz, 1H), 2.79-2.73 (dd, J=12.5, 11.4 Hz, 1H), 2.23-2.11 (ddd, J=32.0, 11.0, 4.8 Hz, 1H), 1.31 (s, 3H), 1.30 (s, 3H), 0.88-0.83 (m, 1H), 0.81-0.76 (m, 1H), 0.64-0.59 (m, 1H), 0.54-0.48 (m, 1H). ES/MS: 290.17 [M+1].

The above material (0.055 g, 0.19 mmol) was taken up in 90% TFA/H$_2$O (10 mL) at 0° C. and stirred at this temperature for 1 h and slowly warmed to room temperature over the next 1.5 h. The reaction mixture was evaporated to dryness and 2M NH$_3$/MeOH (5 mL) solution was added to neutralize the reaction. The reaction mixture was again concentrated and the crude residue was purified by silica gel column chromatography (DCM/MeOH, 85:15) to provide (6R,7R, 8S)-8-(fluoromethyl)-4-azaspiro[2.5]octane-6,7-diol (0.028 g, 84.2%) as a white solid. $^1$H NMR (400 MHz, MeOD) δ 4.62-4.53 (ddd, J=18.8, 10.0, 6.0 Hz, 1H), 4.50-4.41 (ddd, J=18.4, 10.0, 6.0 Hz, 1H), 3.61-3.51 (m, 2H), 3.14-3.09 (dd, J=12.6, 4.0 Hz, 1H), 2.67-2.60 (dd, J=12.7, 8.5 Hz, 1H), 2.05-1.92 (m, 1H), 0.93-0.87 (m, 1H), 0.86-0.80 (m, 1H), 0.71-0.65 (m, 1H), 0.58-0.51 (m, 1H). ES/MS: 176.10 [M+1].

Example 4

(6R,7R,8S)-8-(difluoromethyl)-4-azaspiro[2.5]octane-6,7-diol

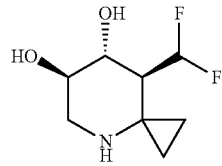

To a solution of ((2S,3S,4aR,8R,8aR)-2,3-dimethoxy-2, 3-dimethylhexahydro-2H-spiro[[1,4]dioxino[2,3-c]pyridine-7,1'-cyclopropan]-8-yl)methanol (170 mg, 0.60 mmol) and triethylamine (0.4 mL, 2.77 mmol) in toluene (3 mL) was added TFAA (0.12 mL, 0.88 mmol) at 0° C. The mixture was stirred for 30 min at room temperature then THF and satd. aqueous NaHCO$_3$ (1:1, 20 mL) were added. The resulting suspension was vigorously stirred for 0.5 h and then extracted with EtOAc (3×30 mL). The organic phase was washed with brine and dried over MgSO$_4$. Evaporation of solvent gave the crude material which was purified by silica gel flash chromatography, eluting with 30% EtOAc in hexanes to afford 2,2,2-trifluoro-1-((2S,3S,4aR,8R,8aR)-8-(hydroxymethyl)-2,3-dimethoxy-2,3-dimethyltetrahydro-2H-spiro[[1,4]dioxino[2,3-c]pyridine-7,1'-cyclopropan]-6 (3H)-yl)ethanone as a white solid (140 mg, 60%).

To a solution of the above material (140 mg, 0.37 mmol) in DCM (3 mL) was added DMP (232 mg, 0.55 mmol). The mixture was stirred for 1 h at room temperature then diluted with EtOAc (20 mL). The organic phase was washed with satd. aqueous NaHCO$_3$ and brine, then dried over MgSO$_4$. Evaporation of solvent gave the crude material which was purified by silica gel flash chromatography, eluting with 20% EtOAc in hexanes to afford (2S,3S,4aR,8S,8aR)-2,3-dimethoxy-2,3-dimethyl-6-(2,2,2-trifluoroacetyl)hexahydro-2H-spiro[[1,4]dioxino[2,3-c]pyridine-7,1'-cyclopropane]-8-carbaldehyde as a white solid (106 mg, 76%).

The above material (106 mg, 0.28 mmol) was taken up in DCM (4 mL) and cooled to −15° C. DAST (0.11 mL, 0.83 mmol) was added dropwise while stirring at −15° C. After the addition, the cooling bath was removed and the reaction mixture was stirred at room temperature overnight. The reaction was diluted with satd. aqueous NaHCO$_3$ solution (10 mL). The DCM layer was separated, dried over anhydrous Na$_2$SO$_4$ and concentrated. The crude residue was purified on silica gel by automatic flash column chromatography eluting with 30% EtOAc in hexanes to provide 1-((2S,3S,4aR,8S,8aR)-8-(difluoromethyl)-2,3-dimethoxy-2,3-dimethyltetrahydro-2H-spiro[[1,4]dioxino[2,3-c]pyridine-7,1'-cyclopropan]-6(3H)-yl)-2,2,2-trifluoroethanone (88 mg, 81%) as a white foam.

The above material (88 mg, 0.22 mmol) was taken up in 1:1 MeOH:H$_2$O (4 mL) then solid K2CO$_3$ (300 mg, 2.2 mmol) was added and the resulting mixture was stirred at room temperature overnight. The reaction mixture was concentrated and diluted with EtOAc (50 mL) then washed with brine, dried over anhydrous Na$_2$SO$_4$ and concentrated. The crude product was purified on silica gel by automatic flash column chromatography eluting with 50% EtOAc in hexanes to provide (2S,3S,4aR,8S,8aR)-8-(difluoromethyl)-2,3-dimethoxy-2,3-dimethylhexahydro-2H-spiro[[1,4]dioxino[2,3-c]pyridine-7,1'-cyclopropane] (58 mg, 87%) as a white foam.

The above material (58 mg, 0.19 mmol) was dissolved in TFA/H$_2$O (9:1, 2 mL) and the reaction mixture was stirred for 2 h at room temperature then evaporated to dryness. The crude material was purified by silica gel flash chromatography, eluting with 5:10:85 NH$_4$OH:MeOH:DCM to afford (6R,7R,8S)-8-(difluoromethyl)-4-azaspiro[2.5]octane-6,7-diol (26 mg, 69%) as a white solid. $^1$H NMR (400 MHz, d-MeOH) δ 6.37 (ddd, J=56.4, 56.4, 6.4 Hz, 1H), 3.92 (t, J=4.8 Hz, 1H), 3.57 (dd, J=7.6, 4.4 Hz, 1H), 3.17 (dd, J=13.6, 2.8 Hz, 1H), 2.66 (dd, J=13.2, 4.8 Hz, 1H), 1.74-1.62 (m, 1H), 0.78-0.70 (m, 2H), 0.65-0.61 (m, 1H), 0.56-0.53 (m, 1H); MS m/z 194.09 (M+1, 100%).

Example 5

(6R,7R,8S)-8-(chloromethyl)-4-azaspiro[2.5]octane-6,7-diol

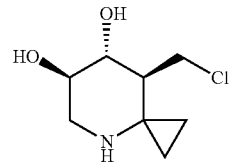 [SMILES: O[C@H]1[C@H](O)CNC2(CC2)[C@@H]1CCl]

To a solution of ((2S,3S,4aR,8R,8aR)-2,3-dimethoxy-2, 3-dimethylhexahydro-2H-spiro[[1,4]dioxino[2,3-c]pyridine-7,1'-cyclopropan]-8-yl)methanol (284 mg, 0.99 mmol) and DIPEA (0.27 mL, 1.47 mmol) in DCM (10 mL) was added Boc$_2$O (237 mg, 1.10 mmol). The mixture was stirred overnight and diluted with EtOAc (100 mL). The organic phase was washed with saturated NH$_4$Cl and brine, then dried over anhydrous MgSO$_4$. Evaporation of solvent gave the crude material which was purified by silica gel column chromatography, eluting with 30% EtOAc in hexanes to afford (2S,3S,4aR,8R,8aR)-tert-butyl 8-(hydroxymethyl)-2,3-dimethoxy-2,3-dimethyltetrahydro-2H-spiro[[1,4]dioxino[2,3-c]pyridine-7,1'-cyclopropane]-6(3H)-carboxylate as a white solid (270 mg, 70%).

To a solution of the above material (137 mg, 0.35 mmol) and Ph$_3$P (276 mg, 1.05 mmol) in DCM (2 mL) was added CCl$_4$ (0.4 mL, 4.10 mmol). The reaction mixture was stirred overnight and then concentrated. The crude material was purified by silica gel column chromatography, eluting with 20% EtOAc in hexanes to afford (2S,3S,4aR,8S,8aR)-tert-butyl 8-(chloromethyl)-2,3-dimethoxy-2,3-dimethyltetrahydro-2H-spiro[[1,4]dioxino[2,3-c]pyridine-7,1'-cyclopropane]-6(3H)-carboxylate as a white solid (143 mg, 100%). This compound was dissolved in TFA/H$_2$O (9:1, 2 mL) and the reaction mixture was stirred for 2 h at room temperature then evaporated to dryness. The crude material was purified by silica gel column chromatography, eluting with 5:10:85 NH$_4$OH:MeOH:DCM to afford (6R,7R,8S)-8-(chloromethyl)-4-azaspiro[2.5]octane-6,7-diol as a white solid (59 mg, 85%). $^1$H NMR (400 MHz, d$_4$-MeOH) δ 3.90 (dd, J=11.6 Hz, 4.8 Hz, 1H), 3.66 (dd, J=7.0 Hz, J=7.0 Hz, 1H), 3.57-3.50 (m, 2H), 3.06 (dd, J=13.2 Hz, J=4 Hz, 1H), 2.60 (dd, J=13.2 Hz, J=7.6 Hz, 1H), 1.93-1.83 (m, 1H), 0.92-0.82 (m, 1H), 0.82-0.78 (m, 1H), 0.67-0.62 (m, 1H), 0.51-0.46 (m, 1H); MS m/z 191.07 (M+1, 100%).

Example 6

(6R,7R,8R)-8-(methoxymethyl)-4-azaspiro[2.5]octane-6,7-diol

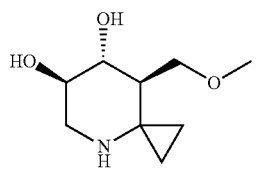

To a solution of (2S,3S,4aR,8R,8aR)-tert-butyl 8-(hydroxymethyl)-2,3-dimethoxy-2,3-dimethyltetrahydro-2H-spiro[[1,4]dioxino[2,3-c]pyridine-7,1'-cyclopropane]-6(3H)-carboxylate (104 mg, 0.27 mmol) in THF (3 mL) was added NaH (57%-63% in mineral oil, 21 mg, 0.54 mmol) followed by MeI (0.1 mL, 1.5 mmol). The mixture was stirred overnight at room temperature, concentrated and diluted with EtOAc (20 mL). The organic phase was washed with satd. aqueous NaHCO$_3$ and brine, then dried over MgSO$_4$. Evaporation of solvent gave the crude material which was purified by silica gel flash chromatography, eluting with 30% EtOAc in hexanes to afford (2S,3S,4aR,8R,8aR)-tert-butyl 2,3-dimethoxy-8-(methoxymethyl)-2,3-dimethyltetrahydro-2H-spiro[[1,4]dioxino[2,3-c]pyridine-7,1'-cyclopropane]-6(3H)-carboxylate (96 mg, 89%) as a white foam.

The above material (98 mg, 0.24 mmol) was dissolved in TFA/H$_2$O (9:1, 2 mL) and the reaction mixture was stirred for 2 h at room temperature then evaporated to dryness. The crude material was purified by silica gel flash chromatography, eluting with 5:10:85 NH$_4$OH:MeOH:DCM to afford ((6R,7R,8R)-8-(methoxymethyl)-4-azaspiro[2.5]octane-6,7-diol (38 mg, 83%). $^1$H NMR (400 MHz, d-MeOH) δ 3.62-3.44 (m, 3H), 3.30 (dd, J=10, 6.4 Hz, 1H), 3.27 (s, 3H), 3.01 (dd, J=4.4, 9.2 Hz, 1H), 2.52 (dd, J=9.2, 12.8 Hz, 1H), 1.96-1.85 (m, 1H), 0.89-0.84 (m, 1H), 0.79-0.74 (m, 1H), 0.58-0.52 (m, 1H), 0.42-0.38 (m, 1H); MS m/z 188.13 (M+1, 100%).

Example 7

(6R,7S,8S)-8-methoxy-4-azaspiro[2.5]octane-6,7-diol

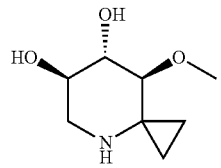

To a solution of (2S,3S,4aR,8S,8aR)-tert-butyl 8-formyl-2,3-dimethoxy-2,3-dimethyltetrahydro-2H-spiro[[1,4]dioxino[2,3-c]pyridine-7,1'-cyclopropane]-6(3H)-carboxylate (773 mg, 2.01 mmol) in DCM (20 mL) was added MCPBA (675 mg, 77% pure, 3.00 mmol). The mixture was stirred for 24 h at room temperature, then diluted with EtOAc. The organic solution was washed with satd. NaHCO$_3$, brine, dried over MgSO$_4$. Evaporation of solvent gave the crude which was purified by silica gel flash chromatography, eluting with 10% first then 30% EtOAc in hexanes to afford (2S,3S,4aR,8S,8aR)-6-(tert-butoxycarbonyl)-2,3-dimethoxy-2,3-dimethylhexahydro-2H-spiro[[1,4]dioxino[2,3-c]pyridine-7,1'-cyclopropane]-8-carboxylic acid (296 mg, 40%) and (2S,3S,4aR,8S,8aS)-tert-butyl 8-(formyloxy)-2,3-dimethoxy-2,3-dimethyltetrahydro-2H-spiro[[1,4]dioxino[2,3-c]pyridine-7,1'-cyclopropane]-6(3H)-carboxylate (169 mg, 20%) as white solids.

To a solution of (2S,3S,4aR,8S,8aS)-tert-butyl 8-(formyloxy)-2,3-dimethoxy-2,3-dimethyltetrahydro-2H-spiro[[1,4]dioxino[2,3-c]pyridine-7,1'-cyclopropane]-6(3H)-carboxylate (169 mg, 0.42 mmol) in MeOH and H$_2$O (3:1, 4 mL) was added KOH (380 mg, 6.8 mmol). The mixture was heated at reflux for 1 h, cooled to room temperature and diluted with EtOAc. The organic solution was washed with satd. NaHCO$_3$, brine, dried over MgSO$_4$. Evaporation of solvent gave the crude which was purified by silica gel flash chromatography, eluting with 20% of EtOAc in hexanes to afford (2S,3S,4aR,8S,8aR)-tert-butyl 8-hydroxy-2,3-dimethoxy-2,3-dimethyltetrahydro-2H-spiro[[1,4]dioxino[2,3-c]pyridine-7,1'-cyclopropane]-6(3H)-carboxylate (158 mg, 100%) as a white solid.

To a solution of the above material (53 mg, 0.14 mmol) in THF (1 mL) was added NaH (11 mg, 57%-64%, 0.27 mmol), followed by addition of MeI (0.05 mL, 0.71 mmol). The mixture was warmed to 50° C. for 2 h, cooled to room temperature and diluted with EtOAc. The organic solution was washed with satd. NaHCO$_3$, brine, dried over MgSO$_4$. Evaporation of solvent gave the crude which was purified by silica gel flash chromatography, eluting with 10% of EtOAc in hexanes to afford (2S,3S,4aR,8S,8aS)-tert-butyl 2,3,8-trimethoxy-2,3-dimethyltetrahydro-2H-spiro[[1,4]dioxino

[2,3-c]pyridine-7,1'-cyclopropane]-6(3H)-carboxylate as a white solid. The crude material was dissolved in TFA/H₂O (9:1, 2 mL) and the reaction mixture was stirred for 2 h at room temperature then evaporated to dryness. The crude was purified by silica gel flash chromatography eluting with 5:10:85 of NH₃H₂O:MeOH:DCM to afford (6R,7S,8S)-8-methoxy-4-azaspiro[2.5]octane-6,7-diol (22 mg, 89% over 2 steps). ¹H NMR (400 MHz, d-MeOH) δ 3.35-3.47 (m, 1H), 3.49 (s, 3H), 3.37-3.38 (m, 2H), 3.14 (d, J=8.4 Hz, 1H), 2.95 (dd, J=4.8, 12.8 Hz, 1H), 2.47 (dd, J=10, 12.8 Hz, 1H), 0.70-0.65 (m, 2H), 0.57-0.54 (m, 1H), 0.40-0.34 (m, 1H); m/z 174.12 (M+1, 100%).

Example 8

(6R,7R,8R)-6,7-dihydroxy-4-azaspiro[2.5]octane-8-carbonitrile

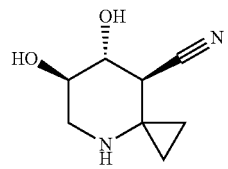

To a solution of (2S,3S,4aR,8S,8aR)-tert-butyl 8-formyl-2,3-dimethoxy-2,3-dimethyltetrahydro-2H-spiro[[1,4]dioxino[2,3-c]pyridine-7,1'-cyclopropane]-6(3H)-carboxylate (316 mg, 0.82 mmol) and NH₂OH HCl salt (286 mg, 3.77 mmol) in EtOH/H₂O (1:1, 6 mL) was added NaHCO₃ (276 mg, 3.28 mmol). The mixture was stirred overnight at room temperature, concentrated and diluted with EtOAc (30 mL). The organic solution was washed with satd. aqueous NaHCO₃ and brine, then dried over MgSO₄. Evaporation of solvent gave the crude (2S,3S,4aR,8R,8aR)-tert-butyl 8-((hydroxyimino)methyl)-2,3-dimethoxy-2,3-dimethyltetrahydro-2H-spiro[[1,4]dioxino[2,3-c]pyridine-7,1'-cyclopropane]-6(3H)-carboxylate (281 mg, 85%) as a mixture of trans and cis isomers, which was used directly in the next step.

To a solution of the above material (281 mg, 0.70 mmol) in pyridine (3 mL) at 0° C. was added MsCl (0.4 mL, 5.2 mmol). The mixture was stirred for 1 h at 0° C. then diluted with EtOAc (30 mL). The organic phase was washed with satd. aqueous NaHCO₃ and brine, then dried over MgSO₄. Evaporation of solvent gave the crude material which was purified by a silica gel flash chromatography, eluting with 10% EtOAc in hexanes to afford (2S,3S,4aR,8R,8aR)-tert-butyl 8-cyano-2,3-dimethoxy-2,3-dimethyltetrahydro-2H-spiro[[1,4]dioxino[2,3-c]pyridine-7,1'-cyclopropane]-6(3H)-carboxylate (229 mg, 86%) as a white foam.

The above material (229 mg, 0.60 mmol) was dissolved in TFA/H₂O (9:1, 2 mL) and the reaction mixture was stirred for 2 h at room temperature then evaporated to dryness. The crude material was purified by a silica gel flash chromatography, eluting with 5:10:85 NH₄OH:MeOH:DCM to afford (6R,7R,8R)-6,7-dihydroxy-4-azaspiro[2.5]octane-8-carbonitrile (63 mg, 63%) as a white solid. ¹H NMR (500 MHz, d-MeOH) δ 3.60 (t, J=9 Hz, 1H), 3.43-3.37 (m, 1H), 3.09 (d, J=9.5 Hz, 1H), 3.01 (dd, J=13, 5 Hz, 1H), 2.53 (dd, J=13, 10.5 Hz, 1H), 0.91-0.78 (m, 3H), 0.67-0.63 (m, 1H); MS m/z 169.10 (M+1, 100%).

Example 9

(6R,7R,8S)-6,7-dihydroxy-4-azaspiro[2.5]octane-8-carboxylic acid

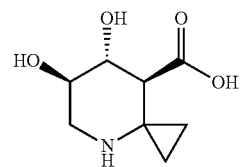

(2S,3S,4aR,8S,8aR)-6-(tert-butoxycarbonyl)-2,3-dimethoxy-2,3-dimethylhexahydro-2H-spiro[[1,4]dioxino[2,3-c]pyridine-7,1'-cyclopropane]-8-carboxylic acid was dissolved in TFA/H₂O (9:1, 2 mL) and reaction mixture was stirred for 2 h at room temperature then evaporated to dryness. The crude was washed with Et₂O and dried under high vacuum to give (6R,7R,8S)-6,7-dihydroxy-4-azaspiro[2.5]octane-8-carboxylic acid as the TFA salt (23 mg, 50%). ¹H NMR (400 MHz, d-MeOH) δ 4.32 (br s, 1H), 3.93 (br s, 1H), 3.59 (d, J=12.8 Hz, 1H), 3.15 (d, J=12 Hz, 1H), 2.45 (br s, 1H), 1.02-1.09 (m, 2H), 1.01-0.92 (m, 2H); m/z 188.09 (M+1, 100%).

Example 10

(6R,7R,8S)-6,7-dihydroxy-N-methyl-4-azaspiro[2.5]octane-8-carboxamide

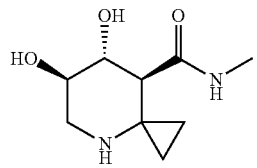

To a solution of (2S,3S,4aR,8S,8aR)-6-(tert-butoxycarbonyl)-2,3-dimethoxy-2,3-dimethylhexahydro-2H-spiro[[1,4]dioxino[2,3-c]pyridine-7,1'-cyclopropane]-8-carboxylic acid (85 mg, 0.21 mmol), HOBt (43 mg, 0.318 mmol), methyl amine hydrochloride salt (22 mg, 0.318 mmol) and i-Pr₂NEt (0.1 mL, 0.55 mmol) in DMF (2 mL) was added HATU (121 mg, 0.32 mmol). The mixture was stirred for 24 h at room temperature then diluted with EtOAc. The organic solution was washed with satd. NaHCO₃, brine, dried over MgSO₄. Evaporation of solvent gave the crude which was purified by silica gel flash chromatography, eluting with 30% EtOAc in hexanes to afford desired amide product as a white solid. This intermediate was dissolved in TFA/H₂O (9:1, 2 mL), stirred for 2 h at room temperature then evaporated to dryness. The crude was purified by silica gel flash chromatography, eluting with 5:10:85 of NH₃H₂O:MeOH:DCM to afford (6R,7R,8S)-6,7-dihydroxy-N-methyl-4-azaspiro[2.5]octane-8-carboxamide (20 mg, 48% over two steps) as a white solid. ¹H NMR (400 MHz, d-MeOH) δ 3.85 (dd, J=8.0, 9.2 Hz, 1H), 3.55-3.50 (m, 1H), 3.05 (dd, J=4.8, 12.8 Hz, 1H), 2.7 (s, 3H), 2.64-2.58 (m, 2H), 0.95-0.89 (m, 1H), 0.70-0.64 (m, 1H), 0.56-0.50 (m, 1H); m/z 201.13 (M+1, 100%).

Example 11

(6R,7R,8S)—N-cyclopropyl-6,7-dihydroxy-4-azaspiro[2.5]octane-8-carboxamide

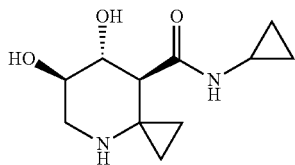

To a solution of (2S,3S,4aR,8S,8aR)-6-(tert-butoxycarbonyl)-2,3-dimethoxy-2,3-dimethylhexahydro-2H-spiro[[1,4]dioxino[2,3-c]pyridine-7,1'-cyclopropane]-8-carboxylic acid (85 mg, 0.21 mmol), HOBT (43 mg, 0.318 mmol), cyclopropylamine (0.026 ml, 0.318 mmol) and i-Pr$_2$NEt (0.1 mL, 0.55 mmol) in DMF (2 mL) was added HATU (121 mg, 0.32 mmol). The mixture was stirred for 24 h at room temperature then diluted with EtOAc. The organic solution was washed with satd. NaHCO$_3$, brine, dried over MgSO$_4$. Evaporation of solvent gave the crude which was purified by silica gel flash chromatography, eluting with 30% EtOAc in hexanes to afford desired amide product as a white solid. This intermediate was dissolved in TFA/H$_2$O (9:1, 2 mL), stirred for 2 h at room temperature then evaporated to dryness. The crude was purified by silica gel flash chromatography, eluting with 5:10:85 of NH$_3$H$_2$O:MeOH:DCM to afford (6R,7R,8S)—N-cyclopropyl-6,7-dihydroxy-4-azaspiro[2.5]octane-8-carboxamide (25 mg, 52% over two steps) as a white solid. $^1$H NMR (400 MHz, d-MeOH) δ 3.84 (dd, J=8.4, 9.2 Hz, 1H), 3.53-3.47 (m, 1H), 3.04 (dd, J=5.2, 12.8 Hz, 1H), 2.65-2.55 (m, 3H), 0.96-0.88 (m, 1H), 0.75-0.62 (m, 3H), 0.55-0.42 (m, 4H); m/z 227.15 (M+1, 100%).

Example 12

(6R,7R,8S)-8-ethyl-4-azaspiro[2.5]octane-6,7-diol

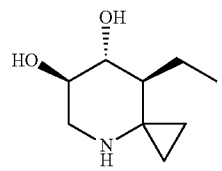

To a solution of (6R,7R,8S)-8-vinyl-4-azaspiro[2.5]octane-6,7-diol (50 mg, 0.29 mmol) in MeOH (3 mL) was added Pd/C (10% on activated carbon, 20 mg). Hydrogen under atmospheric pressure (balloon) was passed though the reaction for 1 h at room temperature. Filtration of the crude reaction mixture though Celite®-545 and evaporation of solvent gave the crude material which was purified by silica gel flash chromatography, eluting with 5:10:85 NH$_4$OH:MeOH:DCM to afford 6R,7R,8S)-8-ethyl-4-azaspiro[2.5]octane-6,7-diol as a white solid (25 mg, 49%). $^1$H NMR (400 MHz, MeOH) δ 3.50-3.33 (m, 1H), 3.35-3.31 (m, 1H), 3.03 (dd, J=4.8, 12.8 Hz, 1H), 2.55 (dd, J=12.4, 13.2 Hz, 1H), 1.65-1.56 (m, 1H), 1.47-1.43 (m, 1H), 1.01-0.90 (m, 4H), 0.71-0.66 (m, 1H), 0.61-0.56 (m, 1H), 0.52-0.48 (m, 1H), 0.42-0.37 (m, 1H); MS m/z 172.13 (M+1, 100%).

Example 13

(6R,7R,8S)-8-propyl-4-azaspiro[2.5]octane-6,7-diol

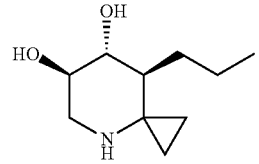

To a solution of ((2S,3S,4aR,8S,8aR)-tert-butyl 2,3-dimethoxy-2,3-dimethyl-8-(prop-1-yn-1-yl)tetrahydro-2H-spiro[[1,4]dioxino[2,3-c]pyridine-7,1'-cyclopropane]-6(3H)-carboxylate (170 mg, 0.43 mmol) in MeOH (3 mL) was added Pd/C (10% on activated carbon, 20 mg). Hydrogen (balloon) was passed though the solution for 48 h at room temperature. Filtration of crude reaction though celite 545 and evaporation of solvent gave the crude which was purified by silica gel flash chromatography, eluting with 15% EtOAc in hexanes afford (2S,3S,4aR,8S,8aR)-tert-butyl 2,3-dimethoxy-2,3-dimethyl-8-propyltetrahydro-2H-spiro[[1,4]dioxino[2,3-c]pyridine-7,1'-cyclopropane]-6(3H)-carboxylate as a white solid (73 mg, 41%).

The above material (74 mg, 0.2 mmol) was dissolved in TFA/H$_2$O (9:1, 2 mL) and reaction mixture was stirred for 2 h at room temperature then evaporated to dryness. The crude was purified by silica gel flash chromatography, eluting with 5:10:85 of NH$_4$OH:MeOH:DCM to afford (6R,7R,8S)-8-propyl-4-azaspiro[2.5]octane-6,7-diol (31 mg, 100%). $^1$H NMR (400 MHz, d-MeOH) δ 3.52-3.47 (m, 1H), 3.38-3.31 (1H, overlapped with MeOH peak), 3.05 (dd, J=4.4, 12.8 Hz, 1H), 2.58 (dd, J=8.8, 12.8 Hz, 1H), 1.66-1.31 (m, 4H), 1.01-0.82 (m, 1H), 0.9 (t, J=7.2 Hz, 3H), 0.7-0.65 (m, 1H), 0.63-0.58 (m, 1H), 0.56-0.50 (m, 1H), 0.45-0.40 (m, 1H); m/z 186.16 (M+1, 100%).

Example 14

(6R,7R,8S)-8-(2-fluoroethyl)-4-azaspiro[2.5]octane-6,7-diol

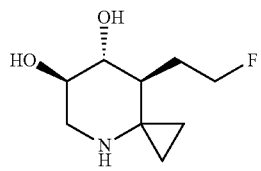

To a solution of (2S,3S,4aR,8S,8aR)-tert-butyl 8-(2-fluorovinyl)-2,3-dimethoxy-2,3-dimethyltetrahydro-2H-spiro[[1,4]dioxino[2,3-c]pyridine-7,1'-cyclopropane]-6(3H)-carboxylate (40 mg, 0.10 mmol) in MeOH (20 mL) was added Pd/C (10 wt. %, 22 mg, 0.02 mmol) and the mixture was treated with hydrogen (1 atm) for 2 days. Catalyst was filtered off through celite and the solvent was evaporated under reduced pressure. The residue was purified by silica gel flash chromatography affording (2S,3S,4aR,8S,8aR)-tert-butyl 8-(2-fluoroethyl)-2,3-dimethoxy-2,3-dimethyltetrahydro-2H-spiro[[1,4]dioxino[2,3-c]pyridine-7,1'-cyclopropane]-6(3H)-carboxylate as a light yellow oil (26 mg, 65%). MS, (ES, m/z) [M+Na]$^+$426.23.

A mixture of TFA (2 mL) and H$_2$O (0.2 mL) was cooled to 0° C., added to (2S,3S,4aR,8S,8aR)-tert-butyl 8-(2-fluoroethyl)-2,3-dimethoxy-2,3-dimethyltetrahydro-2H-spiro[[1,4]dioxino[2,3-c]pyridine-7,1'-cyclopropane]-6(3H)-carboxylate (25 mg, 0.062 mmol) at 0° C. The mixture was stirred at 0° C. for 10 min, then room temperature for 4 h. TFA was removed under vacuum. The residue was purified by silica gel flash chromatography (using 70:20:2 DCM/MeOH/NH$_4$OH as eluent) to give (6R,7R,8S)-8-(2-fluoroethyl)-4-azaspiro[2.5]octane-6,7-diol (8.5 mg, 72%). $^1$H NMR (400 MHz, CD$_3$OD) δ 4.68-4.38 (m, 1H), 3.52-3.45 (m, 1H), 3.38-3.32 (m, 1H), 3.04 (dd, J=4.4, 12.8 Hz, 1H), 2.56 (dd, J=8.8, 12.8 Hz, 1H), 1.93-1.78 (m, 1H), 1.75-1.67 (m, 1H), 1.45-1.25 (m, 1H), 0.75-0.68 (m, 1H), 0.63-0.56 (m, 1H), 0.54-0.41 (m, 2H); MS, (ES, m/z) [M+H]$^+$ 190.13.

Example 15

(6R,7R,8S)-8-(2,2-difluoroethyl)-4-azaspiro[2.5]octane-6,7-diol

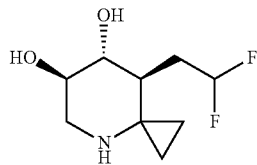 [SMILES: O[C@H]1[C@H](O)CNC2(CC2)[C@@H]1CC(F)F]

To a solution of (2S,3S,4aR,8S,8aR)-tert-butyl 8-(2,2-difluorovinyl)-2,3-dimethoxy-2,3-dimethyltetrahydro-2H-spiro[[1,4]dioxino[2,3-c]pyridine-7,1'-cyclopropane]-6(3H)-carboxylate (60 mg, 0.14 mmol) in MeOH (20 mL) was added Pd/C (10 wt. %, 22 mg, 0.02 mmol) and the mixture was treated with hydrogen (1 atm) for 4 days. Catalyst was filtered off through celite and the solvent was evaporated under reduced pressure. The residue was purified by silica gel flash chromatography affording (2S,3S,4aR,8S,8aR)-tert-butyl difluoroethyl)-2,3-dimethoxy-2,3-dimethyltetrahydro-2H-spiro[[1,4]dioxino[2,3-c]pyridine-7,1'-cyclopropane]-6(3H)-carboxylate as a light yellow oil (47 mg, 78%). MS, (ES, m/z) [M+Na]$^+$ 444.22.

TFA (2 mL) and H$_2$O (0.2 mL) mixture was cooled to 0° C., added to the above material (42 mg, 0.10 mmol) at 0° C. The mixture was stirred at 0° C. for 10 min, then room temperature for 4 h. TFA was removed under vacuum. The residue was purified by silica gel flash chromatography (using 70:20:2 DCM/MeOH/NH$_4$OH as eluent) to give (6R,7R,8S)-8-(2,2-difluoroethyl)-4-azaspiro[2.5]octane-6,7-diol (12 mg, 58%). $^1$H NMR (400 MHz, CD$_3$OD) δ 6.30-5.95 (m, 1H), 3.53-3.46 (m, 1H), 3.36 (t, J=7.6 Hz, 1H), 3.04 (dd, J=4.4, 12.8 Hz, 1H), 2.56 (dd, J=8.8, 12.8 Hz, 1H), 2.07-1.80 (m, 2H), 1.55-1.37 (m, 1H), 0.78-0.71 (m, 1H), 0.66-0.58 (m, 1H), 0.53-0.44 (m, 2H); MS, (ES, m/z) [M+H]$^+$ 208.12.

Example 16

(6R,7R,8S)-8-vinyl-4-azaspiro[2.5]octane-6,7-diol

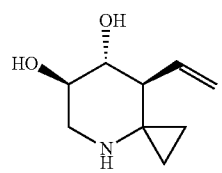

To a suspension of methyl triphenylphosphonium bromide (904 mg, 2.40 mmoL) in THF (20 mL) at 0° C. was added n-BuLi (1.6 M in hexane, 1.24 mL, 2.00 mmol) and the resulting yellow suspension was stirred for 10 min at 0° C., then a solution of (2S,3S,4aR,8S,8aR)-tert-butyl-8-formyl-2,3-dimethoxy-2,3-dimethyltetrahydro-2H-spiro[[1,4]dioxino[2,3-c]pyridine-7,1'-cyclopropane]-6(3H)-carboxylate (191 mg, 0.50 mmol) in THF (1 mL) was added. The resulting mixture was stirred for 1 h at room temperature then diluted with EtOAc (30 mL) and the organic phase was washed with satd. aqueous NaHCO$_3$ and brine then dried over MgSO$_4$. Evaporation of solvent gave the crude material which was purified by silica gel flash chromatography, eluting with 10% EtOAc in hexanes to afford (2S,3S,4aR,8S,8aR)-tert-butyl 2,3-dimethoxy-2,3-dimethyl-8-vinyltetrahydro-2H-spiro[[1,4]dioxino[2,3-c]pyridine-7,1'-cyclopropane]-6(3H)-carboxylate (170 mg, 90%) as a white foam.

The above material (170 mg, 0.44 mmol) was dissolved in TFA/H$_2$O (9:1, 2 mL) and the reaction mixture was stirred for 2 h at room temperature then evaporated to dryness. The crude material was purified by silica gel flash chromatography, eluting with 5:10:85 of NH$_4$OH:MeOH:DCM to afford (6R,7R,8S)-8-vinyl-4-azaspiro[2.5]octane-6,7-diol (71 mg, 91%) as a white foam. $^1$H NMR (400 MHz, d-MeOH) δ 5.41-5.32 (m, 1H), 5.18-5.10 (m, 2H), 3.52-3.46 (m, 1H), 3.38-3.35 (m, 1H), 2.95 (dd, H=5.2, 12.8 Hz, 1H), 2.56 (dd, J=10.4, 12.8 Hz, 1H), 2.47 (t, J=9.4 Hz, 1H), 0.59-0.43 (m, 4H); MS m/z 170.12 (M+1, 100%).

Example 17

(6R,7R,8S)-8-((Z)-2-fluorovinyl)-4-azaspiro[2.5]octane-6,7-diol

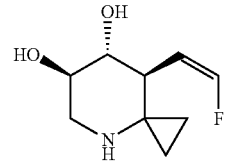 [SMILES: O[C@H]1[C@H](O)CNC2(CC2)[C@@H]1/C=C\F]

A freshly prepared solution of lithium diisoproylamide (2.26 mmol) in anhydrous THF (8 mL) was added slowly to a stirred suspension of (fluoromethyl)triphenyl-phosphonium tetrafluoroborate (0.86 g, 2.26 mmol) at –78° C. under N$_2$. The mixture was stirred at 0° C. for 15 min and then cooled to –78° C. A solution of (2S,3S,4aR,8S,8aR)-tert-butyl 8-formyl-2,3-dimethoxy-2,3-dimethyltetrahydro-2H-spiro[[1,4]dioxino[2,3-c]pyridine-7,1'-cyclopropane]-6(3H)-carboxylate (290 mg, 0.75 mmol) was added slowly. The mixture was allowed to warm up to room temperature and stirred for 18 h. The reaction was quenched with saturated aqueous ammonium chloride, and diluted with EtOAc. The organic layer was washed with water, brine, dried, and concentrated. The residue was purified by chromatography to give (2S,3S,4aR,8S,8aR)-tert-butyl 8-((Z)-2-fluorovinyl)-2,3-dimethoxy-2,3-dimethyltetrahydro-2H-spiro[[1,4]dioxino[2,3-c]pyridine-7,1'-cyclopropane]-6(3H)-carboxylate (19 mg, 6%) as oil. $^1$H NMR (400 MHz, CDCl$_3$) δ 6.56 (ddd, J=0.8, 4.8, 83.6 Hz, 1H), 4.30-4.00 (m, 2H), 3.75-3.60 (m, 2H), 3.32 (s, 3H), 3.27 (s, 3H), 3.28-3.25 (m, 1H), 2.87 (t, J=11.2 Hz, 1H), 1.48 (s, 9H), 1.33 (s, 3H), 1.32 (s, 3H), 1.20-1.06 (br, 1H), 1.02-0.85 (m, 1H), 0.52-0.35 (m, 2H); MS, (ES, m/z) [M+Na]$^+$424.22.

A mixture of TFA (2 mL) and H₂O (0.2 mL) was cooled to 0° C., added to the above material (17 mg, 0.042 mmol) at 0° C. The mixture was stirred at 0° C. for 10 min, then room temperature for 4 h. TFA was removed under vacuum. The residue was purified by silica gel flash chromatography (using 70:20:2 DCM/MeOH/NH₄OH as eluent) to give (6R,7R,8S)-8-((Z)-2-fluorovinyl)-4-azaspiro[2.5]octane-6,7-diol (4.8 mg, 60%). ¹H NMR (400 MHz, CD₃OD) δ 6.65 (ddd, J=0.8, 4.8, 83.6 Hz, 1H), 4.55-4.35 (m, 1H), 3.54-3.46 (m, 1H), 3.27 (t, J=9.6 Hz, 1H), 3.10-2.98 (m, 2H), 2.52 (dd, J=10.8, 12.8 Hz, 1H), 0.60-0.48 (m, 3H), 0.42-0.34 (m, 1H); MS, (ES, m/z) [M+H]⁺ 188.12.

Example 18

(6R,7R,8S)-8-((E)-2-fluorovinyl)-4-azaspiro[2.5]octane-6,7-diol

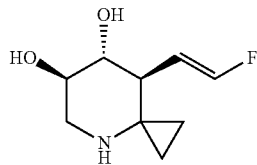 [SMILES: O[C@H]1[C@H](O)CNC2(CC2)[C@@H]1/C=C/F]

A freshly prepared solution of lithium diisoproylamide (2.26 mmol) in anhydrous THF (8 mL) was added slowly to a stirred suspension of (fluoromethyl)triphenyl-phosphonium tetrafluoroborate (0.86 g, 2.26 mmol) at −78° C. under N₂. The mixture was stirred at 0° C. for 15 min and then cooled to −78° C. A solution of (2S,3S,4aR,8S,8aR)-tert-butyl 8-formyl-2,3-dimethoxy-2,3-dimethyltetrahydro-2H-spiro[[1,4] dioxino[2,3-c]pyridine-7,1'-cyclopropane]-6(3H)-carboxylate (290 mg, 0.75 mmol) was added slowly. The mixture was allowed to warm up to room temperature and stirred for 18 h. The reaction was quenched with saturated aqueous ammonium chloride, and diluted with EtOAc. The organic layer was washed with water, brine, dried, and concentrated. The residue was purified by chromatography to give (2S,3S,4aR,8S,8aR)-tert-butyl 8-((E)-2-fluorovinyl)-2,3-dimethoxy-2,3-dimethyltetrahydro-2H-spiro[[1,4]dioxino[2,3-c]pyridine-7,1'-cyclopropane]-6(3H)-carboxylate (12 mg, 4%) as oil. ¹H NMR (400 MHz, CDCl₃) δ 6.59 (dd, J=10.8, 84.4 Hz, 1H), 4.75-4.62 (m, 1H), 4.15-3.90 (br, 1H), 3.72-3.55 (m, 2H), 3.31 (s, 3H), 3.26 (s, 3H), 2.89 (t, J=11.2 Hz, 1H), 2.65 (br, 1H), 1.46 (s, 9H), 1.33 (s, 6H), 1.23-1.10 (br, 1H), 1.07-0.95 (m, 1H), 0.60-0.40 (m, 2H); MS, (ES, m/z) [M+Na]⁺424.22.

A mixture of TFA (2 mL) and H₂O (0.2 mL) was cooled to 0° C., added to the above material (12 mg, 0.030 mmol) at 0° C. The mixture was stirred at 0° C. for 10 min, then room temperature for 4 h. TFA was removed under vacuum. The residue was purified by silica gel flash chromatography (using 70:20:2 DCM/MeOH/NH₄OH as eluent) to give (6R,7R,8S)-8-((E)-2-fluorovinyl)-4-azaspiro[2.5]octane-6,7-diol (3.2 mg, 57%). ¹H NMR (400 MHz, CD₃OD) δ 6.61 (dd, J=10.8, 85.2 Hz, 1H), 4.94 (t, J=10.8 Hz, 1H), 3.50-3.42 (m, 1H), 3.25 (t, J=8.4 Hz, 1H), 3.01 (dd, J=5.2, 10.8 Hz, 1H), 2.36 (dt, J=2.0, 10.4 Hz, 1H), 0.61-0.40 (m, 4H); MS, (ES, m/z) [M+H]⁺ 188.11.

Example 19

(6R,7R,8S)-8-(2,2-difluorovinyl)-4-azaspiro[2.5]octane-6,7-diol

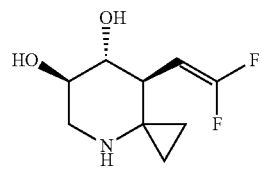 [SMILES: O[C@H]1[C@H](O)CNC2(CC2)[C@@H]1C=C(F)F]

To a stirred solution of fresh made lithium diisoproylamide (5.1 mmol) in anhydrous THF (15 mL) was added diethyldifluoromethyl phosphonate (0.80 mL, 5.1 mmol) at −78° C. under N₂. The mixture was stirred at −78° C. for 2 h. A solution of (2S,3S,4aR,8S,8aR)-tert-butyl 8-formyl-2,3-dimethoxy-2,3-dimethyltetrahydro-2H-spiro[[1,4]dioxino[2,3-c]pyridine-7,1'-cyclopropane]-6(3H)-carboxylate (278 mg, 0.72 mmol) was added slowly. After stirred at −78° C. for 30 min, the mixture was refluxed for 2 h, then stirred at room temperature for 18 h. The reaction was quenched with saturated aqueous ammonium chloride, and diluted with EtOAc. The organic layer was washed with water, brine, dried, and concentrated. The residue was purified by chromatography to give (2S,3S,4aR,8S,8aR)-tert-butyl 8-(2,2-difluorovinyl)-2,3-dimethoxy-2,3-dimethyltetrahydro-2H-spiro[[1,4]dioxino[2,3-c]pyridine-7,1'-cyclopropane]-6(3H)-carboxylate (258 mg, 85%) as light yellow oil. ¹H NMR (400 MHz, CDCl₃) δ 4.15-4.00 (br, 1H), 3.75-3.53 (m, 3H), 3.32 (s, 3H), 3.27 (s, 3H), 3.00-2.80 (br, 2H), 1.47 (s, 9H), 1.33 (s, 6H), 1.22-1.10 (br, 1H), 1.00-0.90 (m, 1H), 0.53-0.40 (m, 2H); MS, (ES, m/z) [M+Na]⁺442.21.

A mixture of TFA (2 mL) and H₂O (0.2 mL) was cooled to 0° C., added to the above material (68 mg, 0.16 mmol) at 0° C. The mixture was stirred at 0° C. for 10 min, then room temperature for 4 h. TFA was removed under vacuum. The residue was purified by silica gel flash chromatography eluting with 70:20:2 DCM/MeOH/NH₄OH to give (6R,7R,8S)-8-(2,2-difluorovinyl)-4-azaspiro[2.5]octane-6,7-diol (34 mg, 100%). ¹H NMR (400 MHz, CD₃OD) δ 4.04 (dd, J=8.8, 24.8 Hz, 1H), 3.58-3.50 (m, 1H), 3.28 (t, J=8.8 Hz, 1H), 3.09 (dd, J=4.8, 12.4 Hz, 1H), 2.67 (t, J=9.6 Hz, 1H), 2.60 (dd, J=10.0, 12.4 Hz, 1H), 0.68-0.55 (m, 3H), 0.54-0.46 (m, 1H); MS, (ES, m/z) [M+H]⁺ 206.10.

Example 20

(6R,7R,8S)-8-ethynyl-4-azaspiro[2.5]octane-6,7-diol

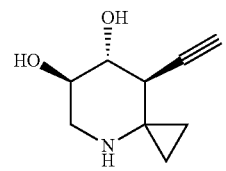

To a solution of (2S,3S,4aR,8R,8aR)-tert-butyl 8-(hydroxymethyl)-2,3-dimethoxy-2,3-dimethyltetrahydro-2H-spiro[[1,4]dioxino[2,3-c]pyridine-7,1'-cyclopropane]-6(3H)-carboxylate (278.8 mg, 0.72 mmol) in DCM (7 mL) was added DMP (458 mg, 1.08 mmol). The mixture was stirred for 1 h at room temperature then diluted with EtOAc (30 mL). The organic solution was washed with satd. aqueous NaHCO$_3$ and brine, then dried over MgSO$_4$. Evaporation of solvent gave the crude material which was purified by a silica gel flash chromatography, eluting with 20% EtOAc in hexanes to afford (2S,3S,4aR,8S,8aR)-tert-butyl-8-formyl-2,3-dimethoxy-2,3-dimethyltetrahydro-2H-spiro[[1,4]dioxino[2,3-c]pyridine-7,1'-cyclopropane]-6(3H)-carboxylate as a white solid (274 mg, 95%).

To a solution of the above material (274 mg, 0.71 mmol) in MeOH (10 mL) was added dimethyl(1-diazo-2-oxopropyl)phosphonate (279 mg, 1.45 mmol) followed by addition of K$_2$CO$_3$ (265 mg, 1.9 mmol). Gas evolution was observed and the reaction mixture became light yellow. The mixture was stirred overnight at room temperature, concentrated, and diluted with EtOAc (30 mL). The organic solution was washed with satd. aqueous NaHCO$_3$ and brine then dried over MgSO$_4$. Evaporation of solvent gave the crude material which was purified by a silica gel flash chromatography, eluting with 20% EtOAc in hexanes to afford (2S,3S,4aR,8S,8aR)-tert-butyl 8-ethynyl-2,3-dimethoxy-2,3-dimethyltetrahydro-2H-spiro[[1,4]dioxino[2,3-c]pyridine-7,1'-cyclopropane]-6(3H)-carboxylate (104 mg, 39%) as a white foam.

The above material (100 mg, 0.26 mmol) was dissolved in TFA/H$_2$O (9:1, 2 mL) and the mixture was stirred for 2 h at room temperature then evaporated to dryness. The crude material was purified by a silica gel flash chromatography, eluting with 5:10:85 NH$_4$OH:MeOH:DCM to afford (6R,7R,8S)-8-ethynyl-4-azaspiro[2.5]octane-6,7-diol (40 mg, 93%). $^1$H NMR (500 MHz, d-MeOH) δ 3.43-3.36 (m, 2H), 3.05 (dd, J=13, 4.5 Hz, 1H), 2.83 (d, J=8.5 Hz, 1H), 2.52-2.48 (m, 1H), 2.36 (d, J=2 Hz, 1H), 1.10-0.87 (m, 2H), 0.62-0.59 (m, 1H), 0.48-0.44 (m, 1H); MS m/z 168.10 (M+1, 100%).

Example 21

(6R,7R,8S)-8-(prop-1-yn-1-yl)-4-azaspiro[2.5]octane-6,7-diol

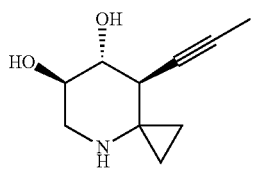

To a solution (2S,3S,4aR,8S,8aR)-tert-butyl 8-ethynyl-2,3-dimethoxy-2,3-dimethyltetrahydro-2H-spiro[[1,4]dioxino[2,3-c]pyridine-7,1'-cyclopropane]-6(3H)-carboxylate (107 mg, 0.28 mmol) in THF (2 mL) at −78° C. was added n-BuLi (1.6 M in hexanes, 0.2 mL, 0.34 mmol) and the resulting solution was stirred for 10 min at 0° C. After addition of MeI (0.1 mL, 1.62 mmol), the reaction was stirred for 3 h at room temperature, then concentrated and diluted with EtOAc (20 mL). The organic phase was washed with satd. aqueous NaHCO$_3$ and brine then dried over MgSO$_4$. Evaporation of solvent gave the crude material which was purified by silica gel flash chromatography, eluting with 10% EtOAc in hexanes to afford (2S,3S,4aR,8S,8aR)-tert-butyl 2,3-dimethoxy-2,3-dimethyl-8-(prop-1-yn-1-yl)tetrahydro-2H-spiro[[1,4]dioxino[2,3-c]pyridine-7,1'-cyclopropane]-6(3H)-carboxylate (103 mg, 93%) as a white foam.

The above material (103 mg, 0.26 mmol) was dissolved in TFA/H$_2$O (9:1, 2 mL) and the mixture was stirred for 2 h at room temperature then evaporated to dryness. The crude material was purified by silica gel flash chromatography, eluting with 5:10:85 NH$_4$OH:MeOH:DCM to afford (6R,7R,8S)-8-(prop-1-yn-1-yl)-4-azaspiro[2.5]octane-6,7-diol (32 mg, 70%) as a white foam. $^1$H NMR (400 MHz, d-MeOH) δ 3.42-3.36 (m, 2H), 3.96 (dd, J=12.8, 4.8 Hz, 1H), 2.77 (d, J=10 Hz, 1H), 2.48 (dd, J=10.4, 12.8 Hz, 1H), 1.76 (d, J=2.4, 3H), 0.89-0.81 (m, 2H), 0.58-0.54 (m, 1H), 0.43-0.40 (m, 1H); MS m/z 181.11 (M+1, 100%).

Example 22

(6R,7R,8S)-8-(but-1-yn-1-yl)-4-azaspiro[2.5]octane-6,7-diol

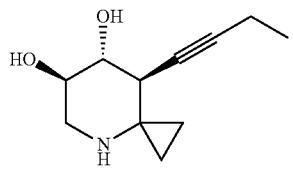

At 0° C. under N$_2$, to a mixture of PPh$_3$ (1.05 g, 4.01 mmol) and Zn dust (0.131 g, 2.00 mmol) in anhydrous DCM (30 mL) was added CBr$_4$ (0.663 g, 2.00 mmol). After the mixture was stirred at 0° C. for 15 min and then at room temperature for 20 min, a solution of (2S,3S,4aR,8S,8aR)-tert-butyl-8-formyl-2,3-dimethoxy-2,3-dimethyltetrahydro-2H-spiro[[1,4]dioxino[2,3-c]pyridine-7,1'-cyclopropane]-6(3H)-carboxylate (0.390 g, 1.01 mmol) in DCM (10 mL) was added. The reaction mixture was stirred at room temperature for 6 h, at which time completion was indicated by TLC. Hexane (50 mL) was added, and the resulting precipitate was filtered off. The filtrate was concentrated under reduced pressure, and the residue was purified on silica gel by automatic flash column chromatography (EtOAc/hexanes, 1:10 to 1:5), affording (2S,3S,4aR,8S,8aR)-tert-butyl dibromovinyl)-2,3-dimethoxy-2,3-dimethyltetrahydro-2H-spiro[[1,4]dioxino[2,3-c]pyridine-7,1'-cyclopropane]-6(3H)-carboxylate as a white solid (0.513 g, 98%). $^1$H NMR (400 MHz, CDCl$_3$) δ 5.83 (d, J=9.0 Hz, 1H), 4.09-4.01 (m, 1H), 3.74 (dd, J=9.5, 10.3 Hz, 1H), 3.71-3.63 (m, 1H), 3.29 (s, 3H), 3.25 (s, 3H), 3.01-2.95 (m, 1H), 2.85-2.78 (m, 1H), 1.46 (s, 9H), 1.31 (s, 3H), 1.30 (s, 3H), 1.21-1.13 (m, 1H), 0.99-0.93 (m, 1H), 0.47-0.38 (m, 2H).

At −78° C. under N$_2$, to a solution of the above material (0.130 g, 0.252 mmol) in anhydrous THF (6 mL) was added n-BuLi (1.6 M in hexanes, 0.47 mL, 0.75 mmol). After the mixture was stirred at −78° C. for 1 h, EtI (0.32 g, 2.0 mmol) was added. The reaction mixture was brought to room temperature and stirred overnight. Saturated aqueous NH$_4$Cl (10 mL) was added, and the mixture was extracted with EtOAc (3×10 mL). The combined organic extract was dried over anhydrous Na$_2$SO$_4$. After filtration the solvent was evaporated under reduced pressure, and the residue was purified on silica gel by flash column chromatography (EtOAc/hexanes, 1:10), affording (2S,3S,4aR,8S,8aR)-tert-butyl 8-(but-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as a white foam (0.044 g, 43%). $^1$H NMR (400 MHz, CDCl$_3$) δ 3.98 (s, br., 1H), 3.65 (dd, J=9.5, 10.4 Hz, 1H), 3.60-3.57 (m, 1H), 3.31 (s, 3H), 3.26 (s, 3H), 2.95-2.88 (m, 1H), 2.86-2.78 (m, 1H), 2.09 (dq, J=2.1, 7.5 Hz, 2H), 1.43 (s, 9H), 1.32 (s, 3H), 1.31 (s, 3H), 1.05 (t, J=7.5 Hz, 3H), 0.92-0.88 (m, 3H), 0.41-0.36 (m, 1H).

The above material (0.034 g, 0.083 mmol) was treated with TFA/H$_2$O (1.5 mL/0.15 mL) overnight. The solvent was removed, and the residue was neutralized with 1.0 M NH$_3$ in MeOH and subsequently purified on silica gel by flash column chromatography (1.0 M NH$_3$ in MeOH/DCM, 1:8), affording (6R,7R,8S)-8-(but-1-yn-1-yl)-4-azaspiro[2.5]octane-6,7-diol as a white solid (0.011 g, 70%). $^1$H NMR (400 MHz, CD$_3$OD) δ 3.42-3.35 (m, 1H), 2.97 (dd, J=4.8, 12.7 Hz, 1H), 2.80-2.74 (m, 1H), 2.48 (dd, J=10.6, 12.7 Hz, 1H), 2.13 (dq, J=2.2, 7.5 Hz, 2H), 1.09 (t, J=7.5 Hz, 3H), 0.92-0.82 (m, 2H), 0.60-0.54 (m, 1H), 0.44-0.40 (m, 1H); MS, m/z=196.13 [M+H].

Example 23

(6R,7R,8S)-8-(pent-1-yn-1-yl)-4-azaspiro[2.5]octane-6,7-diol

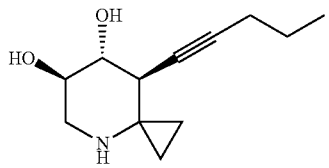

At −78° C., under N$_2$, to a solution of ((4aR,8S,8aR)-tert-butyl 8-(2,2-dibromovinyl)-2,3-dimethoxy-2,3-dimethyltetrahydro-2H-spiro[[1,4]dioxino[2,3-c]pyridine-7,1'-cyclopropane]-6(3H)-carboxylate (0.140 g, 0.259 mmol) in anhydrous THF (5 mL) was added n-BuLi (1.6 M in hexanes, 0.50 mL, 0.80 mmol). After the mixture was stirred at −78° C. for 2 h, CH$_3$CH$_2$CH$_2$I (0.52 g, 3.1 mmol) was added. The reaction mixture was brought to room temperature and stirred for 40 h. Saturated aqueous NH$_4$Cl (10 mL) was added, and the mixture was extracted with EtOAc (3×10 mL). The combined organic extract was dried over anhydrous Na$_2$SO$_4$. After filtration the solvent was evaporated under reduced pressure, and the residue was purified on silica gel by automatic flash column chromatography (EtOAc/hexanes, 1:15 to 1:8), affording (4aR,8S,8aR)-tert-butyl 2,3-dimethoxy-2,3-dimethyl-8-(pent-1-yn-1-yl)tetrahydro-2H-spiro[[1,4]dioxino[2,3-c]pyridine-7,1'-cyclopropane]-6(3H)-carboxylate as a clear oil (0.023 g, 21%). $^1$H NMR (400 MHz, CDCl$_3$) δ 3.99 (s, br., 1H), 3.66 (dd, J=9.6, 10.5 Hz, 1H), 3.60-3.54 (m, 1H), 3.31 (s, 3H), 3.27 (s, 3H), 2.97-2.94 (m, 1H), 2.85-2.79 (m, 1H), 2.09-2.04 (m, 2H), 1.46-1.39 (m, 2H), 1.43 (s, 9H), 1.33 (s, 3H), 1.30 (s, 3H), 1.17-1.13 (m, 1H), 0.93 (t, J=7.3 Hz, 3H), 0.90-0.86 (m, 2H), 0.43-0.39 (m, 1H).

The above material (0.023 g, 0.054 mmol) was treated with TFA/H$_2$O (1.5 mL/0.15 mL) overnight. The solvent was removed, and the residue was neutralized with 1.0 M NH$_3$ in MeOH and subsequently purified on silica gel by flash column chromatography (1.0 M NH$_3$ in MeOH/DCM, 1:7), affording (6R,7R,8S)-8-(pent-1-yn-1-yl)-4-azaspiro[2.5]octane-6,7-diol as a clear film (0.0083 g, 73%). $^1$H NMR (400 MHz, CD$_3$OD) δ 3.42-3.36 (m, 1H), 3.37-3.28 (m, 1H), 2.97 (dd, J=5.0, 12.7 Hz, 1H), 2.80-2.76 (m, 1H), 2.48 (dd, J=10.6, 12.7 Hz, 1H), 2.12 (dt, J=2.2, 7.1 Hz, 2H), 1.48 (hexa, J=7.1 Hz, 2H), 0.97 (t, J=7.1 Hz, 3H), 0.87-0.82 (m, 2H), 0.57-0.54 (m, 2H), 0.45-0.41 (m, 1H); MS, m/z=210.15 [M+H].

Example 24

(6R,7R,8S)-8-(3-hydroxyprop-1-yn-1-yl)-4-azaspiro[2.5]octane-6,7-diol

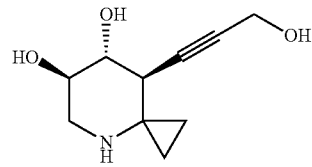

(4aR,8S,8aR)-tert-butyl 8-(3-hydroxyprop-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate (0.033 g, 0.080 mmol) was treated with TFA/H$_2$O (1.5 mL/0.15 mL) overnight. The solvent was removed, and the residue was neutralized with 1.0 M NH$_3$ in MeOH and subsequently purified on silica gel by flash column chromatography (1.0 M NH$_3$ in MeOH/DCM, 1:4), affording (6R,7R,8S)-8-(3-hydroxyprop-1-yn-1-yl)-4-azaspiro[2.5]octane-6,7-diol as a white foam (0.014 g, 86%). $^1$H NMR (400 MHz, CD$_3$OD) δ 4.14 (d, J=1.8 Hz, 2H), 3.49-3.37 (m, 2H), 3.05 (dd, J=4.5, 12.7 Hz, 1H), 2.90-2.86 (m, 1H), 2.57 (dd, J=10.2, 12.7 Hz, 1H), 0.99-0.90 (m, 2H), 0.69-0.64 (m, 1H), 0.55-0.51 (m, 1H); MS, m/z=198.11 [M+H].

Example 25

(6R,7R,8S)-8-(3-fluoroprop-1-yn-1-yl)-4-azaspiro[2.5]octane-6,7-diol

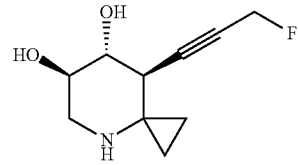 [SMILES: O[C@H]1[C@H](O)CNC2(CC2)[C@@H]1C#CCF]

At −78° C., under N$_2$, to a solution (4aR,8S,8aR)-tert-butyl 8-ethynyl-2,3-dimethoxy-2,3-dimethyltetrahydro-2H-spiro[[1,4]dioxino[2,3-c]pyridine-7,1'-cyclopropane]-6(3H)-carboxylate (0.240 g, 0.629 mmol) in anhydrous THF (6 mL) was added n-BuLi (1.6 M in hexanes, 0.44 mL, 0.70 mmol). After the mixture was stirred at −78° C. for 1 h, and then at 0° C. for 30 min, at −78° C. methyl chloroformate (0.085 g, 0.90 mmol) was added. The reaction mixture was brought to 0° C. and stirred at 0° C. for 2 h. Saturated aqueous NaHCO$_3$ (10 mL) was added, and the mixture was extracted with EtOAc (2×10 mL). The combined organic extract was dried over anhydrous Na$_2$SO$_4$. After filtration the solvent was evaporated under reduced pressure, and the residue was purified on silica gel by automatic flash column chromatography (EtOAc/hexanes, 1:15 to 1:6), affording (4aR,8S,8aR)-tert-butyl 2,3-dimethoxy-8-(3-methoxy-3-oxoprop-1-yn-1-yl)-2,3-dimethyltetrahydro-2H-spiro[[1,4]dioxino[2,3-c]pyridine-7,1'-cyclopropane]-6(3H)-carboxylate as a white foam (0.170 g, 61%). $^1$H NMR (400 MHz, CDCl$_3$) δ 4.01 (s, br., 1H), 3.81 (dd, J=9.5, 10.8 Hz, 1H), 3.61-3.54 (m, 1H), 3.32 (s, 3H), 3.28 (s, 3H), 3.14-3.10 (m, 1H), 2.87-2.81 (m, 1H), 1.46 (s, 9H), 1.33 (s, 3H), 1.31 (s, 3H), 1.35-1.30 (m, 1H), 1.27-1.21 (m, 1H), 0.90-0.87 (m, 1H), 0.54-0.48 (m, 1H).

At −78° C., under N₂, to a solution of the above material (0.170 g, 0.386 mmol) in anhydrous THF (5 mL) was added DIBAL-H (1.0 M in THF, 1.2 mL, 1.2 mmol). After the mixture was stirred at 0° C. for 2 h, saturated aqueous NaHCO₃ (10 mL) was added and the mixture was extracted with EtOAc (2×10 mL). The combined organic extract was dried over anhydrous Na₂SO₄. After filtration the solvent was evaporated under reduced pressure, and the residue was purified on silica gel by automatic flash column chromatography (EtOAc/hexanes, 1:4 to 1:2), affording (4aR,8S,8aR)-tert-butyl 8-(3-hydroxyprop-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as a white foam (0.145 g, 91%). ¹H NMR (400 MHz, CDCl₃) δ 4.18 (d, J=2.3 Hz, 2H), 3.98 (s, br., 1H), 3.70 (dd, J=9.5, 10.7 Hz, 1H), 3.59-3.52 (m, 1H), 3.30 (s, 3H), 3.26 (s, 3H), 3.03-3.00 (m, 1H), 2.86-2.79 (m, 1H), 1.43 (s, 9H), 1.32 (s, 3H), 1.29 (s, 3H), 1.30-1.26 (m, 1H), 1.20-1.15 (m, 1H), 0.89-0.84 (m, 1H), 0.46-0.40 (m, 1H).

At −78° C., under N₂, to a solution of the above material (0.120 g, 0.290 mmol) in anhydrous DCM (3 mL) was added DAST (0.43 g, 2.7 mmol). After the mixture was stirred at room temperature overnight, at −78° C. saturated aqueous NaHCO₃ (5 mL) was added and the mixture was extracted with DCM (2×5 mL). The combined organic extract was dried over anhydrous Na₂SO₄. After filtration the solvent was evaporated under reduced pressure, and the residue was purified on silica gel by automatic flash column chromatography (EtOAc/hexanes, 1:12 to 1:5), affording (4aR,8S,8aR)-tert-butyl 8-(3-fluoroprop-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as a white foam (0.112 g, 93%). ¹H NMR (400 MHz, CDCl₃) δ 4.89 (dd, J=1.9, 47.4 Hz, 2H), 4.04 (s, br., 1H), 3.75 (dd, J=9.9, 11.2 Hz, 1H), 3.61-3.55 (m, 1H), 3.31 (s, 3H), 3.28 (s, 3H), 3.10 (s, br., 1H), 2.87-2.81 (m, 1H), 1.44 (s, 9H), 1.34 (s, 3H), 1.31 (s, 3H), 1.32-1.25 (m, 1H), 1.23-1.18 (m, 1H), 0.92-0.86 (m, 1H), 0.49-0.43 (m, 1H).

The above material (0.112 g, 0.271 mmol) was treated with TFA/H₂O (2 mL/0.2 mL) overnight. The solvent was removed, and the residue was neutralized with 1.0 M NH₃ in MeOH and subsequently purified on silica gel by flash column chromatography (1.0 M NH₃ in MeOH/DCM, 1:7), affording (6R,7R,8S)-8-(3-fluoroprop-1-yn-1-yl)-4-azaspiro[2.5]octane-6,7-diol as a white foam (0.044 g, 81%). ¹H NMR (400 MHz, CD₃OD) δ 4.93 (dd, J=1.9, 47.5 Hz, 2H), 3.41-3.37 (m, 2H), 3.00-2.95 (m, 1H), 2.93-2.88 (m, 1H), 2.52-2.46 (m, 1H), 0.90-0.81 (m, 2H), 0.64-0.59 (m, 1H), 0.48-0.44 (m, 1H); MS, m/z=200.11 [M+H].

Example 26

(6R,7R,8S)-8-(3,3-difluoroprop-1-yn-1-yl)-4-azaspiro[2.5]octane-6,7-diol

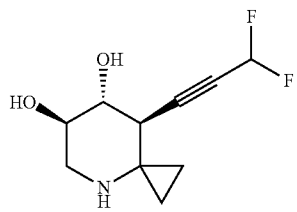 [SMILES: O[C@H]1[C@H](O)CNC2(CC2)[C@@H]1C#CC(F)F]

At −78° C., under N₂, to a solution ((4aR,8S,8aR)-tert-butyl 8-(2,2-dibromovinyl)-2,3-dimethoxy-2,3-dimethyltetrahydro-2H-spiro[[1,4]dioxino[2,3-c]pyridine-7,1'-cyclopropane]-6(3H)-carboxylate (0.160 g, 0.296 mmol) in anhydrous THF (6 mL) was added n-BuLi (1.6 M in hexanes, 0.75 mL, 1.2 mmol). After the mixture was stirred at −78° C. for 1.5 h, anhydrous DMF (0.2 mL) was added. The reaction mixture was brought to 0° C. and stirred at 0° C. for 2 h. Saturated aqueous NaHCO₃ (5 mL) was added, and the mixture was extracted with EtOAc (2×5 mL). The combined organic extract was dried over anhydrous Na₂SO₄. After filtration the solvent was evaporated under reduced pressure, and the residue was purified on silica gel by automatic flash column chromatography (EtOAc/hexanes, 1:6 to 1:4), affording (4aR,8S,8aR)-tert-butyl 2,3-dimethoxy-2,3-dimethyl-8-(3-oxoprop-1-yn-1-yl)tetrahydro-2H-spiro[[1,4]dioxino[2,3-c]pyridine-7,1'-cyclopropane]-6(3H)-carboxylate as a white foam (0.075 g, 62%). ¹H NMR (400 MHz, CDCl₃) δ 9.15 (d, J=0.6 Hz, 1H), 4.01 (s, br., 1H), 3.83 (dd, J=9.5, 10.8 Hz, 1H), 3.63-3.56 (m, 1H), 3.31 (s, 3H), 3.29 (s, 3H), 3.29-3.23 (m, 1H), 2.89-2.83 (m, 1H), 1.44 (s, 9H), 1.34 (s, 3H), 1.31 (s, 3H), 1.33-1.22 (m, 2H), 0.90-0.85 (m, 1H), 0.57-0.52 (m, 1H).

At −78° C., under N₂, to a solution of the above material (0.065 g, 0.16 mmol) in anhydrous DCM (3 mL) was added DAST (0.43 g, 2.7 mmol). After the mixture was stirred at room temperature for 3 days, at −78° C. saturated aqueous NaHCO₃ (5 mL) was added and the mixture was extracted with DCM (2×5 mL). The combined organic extract was dried over anhydrous Na₂SO₄. After filtration the solvent was evaporated under reduced pressure, and the residue was purified on silica gel by automatic flash column chromatography (EtOAc/hexanes, 1:12 to 1:5), affording (4aR,8S,8aR)-tert-butyl 8-(3,3-difluoroprop-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as a white foam (0.069 g, 100%). ¹H NMR (400 MHz, CDCl₃) δ 6.11 (dt, J=1.2, 55.0 Hz, 1H), 4.00 (s, br., 1H), 3.78 (dd, J=9.5, 10.8 Hz, 1H), 3.60-3.54 (m, 1H), 3.30 (s, 3H), 3.27 (s, 3H), 3.10 (s, br., 1H), 2.86-2.80 (m, 1H), 1.44 (s, 9H), 1.33 (s, 3H), 1.30 (s, 3H), 1.30-1.20 (m, 2H), 0.92-0.85 (m, 1H), 0.53-0.47 (m, 1H).

The above material (0.069 g, 0.16 mmol) was treated with TFA/H₂O (1.5 mL/0.15 mL) overnight. The solvent was removed, and the residue was neutralized with 1.0 M NH₃ in MeOH and subsequently purified on silica gel by flash column chromatography (1.0 M NH₃ in MeOH/DCM, 1:7), affording (6R,7R,8S)-8-(3,3-difluoroprop-1-yn-1-yl)-4-azaspiro[2.5]octane-6,7-diol as a white foam (0.028 g, 81%). ¹H NMR (400 MHz, CD₃OD) δ 6.33 (dt, J=1.2, 54.8 Hz, 1H), 3.45-3.37 (m, 2H), 3.01-2.94 (m, 2H), 2.53-2.47 (m, 1H), 0.89-0.79 (m, 2H), 0.69-0.64 (m, 1H), 0.54-0.49 (m, 1H); MS, m/z=218.10 [M+H].

Example 27

(6R,7R,8S)-8-(4-fluorobut-1-yn-1-yl)-4-azaspiro[2.5]octane-6,7-diol

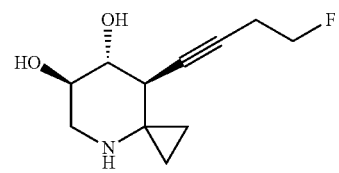 [SMILES: O[C@H]1[C@H](O)CNC2(CC2)[C@@H]1C#CCCF]

At −78° C., under N₂, to a solution of ((4aR,8S,8aR)-tert-butyl 8-(2,2-dibromovinyl)-2,3-dimethoxy-2,3-dimethyltetrahydro-2H-spiro[[1,4]dioxino[2,3-c]pyridine-7,1'-cyclopropane]-6(3H)-carboxylate (0.130 g, 0.240 mmol) in anhydrous THF (5 mL) was added n-BuLi (1.6 M in hexanes, 0.50 mL, 0.80 mmol). After the mixture was stirred at −78° C. for 1.5 h, FCH$_2$CH$_2$I (0.261 g, 1.50 mmoL) was added. The reaction mixture was brought to room temperature and stirred overnight. Saturated aqueous NH$_4$Cl (10 mL) was added, and the mixture was extracted with EtOAc (3×10 mL). The combined organic extract was dried over anhydrous Na$_2$SO$_4$. After filtration the solvent was evaporated under reduced pressure, and the residue was purified on silica gel by automatic flash column chromatography (EtOAc/hexanes, 1:15 to 1:8), affording (4aR,8S,8aR)-tert-butyl 8-(4-fluorobut-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as a white foam (0.0082 g, 8%). $^1$H NMR (400 MHz, CDCl$_3$) δ 4.40 (td, J=6.6, 46.7 Hz, 2H), 3.98 (s, br., 1H), 3.67 (dd, J=9.6, 10.6 Hz, 1H), 3.59-3.53 (m, 1H), 3.31 (s, 3H), 3.27 (s, 3H), 2.97-2.93 (m, 1H), 2.86-2.80 (m, 1H), 2.52 (dtd, J=2.1, 6.6, 19.7 Hz, 2H), 1.44 (s, 9H), 1.33 (s, 3H), 1.30 (s, 3H), 1.31-1.27 (m, 1H), 1.23-1.14 (m, 1H), 0.89-0.85 (m, 1H), 0.45-0.41 (m, 1H).

The above material (0.020 g, 0.047 mmol) was treated with TFA/H$_2$O (1.5 mL/0.15 mL) overnight. The solvent was removed, and the residue was neutralized with 1.0 M NH$_3$ in MeOH and subsequently purified on silica gel by flash column chromatography (1.0 M NH$_3$ in MeOH/DCM, 1:7), affording (6R,7R,8S)-8-(4-fluorobut-1-yn-1-yl)-4-azaspiro[2.5]octane-6,7-diol as a clear film (0.0044 g, 44%). $^1$H NMR (400 MHz, CD$_3$OD) δ 4.42 (td, J=6.4, 46.9 Hz, 2H), 3.41-3.29 (m, 2H), 2.96 (dd, J=4.8, 12.7 Hz, 1H), 2.80-2.78 (m, 1H), 2.54 (dtd, J=2.5, 6.4, 21.2 Hz, 2H), 2.47 (dd, J=10.4, 12.7 Hz, 1H), 0.91-0.82 (m, 2H), 0.58-0.54 (m, 1H), 0.44-0.39 (m, 1H); MS, m/z=214.12 [M+H].

Example 28

(6R,7R,8S)-8-(4,4-difluorobut-1-yn-1-yl)-4-azaspiro[2.5]octane-6,7-diol

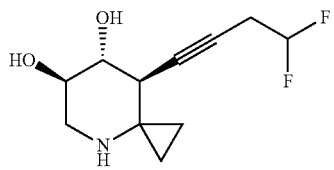

Under N$_2$, to a solution (4aR,8S,8aR)-tert-butyl 8-ethynyl-2,3-dimethoxy-2,3-dimethyltetrahydro-2H-spiro[[1,4]dioxino[2,3-c]pyridine-7,1'-cyclopropane]-6(3H)-carboxylate (0.100 g, 0.262 mmol) in anhydrous CH$_3$CN (5 mL) was added tert-butyl diazoacetate (0.075 g, 0.52 mmol), and CuI (0.015 g, 0.077 mmol). After the mixture was stirred at room temperature for 24 h, the solvent was evaporated under reduced pressure, and the residue was purified on silica gel by automatic flash column chromatography (EtOAc/hexanes, 1:10 to 1:4), affording (4aR,8S,8aR)-tert-butyl 8-(4-(tert-butoxy)-4-oxobut-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as an oil (0.045 g, 35%). Its $^1$H NMR is complex due to the existence of two stable rotamers in CDCl$_3$ at room temperature.

At 0° C., under N$_2$, to a solution of the above material (0.045 g, 0.091 mmol) in anhydrous THF (5 mL) was added DIBAL-H (1.0 M in THF, 0.30 mL, 0.30 mmol). After the mixture was stirred at 0° C. for 2 h, saturated aqueous NaHCO$_3$ (10 mL) was added and the mixture was extracted with EtOAc (2×10 mL). The combined organic extract was dried over anhydrous Na$_2$SO$_4$. After filtration the solvent was evaporated under reduced pressure, and the residue was purified on silica gel by automatic flash column chromatography (EtOAc/hexanes, 1:4 to 1:2), affording (4aR,8S,8aR)-tert-butyl 8-(4-hydroxybut-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as an oil (0.026 g, 67%). $^1$H NMR (400 MHz, CDCl$_3$) δ 4.00 (s, br., 1H), 3.69 (dd, J=9.6, 11.0 Hz, 1H), 3.62 (dt, J=1.3, 6.1 Hz, 2H), 3.59-3.53 (m, 1H), 3.31 (s, 3H), 3.27 (s, 3H), 3.02 (s, br., 1H), 2.87-2.81 (m, 1H), 2.37 (dt, J=2.2, 6.1 Hz, 2H), 1.44 (s, 9H), 1.34 (s, 3H), 1.31 (s, 3H), 1.31-1.25 (m, 1H), 1.23-1.15 (m, 1H), 0.89-0.82 (m, 1H), 0.46-0.40 (m, 1H).

To a solution of the above material (0.026 g, 0.061 mmol) in DCM (3 mL) was added DMP (0.075 g, 0.18 mmol), and the mixture was stirred at room temperature for 1 h. The solvent was removed and the residue was diluted with saturated aqueous NaHCO$_3$ (5 mL), and then extracted with EtOAc (3×5 mL). The combined organic extract was dried over anhydrous Na$_2$SO$_4$. After filtration the solvent was evaporated under reduced pressure, and the residue, (4aR,8S,8aR)-tert-butyl 2,3-dimethoxy-2,3-dimethyl-8-(4-oxobut-1-yn-1-yl)tetrahydro-2H-spiro[[1,4]dioxino[2,3-c]pyridine-7,1'-cyclopropane]-6(3H)-carboxylate, was dissolved in anhydrous DCM (3 mL). At −78° C., under N$_2$, to the solution was added DAST (0.43 g, 2.7 mmol). After the mixture was stirred at room temperature for 3 days, at −78° C. saturated aqueous NaHCO$_3$ (5 mL) was added and the mixture was extracted with DCM (2×5 mL). The combined organic extract was dried over anhydrous Na$_2$SO$_4$. After filtration the solvent was evaporated under reduced pressure, and the residue was purified on silica gel by automatic flash column chromatography (EtOAc/hexanes, 1:12 to 1:5), affording (4aR,8S,8aR)-tert-butyl 8-(4,4-difluorobut-1-yn-1-yl)-2,3-dimethoxy-2,3-dimethyltetrahydro-2H-spiro[[1,4]dioxino[2,3-c]pyridine-7,1'-cyclopropane]-6(3H)-carboxylate as an oil (0.015 g, 55% in 2 steps). $^1$H NMR (400 MHz, CDCl$_3$) δ 5.77 (tt, J=4.4, 56.3 Hz, 1H), 3.99 (s, br., 1H), 3.70 (dd, J=9.5, 10.7 Hz, 1H), 3.59-3.52 (m, 1H), 3.30 (s, 3H), 3.27 (s, 3H), 2.99 (s, br., 1H), 2.86-2.80 (m, 1H), 2.68 (ddt, J=2.2, 4.4, 15.5 Hz, 2H), 1.44 (s, 9H), 1.33 (s, 3H), 1.30 (s, 3H), 1.30-1.24 (m, 1H), 1.23-1.15 (m, 1H), 0.90-0.85 (m, 1H), 0.460-0.42 (m, 1H).

The above material (0.015 g, 0.034 mmol) was treated with TFA/H$_2$O (1 mL/0.1 mL) overnight. The solvent was removed, and the residue was neutralized with 1.0 M NH$_3$ in MeOH and subsequently purified on silica gel by flash column chromatography (1.0 M NH$_3$ in MeOH/DCM, 1:7), affording (6R,7R,8S)-8-(4,4-difluorobut-1-yn-1-yl)-4-azaspiro[2.5]octane-6,7-diol as a white foam (0.0060 g, 77%). $^1$H NMR (400 MHz, CD$_3$OD) δ 5.91 (tt, J=4.2, 56.4 Hz, 1H), 3.42-3.34 (m, 2H), 2.97 (dd, J=4.2, 12.7 Hz, 1H), 2.83-2.81 (m, 1H), 2.74 (ddt, J=2.2, 4.2, 16.1 Hz, 2H), 2.49 (dd, J=10.4, 12.7 Hz, 1H), 0.92-0.83 (m, 2H), 0.61-0.57 (m, 1H), 0.47-0.42 (m, 1H); MS, m/z =232.12 [M+H].

Examples 29 to 76, as indicated in Table 1, are synthesized according to procedures analogous to the schemes and examples outlined herein.

Biological Activity

Assay for Determination of Ki Values for Inhibition of GCase Activity

Various concentrations of test compounds were prepared in DMSO and then diluted into buffer consisting of 50 mM sodium phosphate 0.25% w/v sodium taurodexoycholate, pH 7.0. GCase enzyme (Cerezyme®, recombinant human GCase obtained from R&D Systems) was diluted in the same buffer to 0.143 nM. The reaction solution consisted of 25 μL of 6 mM 4-methylumbelliferone-β-D glucopyranoside in 10% DMSO in the same buffer, 12.5 μL of enzyme and 12.5 μL of various concentrations of test compound diluted in buffer. The final concentrations in the reaction were 0.036 nM GCase, 3 mM 4-methylumbelliferone-β-D glucopyranoside, and various concentrations of inhibitor. The reaction was initiated by addition of enzyme and allowed to proceed for 20 min at 37° C. to assess GCase activity. Reactions were stopped by the addition of an equal volume (50 μL) of 0.5 M NaOH, 0.3 M glycine, pH 10.5. Fluorescence was measured on a Biotek Synergy H4 plate reader using a setting of 10 measurements per data point at wavelengths of 365 nm for excitation and 450 nm for emission. Incubations without added enzyme or added inhibitors were used to define no enzyme activity and maximal enzyme activity, respectively. $IC_{50}$ values were determined by fitting the data to a log[inhibitor concentration] versus response curve using GraphPad Prism. $IC_{50}$ values were calculated as the concentration of inhibitor required to inhibit GCase activity by 50%. Ki values were determined from the $IC_{50}$ values by employing the Cheng-Prusoff equation using a GCase Km of 7.9 mM for 4-methylumbelliferone-β-D glucopyranoside at pH 7.0.

The compounds of the invention tested exhibit Ki values for inhibition of GCase in the range 0.1 nM-50 μM.

Assay for Determination of Apparent Permeability ($P_{app}$)

Bi-directional transport is evaluated in LLC-PK1 cells in order to determine apparent permeability ($P_{app}$). LLC-PK1 cells can form a tight monolayer and therefore can be used to assess vectorial transport of compounds from basolateral to apical (B→A) and from apical to basolateral (A→B).

To determine $P_{app}$, LLC-PK1 cells are cultured in 96-well transwell culture plates (Millipore). Solutions containing the test compounds (1 μM) are prepared in Hank's Balanced Salt Solution with 10 mM HEPES. Substrate solution (150 μL) is added to either the apical (A) or the basolateral (B) compartment of the culture plate, and buffer (150 μL) is added to the compartment opposite to that containing the compound. At t=3 h, 50 μL samples are removed from both sides of monolayers dosed with test compound and placed in 96 well plates, scintillant (200 μL) or internal standard (100 μL labetolol 1 μM) is added to the samples and concentration is determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 μM) is used as the positive control. The experiment is performed in triplicate.

The apparent permeability, $P_{app}$, is calculated by the following formula for samples taken at t=3 h:

$$P_{app} = \frac{\text{Volume of Receptor Chamber (mL)}}{[\text{Area of membrane (cm}^2\text{)}][\text{Initial Concentration (}\mu M\text{)}]} \times$$

$$x \frac{\Delta \text{ in Concentration (}\mu M\text{)}}{\Delta \text{ in Time (s)}}$$

Where: Volume of Receptor Chamber is 0.15 mL; Area of membrane is 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). $P_{app}$ is expressed as $10^{-6}$ cm/s. The $P_{app}$ (LLC-PK1 cells) are the average of the $P_{app}$ for transport from A to B and $P_{app}$ for transport from B to A at t=3 h:

$$P_{app}(LLC-PK1 \text{ Cells}) = \frac{P_{app}(A \rightarrow B) + P_{app}(B \rightarrow A)}{2}$$

Representative data from the binding assay described above are shown in the following table. For comparison, the first two table entries show data for literature compounds (3R,4R,5R)-5-(hydroxymethyl)piperidine-3,4-diol and (3R,4R,5R)-5-(hydroxymethyl)-6,6-dipropylpiperidine-3,4-diol.

TABLE 2

| Example | Structure | GCase $IC_{50}$ (nM) | GCase Ki (nM) |
|---|---|---|---|
| N/A | | 8.2 | 1.7 |
| N/A | | ND | 1400[a] |
| N/A | | 3,440 | ND |
| 1 | 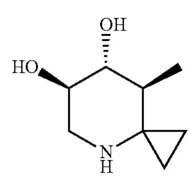 | 3.7 | 2.6 |
| 2 | 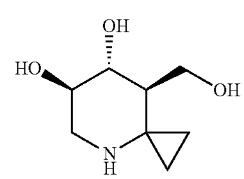 [SMILES: OC[C@@H]1[C@@H](O)[C@H](O)CNC12CC2] | 13 | 7.0 |
| 3 | 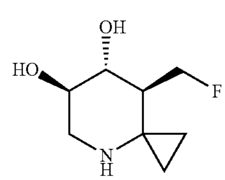 [SMILES: O[C@H]1[C@H](O)CNC2(CC2)[C@@H]1CF] | 6.2 | 2.1 |

TABLE 2-continued

| Example | Structure | GCase IC$_{50}$ (nM) | GCase Ki (nM) |
|---|---|---|---|
| 4 | OH, F, HO, NH, cyclopropane spiro, CHF$_2$ | 6.5 | 8.0 |
| 5 | OH, HO, NH, cyclopropane spiro, CH$_2$Cl | 7.4 | ND |
| 6 | OH, HO, NH, cyclopropane spiro, CH$_2$OMe | 7.5 | ND |
| 7 | OH, HO, NH, cyclopropane spiro, OMe | 32 | ND |
| 8 | OH, HO, NH, cyclopropane spiro, CN | 75 | ND |
| 9 | OH, HO, NH, cyclopropane spiro, COOH | 507 | ND |
| 10 | OH, HO, NH, cyclopropane spiro, C(O)NHMe | 264 | ND |
| 11 | OH, HO, NH, cyclopropane spiro, C(O)NH-cyclopropyl | 462 | ND |
| 12 | OH, HO, NH, cyclopropane spiro, ethyl | 6.3 | ND |
| 13 | OH, HO, NH, cyclopropane spiro, propyl | 15 | ND |
| 14 | OH, HO, NH, cyclopropane spiro, CH$_2$CH$_2$F | 27 | ND |
| 15 | OH, HO, NH, cyclopropane spiro, CH$_2$CHF$_2$ | 56 | ND |
| 16 | OH, HO, NH, cyclopropane spiro, vinyl | 6.8 | 7.6 |
| 17 | OH, HO, NH, cyclopropane spiro, cis-CH=CHF | 36 | ND |
| 18 | OH, HO, NH, cyclopropane spiro, trans-CH=CHF | 20 | ND |
| 19 | OH, HO, NH, cyclopropane spiro, CH=CF$_2$ | 75 | ND |
| 20 | OH, HO, NH, cyclopropane spiro, C≡CH | 13 | 7.9 |
| 21 | OH, HO, NH, cyclopropane spiro, C≡CH | 9.7 | 6.7 |

TABLE 2-continued

| Example | Structure | GCase IC$_{50}$ (nM) | GCase Ki (nM) |
|---|---|---|---|
| 22 | (OH, HO, piperidine fused cyclopropane, N-H, propynyl) | 2.4 | ND |
| 23 | (OH, HO, piperidine fused cyclopropane, N-H, butynyl) | 6.7 | ND |
| 24 | (OH, HO, piperidine fused cyclopropane, N-H, propynyl-OH) | 17 | ND |
| 25 | (OH, HO, piperidine fused cyclopropane, N-H, propynyl-F) | 16 | 15 |
| 26 | (OH, HO, piperidine fused cyclopropane, N-H, propynyl-CHF$_2$) | 22 | 17 |
| 27 | (OH, HO, piperidine fused cyclopropane, N-H, propynyl-CH$_2$F) | 2.5 | ND |
| 28 | (OH, HO, piperidine fused cyclopropane, N-H, propynyl-CHF-CH$_2$F) | 11 | ND |

$^a$From Hill et al. ChemBioChem 2011, 12, 2151, Ki measured at pH 7.0.

The present invention has been described with regard to one or more embodiments. However, it will be apparent to persons skilled in the art that a number of variations and modifications can be made without departing from the scope of the invention as defined in the claims.

REFERENCES

1. Al-Mansoori, K. M. et al. *Current Alzheimer Research* 2013, 10, 559-568.
2. Sardi, S. et al. *Proceedings of the National Academy of Sciences* 2013, 110, 3537-3542.
3. Sardi, S. et al. *Neurodegenerative Diseases* 2012, 10, 195-202.
4. Sardi, S. et al. *Proceedings of the National Academy of Sciences* 2011, 108, 12101-12106.
5. Kong, B. et al. *European Review for Medical and Pharmaceutical Sciences* 2013, 17, 143-151.
6. Clark, S. et al. "Improved Pharmacological Chaperones for the Treatment of Neuronopathic Gaucher and Parkinson's Disease," Lysosomal Disease Network, World Symposium, 2011.
7. Chesselet, M.-F. et al. *Neurotherapeutics* 2012, 9, 677-678.
8. Grabowski, G. A. *Lancet* 2008, 372, 1263-1271.
9. Boyd, R. E. et al. *Journal of Medicinal Chemistry* 2013, 56, 2705-2725.
10. Parenti, G. *EMBO Molecular Medicine* 2009, 1, 268-279.
11. Fan, J. Q. *Trends in Pharmaceutical Sciences* 2003, 24, 355-360.
12. Alberio, T. et al. *FEBS Journal* 2012, 279, 1146-1155.
13. Dawson, T. M. et al. *Neuron* 2010, 66, 646-661.
14. Khanna, R. et al. *FEBS Journal* 2010, 277, 1618-1638.
15. Panicker, L. M. *Proceedings of the National Academy of Sciences* 2012, 109, 18054-18059.
16. Farfel-Becker, T. et al. *Disease Models & Mechanisms* 2011, 4, 746-752.

What is claimed is:

1. A method of modulating a Gcase or elevating the level of GCase protein and/or GCase enzyme activity, in a subject, the method comprising administering to the subject an effective amount of a compound of Formula (I) or a pharmaceutically acceptable salt thereof:

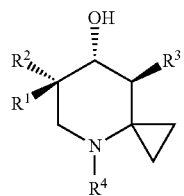

(I)

wherein $R^1$ is OH and $R^2$ is H or methyl; or $R^1$ is F and $R^2$ is H or F; or $R^1$ is H and $R^2$ is F;

$R^3$ is: $C_{1-10}$ alkyl, $C_{2-10}$ alkenyl, $C_{2-10}$ alkynyl, $C_{1-10}$ alkoxy, $C_{3-8}$ cycloalkyl, $C_{4-10}$ cycloalkylalkyl, $C_{2-10}$ alkoxyalkyl, $C_{7-15}$ arylalkyl, or $C_{2-15}$ heteroarylalkyl, each optionally substituted from one up to the maximum number of substituents with one or more of F, Cl, $CH_3$, and/or OH; or $R^3$ is CN, $CO_2H$, $C(O)NHCH_3$, or $C(O)NH(cyclopropyl)$; and $R^4$ is: H or $C_{1-10}$ alkyl, said $C_{1-10}$ alkyl optionally substituted from one up to the maximum number of substituents with F and/or OH.

2. The method of claim 1 wherein the compound is:
(6R,7R,8S)-8-methyl-4-azaspiro[2.5]octane-6,7-diol;
(6R,7R,8R)-8-(hydroxymethyl)-4-azaspiro[2.5]octane-6,7-diol;
(6R,7R,8S)-8-(fluoromethyl)-4-azaspiro[2.5]octane-6,7-diol;
(6R,7R,8S)-8-(difluoromethyl)-4-azaspiro[2.5]octane-6,7-diol;
(6R,7R,8S)-8-(chloromethyl)-4-azaspiro[2.5]octane-6,7-diol;
(6R,7R,8R)-8-(methoxymethyl)-4-azaspiro[2.5]octane-6,7-diol;
(6R,7S,8S)-8-methoxy-4-azaspiro[2.5]octane-6,7-diol;
(6R,7R,8R)-6,7-dihydroxy-4-azaspiro[2.5]octane-8-carbonitrile;
(6R,7R,8S)-6,7-dihydroxy-4-azaspiro[2.5]octane-8-carboxylic acid;
(6R,7R,8S)-6,7-dihydroxy-N-methyl-4-azaspiro[2.5]octane-8-carboxamide;
(6R,7R,8S)-N-cyclopropyl-6,7-dihydroxy-4-azaspiro[2.5]octane-8-carboxamide;
(6R,7R,8S)-8-ethyl-4-azaspiro[2.5]octane-6,7-diol;
(6R,7R,8S)-8-propyl-4-azaspiro[2.5]octane-6,7-diol;
(6R,7R,8S)-8-(2-fluoroethyl)-4-azaspiro[2.5]octane-6,7-diol;
(6R,7R,8S)-8-(2,2-difluoroethyl)-4-azaspiro[2.5]octane-6,7-diol;
(6R,7R,8S)-8-vinyl-4-azaspiro[2.5]octane-6,7-diol;
(6R,7R,8S)-8-((Z)-2-fluorovinyl)-4-azaspiro[2.5]octane-6,7-diol;
(6R,7R,8S)-8-((E)-2-fluorovinyl)-4-azaspiro[2.5]octane-6,7-diol;
(6R,7R,8S)-8-(2,2-difluorovinyl)-4-azaspiro[2.5]octane-6,7-diol;
(6R,7R,8S)-8-ethynyl-4-azaspiro[2.5]octane-6,7-diol;
(6R,7R,8S)-8-(prop-1-yn-1-yl)-4-azaspiro[2.5]octane-6,7-diol;
(6R,7R,8S)-8-(but-1-yn-1-yl)-4-azaspiro[2.5]octane-6,7-diol;
(6R,7R,8S)-8-(pent-1-yn-1-yl)-4-azaspiro[2.5]octane-6,7-diol;
(6R,7R,8S)-8-(3-hydroxyprop-1-yn-1-yl)-4-azaspiro[2.5]octane-6,7-diol;
(6R,7R,8S)-8-(3-fluoroprop-1-yn-1-yl)-4-azaspiro[2.5]octane-6,7-diol;
(6R,7R,8S)-8-(3,3-difluoroprop-1-yn-1-yl)-4-azaspiro[2.5]octane-6,7-diol;
(6R,7R,8S)-8-(4-fluorobut-1-yn-1-yl)-4-azaspiro[2.5]octane-6,7-diol; or
(6R,7R,8S)-8-(4,4-difluorobut-1-yn-1-yl)-4-azaspiro[2.5]octane-6,7-diol;
or a pharmaceutically acceptable salt of any of the foregoing compounds.

3. The method of claim 1 wherein the subject is a human.

4. The method of claim 1 wherein:
$R^1$ is OH and $R^2$ is H;
$R^3$ is: methyl, hydroxymethyl, fluoromethyl, difluoromethyl, chloromethyl, methoxymethyl, methoxy, CN, $CO_2H$, $C(O)NHCH3$, $C(O)NH(cyclopropyl)$; ethyl, propyl, 2-fluoroethyl, 2,2-difluoroethyl, vinyl, (Z)-2-fluorovinyl, (E)-2-fluorovinyl, 2,2-difluorovinyl, ethynyl, prop-1-yn-1-yl, but-1-yn-1-yl, pent-1-yn-1-yl, 3-hydroxyprop-1-yn-1-yl, 3-fluoroprop-1-yn-1-yl, 3,3-difluoroprop-1-yn-1-yl, or 4,4-difluorobut-1-yn-1-yl; and
$R^4$ is H.

5. The method of claim 1 wherein the compound is:
(6R,7R,8S)-8-methyl-4-azaspiro[2.5]octane-6,7-diol;
(6R,7R,8S)-8-ethyl-4-azaspiro[2.5]octane-6,7-diol;
(6R,7R,8S)-8-propyl-4-azaspiro[2.5]octane-6,7-diol;
(6R,7R,8S)-8-ethynyl-4-azaspiro[2.5]octane-6,7-diol;
(6R,7R,8S)-8-(fluoromethyl)-4-azaspiro[2.5]octane-6,7-diol;
(6R,7R,8S)-8-(difluoromethyl)-4-azaspiro[2.5]octane-6,7-diol;
or a pharmaceutically acceptable salt of any of the foregoing compounds.

6. The method of claim 1 wherein the compound is (6R,7R,8S)-8-ethyl-4-azaspiro[2.5]octane-6,7-diol or a pharmaceutically acceptable salt thereof.

7. The method of claim 1 wherein the compound is (6R,7R,8S)-8-ethynyl-4-azaspiro[2.5]octane-6,7-diol or a pharmaceutically acceptable salt thereof.

8. The method of claim 1 wherein the compound is (6R,7R,8S)-8-(difluoromethyl)-4-azaspiro[2.5]octane-6,7-diol or a pharmaceutically acceptable salt thereof.

9. The method of claim 1 wherein the compound or a pharmaceutically acceptable salt thereof is in the form of a pharmaceutical composition in combination with a pharmaceutically acceptable carrier.

10. The method of claim 2 wherein the compound or a pharmaceutically acceptable salt thereof is in the form of a pharmaceutical composition in combination with a pharmaceutically acceptable carrier.

11. The method of claim 5 wherein the compound or a pharmaceutically acceptable salt thereof is in the form of a pharmaceutical composition in combination with a pharmaceutically acceptable carrier.

\* \* \* \* \*

SEQUENCE LISTING

<160> NUMBER OF SEQ ID NOS: 5

<210> SEQ ID NO 1
<211> LENGTH: 536
<212> TYPE: PRT
<213> ORGANISM: Homo sapiens

<400> SEQUENCE: 1

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45
```

```
Gly Tyr Ser Ser Val Val Cys Val Cys Asn Ala Thr Tyr Cys Asp Ser
     50                  55                  60

Phe Asp Pro Pro Thr Phe Pro Ala Leu Gly Thr Phe Ser Arg Tyr Glu
 65                  70                  75                  80

Ser Thr Arg Ser Gly Arg Arg Met Glu Leu Ser Met Gly Pro Ile Gln
             85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Ala Met Thr Asp Ala Ala
            115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
            195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
            290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
450                 455                 460
```

```
Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
            530                 535

<210> SEQ ID NO 2
<211> LENGTH: 41
<212> TYPE: PRT
<213> ORGANISM: Homo sapiens

<400> SEQUENCE: 2

Gln Ser Val Arg Leu Gly Ser Trp Asp Arg Gly Met Gln Tyr Ser His
1               5                   10                  15

Ser Ile Ile Thr Ser Leu Leu Tyr His Val Val Gly Trp Thr Asp Trp
                20                  25                  30

Asn Leu Ala Leu Asn Pro Glu Gly Gly
            35                  40

<210> SEQ ID NO 3
<211> LENGTH: 41
<212> TYPE: PRT
<213> ORGANISM: Homo sapiens

<400> SEQUENCE: 3

Ser Lys Phe Ile Pro Glu Gly Ser Gln Arg Val Gly Leu Val Ala Ser
1               5                   10                  15

Gln Lys Asn Asp Pro Asp Ala Val Ala Leu Met His Pro Asp Gly Ser
                20                  25                  30

Ala Val Val Val Val Leu Asn Arg Ser
            35                  40

<210> SEQ ID NO 4
<211> LENGTH: 41
<212> TYPE: PRT
<213> ORGANISM: Homo sapiens

<400> SEQUENCE: 4

Gly Lys Gly Ser Leu Lys Gly Gln Pro Gly Asp Ile Tyr His Gln Thr
1               5                   10                  15

Trp Ala Arg Tyr Ile Val Lys Phe Leu Asp Ala Tyr Ala Glu His Lys
                20                  25                  30

Leu Gln Phe Trp Ala Val Thr Ala Glu
            35                  40

<210> SEQ ID NO 5
<211> LENGTH: 41
<212> TYPE: PRT
<213> ORGANISM: Homo sapiens
```

```
<400> SEQUENCE: 5

Pro Thr Trp Leu Lys Thr Asn Gly Ala Val Asn Gly Lys Gly Ser Leu
1               5                   10                  15

Lys Gly Gln Pro Arg Asp Ile Tyr His Gln Thr Trp Ala Arg Tyr Phe
            20                  25                  30

Val Lys Phe Leu Asp Ala Tyr Ala Glu
        35                  40
```